(12) United States Patent
Ghiassian et al.

(10) Patent No.: US 11,783,913 B2
(45) Date of Patent: *Oct. 10, 2023

(54) METHODS OF TREATING A SUBJECT SUFFERING FROM RHEUMATOID ARTHRITIS WITH ALTERNATIVE TO ANTI-TNF THERAPY BASED IN PART ON A TRAINED MACHINE LEARNING CLASSIFIER

(71) Applicant: Scipher Medicine Corporation, Waltham, MA (US)

(72) Inventors: Susan Ghiassian, Boston, MA (US); Theodore R. Mellors, Boston, MA (US); Marc Santolini, Waltham, MA (US); Asher Ameli, Waltham, MA (US); Nancy Schoenbrunner, Charlestown, MA (US); Viatcheslav R. Akmaev, Sudbury, MA (US); Keith J. Johnson, Wayland, MA (US)

(73) Assignee: SCIPHER MEDICINE CORPORATION, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/881,441

(22) Filed: Aug. 4, 2022

(65) Prior Publication Data
US 2022/0375541 A1 Nov. 24, 2022

Related U.S. Application Data

(63) Continuation of application No. 17/517,521, filed on Nov. 2, 2021, now Pat. No. 11,456,056, which is a continuation of application No. 17/315,580, filed on May 10, 2021, now Pat. No. 11,195,595, which is a continuation of application No. PCT/US2020/039991, filed on Jun. 26, 2020.

(60) Provisional application No. 62/965,486, filed on Jan. 24, 2020, provisional application No. 62/882,402, filed on Aug. 2, 2019, provisional application No. 62/867,853, filed on Jun. 27, 2019.

(51) Int. Cl.
| | |
|---|---|
| *A61P 37/06* | (2006.01) |
| *C07K 16/24* | (2006.01) |
| *G16B 20/20* | (2019.01) |
| *G16H 10/60* | (2018.01) |
| *G16H 50/70* | (2018.01) |
| *G16H 50/20* | (2018.01) |
| *G16H 20/10* | (2018.01) |
| *A61P 19/02* | (2006.01) |
| *G16B 40/00* | (2019.01) |
| *A61K 38/17* | (2006.01) |

(52) U.S. Cl.
CPC .......... *G16B 20/20* (2019.02); *A61K 38/1793* (2013.01); *A61P 19/02* (2018.01); *A61P 37/06* (2018.01); *C07K 16/241* (2013.01); *G16B 40/00* (2019.02); *G16H 10/60* (2018.01); *G16H 20/10* (2018.01); *G16H 50/20* (2018.01); *G16H 50/70* (2018.01); *C07K 2317/21* (2013.01); *C07K 2317/24* (2013.01); *C07K 2317/55* (2013.01); *C07K 2317/76* (2013.01)

(58) Field of Classification Search
CPC .... A61P 37/06; C07K 16/241; C07K 2317/76
See application file for complete search history.

(56) References Cited

U.S. PATENT DOCUMENTS

| | | |
|---|---|---|
| 7,863,021 B2 | 1/2011 | Schrodi et al. |
| 7,919,264 B2 | 4/2011 | Maksymowych et al. |
| 7,935,482 B2 | 5/2011 | Bankaitis-Davis et al. |
| 8,092,998 B2 | 1/2012 | Stuhlmuller et al. |
| 9,086,418 B2 | 7/2015 | Maksymowych et al. |
| 9,200,324 B2 | 12/2015 | Cavet et al. |
| 9,387,246 B2 | 7/2016 | Graham |
| 9,753,041 B2 | 9/2017 | Alman et al. |
| 9,822,400 B2 | 11/2017 | Dennis, Jr. et al. |
| 9,945,870 B2 | 4/2018 | Weiskopf et al. |
| 10,018,637 B2 | 7/2018 | Schafer et al. |
| 10,086,072 B2 | 10/2018 | Singh et al. |
| 10,161,936 B2 | 12/2018 | Wagner |
| 10,246,748 B2 | 4/2019 | Therianos et al. |
| 10,301,679 B2 | 5/2019 | Schrodi et al. |
| 10,324,088 B2 | 6/2019 | Singh et al. |
| 10,385,398 B2 | 8/2019 | Hakonarson et al. |
| 10,571,467 B2 | 2/2020 | Singh et al. |
| 10,718,765 B2 | 7/2020 | Eastman et al. |
| 11,195,595 B2 | 12/2021 | Ghiassian et al. |
| 11,198,727 B2 | 12/2021 | Johnson et al. |

(Continued)

FOREIGN PATENT DOCUMENTS

| | | |
|---|---|---|
| EP | 3165928 A1 | 5/2017 |
| WO | WO-2008154423 A2 | 12/2008 |
| WO | WO-2010044952 A2 | 4/2010 |
| WO | WO-2012066536 A2 | 5/2012 |
| WO | WO-2014052064 A1 | 4/2014 |

(Continued)

OTHER PUBLICATIONS

ABREU., Anti-TNF Failures in Crohn's Disease.Gastroenterol Hepatol (N.Y.), 7(1):37-39 (2011).

(Continued)

*Primary Examiner* — Robert S Landsman
(74) *Attorney, Agent, or Firm* — WILSON SONSINI GOODRICH & ROSATI

(57) ABSTRACT

Presented herein are systems and methods for developing classifiers useful for predicting response to particular treatments. For example, in some embodiments, the present disclosure provides a method of treating subjects suffering from an autoimmune disorder, the method comprising administering an alternative to anti-TNF therapy to subjects who have been determined to be non-responsive via a classifier established to distinguish between responsive and non-responsive prior subjects in a cohort who have received the anti-TNF therapy.

14 Claims, 24 Drawing Sheets

(56) References Cited

U.S. PATENT DOCUMENTS

| | | |
|---|---|---|
| 2004/0120952 A1 | 6/2004 | Knight et al. |
| 2009/0221522 A1 | 9/2009 | Hidalgo et al. |
| 2010/0303813 A1 | 12/2010 | Carulli et al. |
| 2011/0059445 A1 | 3/2011 | Rutgeerts et al. |
| 2011/0160085 A1 | 6/2011 | Li et al. |
| 2011/0257893 A1 | 10/2011 | Taylor et al. |
| 2012/0039900 A1 | 2/2012 | Stuhlmüller et al. |
| 2012/0041683 A1 | 2/2012 | Vaske et al. |
| 2012/0158391 A1 | 6/2012 | Vaske et al. |
| 2013/0040835 A1 | 2/2013 | Harris |
| 2015/0142465 A1 | 5/2015 | Vaske et al. |
| 2015/0301058 A1 | 10/2015 | Schettini et al. |
| 2016/0042119 A1 | 2/2016 | Lehrach et al. |
| 2016/0110496 A1 | 4/2016 | Taylor et al. |
| 2016/0146831 A1 | 5/2016 | Hueber et al. |
| 2016/0162657 A1 | 6/2016 | Menche et al. |
| 2016/0194709 A1 | 7/2016 | Nagy et al. |
| 2016/0232279 A1 | 8/2016 | Ghiassian et al. |
| 2017/0145501 A1 | 5/2017 | Folkersen |
| 2018/0011966 A1 | 1/2018 | Vaske et al. |
| 2018/0046751 A1 | 2/2018 | Vaske et al. |
| 2018/0046752 A1 | 2/2018 | Vaske et al. |
| 2019/0050523 A1 | 2/2019 | Ghiassian et al. |
| 2019/0060449 A1 | 2/2019 | Singh et al. |
| 2019/0080051 A1 | 3/2019 | Menche et al. |
| 2019/0287644 A1 | 9/2019 | Karma et al. |
| 2020/0303078 A1 | 9/2020 | Mayhew et al. |
| 2020/0309774 A1 | 10/2020 | Gerwien et al. |
| 2021/0325387 A1 | 10/2021 | Shalek et al. |
| 2022/0056121 A1 | 2/2022 | Johnson et al. |
| 2022/0101946 A1 | 3/2022 | Ghiassian et al. |
| 2022/0392564 A1 | 12/2022 | Ghiassian et al. |

FOREIGN PATENT DOCUMENTS

| | | |
|---|---|---|
| WO | WO-2015006213 A1 | 1/2015 |
| WO | WO-2015084461 A2 | 6/2015 |
| WO | WO-2017083564 A1 | 5/2017 |
| WO | WO-2017091777 A1 | 6/2017 |
| WO | WO-2017093750 A1 | 6/2017 |
| WO | WO-2019018440 A1 | 1/2019 |
| WO | WO-2019178546 A1 | 9/2019 |
| WO | WO-2020198704 A1 | 10/2020 |
| WO | WO-2020264426 A1 | 12/2020 |
| WO | WO-2022051245 A2 | 3/2022 |
| WO | WO-2022197968 A1 | 9/2022 |

OTHER PUBLICATIONS

Barabasi et al., Network medicine: a network-based approach to human disease. Nat. Rev. Genet 12(1):56-68 (2011).

Bienkowska et al., Convergent random forest predictor: Methodology for predicting drug response from genome-scale data applied to anti-TNF response. Genomics 94:423-432 (2009).

Cao et al., Going the distance for protein function prediction: a new distance metric for protein interaction networks. PLOS One 8(10):e76339 (2013).

De Souza et al., The IBD Interactome: an Integrated View of Aetiology, Pathogenesis and Therapy. Nature Reviews Gastroenterology & Hepatology 14(12):739-749 (2017).

Del Sol et al., Diseases as network perturbations. Curr. Opin. Biotechnol., 21(4):566-571 (2010).

Ding et al., Systematic review: predicting and optimizing response to anti-TNF therapy in Crohn's disease—algorithm for practical management. Aliment Pharmacol. Ther., 43(1):30-51 (2016).

Eisenberg et al., Human housekeeping genes, revisited. Trends in Genetics 29(10):569-574 (2013).

Goodman et al., What does research reproducibility mean? Sci. Transl. Med. 8(341):341-353 (2016).

Hall et al., Genetics and the placebo effect: the placebome. Trends Mol. Med. 21(5):285-294 (2015).

Han et al., Evidence for dynamically organized modularity in the yeast protein-protein interaction network. Nature 430: 88-93 (2004).

Hanauer et al., Maintenance infliximab for Crohn's disease: the ACCENT I randomized trial. Lancet 359:1541-1549 (2002).

Ioannidis et al., Replication validity of genetic association studies. Nat. Genet. 29:(3)306-309 (2001).

Ioannidis., Why most published research findings are false. PLoS Med. 2(8):e124 (2005).

Johnson et al., Adjusting batch effects in microarray expression data using empirical Bayes methods. Biostatistics 8(1):118-127 (2007).

Julia et al., An Eight-Gene Blood Expression Profile Predicts the Response to Infliximab in Rheumatoid Arthritis. PLOS One 4(10):e7556 (2009).

Karagianni et al. An integrative transcriptome analysis framework for drug efficacy and similarity reveals drug-specific signatures of anti-TNF treatment in a mouse model of inflammatory polyarthritis. PLoS Computational Biology 15(5):e1006933 (2019).

Kim et al., Applications of systems approaches in the study of rheumatic diseases. Korean J Intern Med 30:148-160 (2015).

Menche et al., Uncovering disease-disease relationships through the incomplete interactome. Science 347(6224):1257601 (2015).

Nakamura et al., Identification of baseline gene expression signatures predicting therapeutic responses to three biologic agents in rheumatoid arthritis: a retrospective observational study. Arthritis Research & Therapy 18:159 (2016).

PCT/US2019/022588 International Search Report and Written Opinion dated May 28, 2019.

PCT/US2020/039991 International Search Report and Written Opinion dated Nov. 24, 2020.

Putrik et al., Variations in Criteria Regulating Treatment with Reimbursed Biologic DMARDs Across European Counties, Are Differences Related to Country's Wealth? Ann Rheum Dis 73(11):2010-2021 (2014).

Roda et al., Loss of Response to Anti-TNFs: Definition, Epidemiology, and Management. Clin. Gastroentorl., 7:e135 (2016).

Sakaram et al. A Multi-mRNA Prognostic Signature for Anti-TNFα Therapy Response in Patients with Inflammatory Bowel Disease. Diagnostics (Basel). 11(10):1902 (2021).

Sands et al., infliximab maintenance therapy for fistulizing Crohn's disease. N. Engl. J. Med., 350:876-885 (2004)).

Santolini., A personalized, multiomics approach identifies genes involved in cardiac hypertrophy and heart failure. Systems Biology and Applications 4:12 (2018).

Specht., Probabilistic Neural Networks. Neural Networks 3(1):109-118 (1990).

Thomson et al., Blood-based identification of non-responders to anti-TNF therapy in rheumatoid arthritis. BMC Med Genomics 8:26 (2015).

Toon et al., Validation Study of Existing Gene Expression Signatures for Anti-TNF Treatment in Patients with Rheumatoid Arthritis. PLOS ONE 7(3):e33199 (2012).

U.S. Appl. No. 17/517,521 Office Action dated Mar. 4, 2022.

Wachi et al., Interactome-transcriptome analysis reveals the high centrality of genes differentially expressed in lung cancer tissues. Bioinformatics 21(23):4205-8 (2005).

Winthrop et al., The unmet need in rheumatology: Reports from the targeted therapies meeting 2017. Clin. Immunol., 186:87-93 (2018).

Xing et al., Causal Modeling Using Network Ensemble Simulations of Genetic and Gene Expression Data Predicts Genes Involved in Rheumatoid Arthritis. PLOS One 7(3):e1001105 (2011).

You et al., A Systems Approach to Rheumatoid Arthritis. PLOS One 7(12):e51508 (2012).

Arijs et al., Mucosal gene signatures to predict response to infliximab in patients with ulcerative colitis. Gut 58: 1612-1619 (2009).

Fausel et al. Biologies in the management of ulcerative colitis—comparative safety and efficacy of TNF-α antagonists. Ther Clin Risk Manag. 11:63-73 (2015).

Fine et al., Etiology and Management of Lack or Loss of Response to Anti-Tumor Necrosis Factor Therapy in Patients With Inflammatory Bowel Disease. Gastroenterol Hepatol (N Y). 15(12):656-65 (2019).

(56) References Cited

OTHER PUBLICATIONS

Ford et al. Efficacy of biological therapies in inflammatory bowel disease: systematic review and meta-analysis. Am J Gastroenterol. 106(4):644-59 (2011).

Garcia-Bosch et al. Observational study on the efficacy of adalimumab for the treatment of ulcerative colitis and predictors of outcome. J Crohns Colitis. 7(9):717-22 (2013).

Ghiassian et al. Endophenotype Network Models: Common Core of Complex Diseases. Sci Rep.6:27414 (2016).

Ghiassian et al. Network-based response module comprised of gene expression biomarkers predicts response to infliximab at treatment initiation in ulcerative colitis. Translational Research S1931-5244(21):1-9 (2021).

Gonzalez-Camacho et al., Genome-enabled prediction using probabilistic neural network classifiers. BMC Genomics. 17:208 (2016).

Jostins et al.: Host-microbe interactions have shaped the genetic architecture of inflammatory bowel disease. Nature; 491/7422:119-124 (2012).

Olsen et al. TNF-alpha gene expression in colorectal mucosa as a predictor of remission after induction therapy with infliximab in ulcerative colitis. Cytokine. 46(2):222-7 (2009).

PCT/US2021/048346 International Search Report and Written Opinion dated Apr. 14, 2022.

PCT/US2022/020815 International Invitation to Pay Additional Fees dated Jun. 7, 2022.

PCT/US2022/020815 International Search Report and Written Opinion dated Aug. 17, 2022.

Rismo et al. Mucosal cytokine gene expression profiles as biomarkers of response to infliximab in ulcerative colitis. Scandinavian J. Gastroenterology 47(5):538-547 (2012).

Rutgeerts et al. Infliximab for induction and maintenance therapy for ulcerative colitis. N Engl J Med. 353(23):2462-76 (2005).

Sandborn et al. Adalimumab induces and maintains clinical remission in patients with moderate-to-severe ulcerative colitis. Gastroenterology. 142(2):257-65.e1-3 (2012).

Sharma et al. A disease module in the interactome explains disease heterogeneity, drug response and captures novel pathways and genes in asthma. Hum Mol Genet. 24(11):3005-20 (2015).

Specht. Generation of Polynomial Discriminant Functions for Pattern Recognition. IEEE Transactions on Electronic Computers. EC-16(3):308-19 (1967).

Specht. Probabilistic neural networks and the polynomial Adaline as complementary techniques for classification. IEEE Trans Neural Netw. 1(1):111-21 (1990).

Subramaniam et al. Early predictors of colectomy and long-term maintenance of remission in ulcerative colitis patients treated using anti-tumour necrosis factor therapy. Intern Med J. 44(5):464-70 (2014).

U.S. Appl. No. 17/315,580 Office Action dated Sep. 17, 2021.

U.S. Appl. No. 17/517,496 Office Action dated Jul. 21, 2022.

U.S. Appl. No. 17/517,496 Office Action dated Mar. 15, 2022.

Wang et al., Gene expression profile predicting the response to anti-TNF antibodies therapy in patients with inflammatory bowel disease: analyses of GEO datasets. International Journal of Clinical and Experimental Medicine 9(12):23397-23406 (2016).

Zampeli et al. Predictors of response to anti-tumor necrosis factor therapy in ulcerative colitis. World J Gastrointest Pathophysiol. 5(3):293-303 (2014).

U.S. Appl. No. 17/517,496 Office Action dated Dec. 23, 2022.

|  | PrismRA (+) | PrismRA (-) |
|---|---|---|
| Truth (+) | 26 | 4 |
| Truth (-) | 27 | 33 |

|  | PrismRA (+) | PrismRA (-) |
|---|---|---|
| Truth (+) | 15 | 2 |
| Truth (-) | 7 | 11 |

METHODS OF TREATING A SUBJECT SUFFERING FROM RHEUMATOID ARTHRITIS WITH ALTERNATIVE TO ANTI-TNF THERAPY BASED IN PART ON A TRAINED MACHINE LEARNING CLASSIFIER

CROSS REFERENCE TO RELATED APPLICATIONS

The present application is a continuation of U.S. application Ser. No. 17/517,521, filed Nov. 2, 2021, now U.S. Pat. No. 11,456,056 issued Sep. 27, 2022, which is a continuation of U.S. application Ser. No. 17/315,580, filed May 10, 2021, now U.S. Pat. No. 11,195,595 issued Dec. 7, 2021, which is a continuation of International Application No. PCT/US2020/039991, filed Jun. 26, 2020, which claims the benefit of U.S. Provisional Application No. 62/965,486, filed Jan. 24, 2020, U.S. Provisional Application No. 62/882,402, filed Aug. 2, 2019, and U.S. Provisional Application No. 62/867,853, filed Jun. 27, 2019, each incorporated by reference in their entirety.

The subject matter of this patent application is related to pending International Patent Application No. PCT/US19/22588, entitled, "Methods and Systems for Predicting Response to Anti-TNF Therapies," filed Mar. 15, 2019, which claims priority to and benefit of U.S. Provisional Application No. 62/644,070, filed Mar. 16, 2018, each incorporated by reference in their entirety.

BACKGROUND

Autoimmune diseases such as rheumatoid arthritis (RA) affect millions of patients, and their treatments represent a significant component of overall healthcare expenditure. Autoimmune diseases can be divided into two groups— organ-specific and systemic autoimmunity. Rheumatoid diseases including RA belong to the systemic autoimmune diseases which primarily manifests in synovial joints and eventually causes irreversible destruction of tendons, cartilage, and bone. Although there is no current cure for RA, significant improvements have been made to manage the treatment of these patients mainly through the development of anti-TNF (tumor necrosis factor) agents, which act to neutralize the pro-inflammatory signalling of this cytokine. Such biologic therapies (e.g., adalimumab (Humira®), etanercept (Enbrel®), infliximab (Remicade®), golimumab (Simponi®), and certolizumab pegol (Cimzia®)) have significantly improved the treatment outcome of some RA patients.

Roughly 34% of RA patients (a low percentage) show a clinical response to anti-TNF therapies, achieving low disease activity (LDA) and sometimes achieving remission. Disease progression in these so called "responder" patients, is likely a result of inappropriate TNF-driven pro-inflammatory responses. For patients failing to respond to anti-TNFs, there are alternative approved therapies available such as anti-CD20, co-stimulation blockade, JAK and anti-IL6 therapy. However, patients are typically switched onto such alternative therapy only after first cycling through different anti-TNFs, which could take over a year, while symptoms persist and the disease progresses further, making it more difficult to reach treatment targets.

In addition to the problem of delay in treatment, known risks of serious infection and malignancy associated with anti-TNF therapy are so significant that product approvals typically require so-called "black box warnings" be included on the label. Other potential side effects of such therapy include, for example, congestive heart failure, demyelinating disease, and other systemic side effects.

Moreover, precision medicine relies on the ability to interpret genomic and/or multi-omic data using proprietary algorithms developed with machine learning, artificial intelligence, and network science approaches using omic data and clinical outcomes. A major challenge, however, is that the software to analyze omic data is constantly being improved and updated. Such updates are extremely difficult to implement in a timely fashion, given the need to lock and validate systems, including the software component, in the clinical lab environment.

SUMMARY

A significant known problem with anti-TNF therapies is that response rates are inconsistent. Indeed, recent international conferences designed to bring together leading scientists and clinicians in the fields of immunology and rheumatology to identify unmet needs in these fields almost universally identify uncertainty in response rates as an ongoing challenge. For example, the $19^{th}$ annual International Targeted Therapies meeting, which held break-out sessions relating to challenges in treatment of a variety of diseases, including rheumatoid arthritis, psoriatic arthritis, axial spondyloarthritis, systemic lupus erythematous, and connective tissue diseases (e.g. Sjogren's syndrome, Systemic sclerosis, vasculitis including Bechet's and IgG4 related disease), identified certain issues common to all of these diseases, specifically, "the need for better understanding the heterogeneity within each disease . . . so that predictive tools for therapeutic responses can be developed. See Winthrop, et al., "The unmet need in rheumatology: Reports from the targeted therapies meeting 2017," *Clin. Immunol.* pii: S1521-6616(17)30543-0, Aug. 12, 2017. Similarly, extensive literature relating to treatment of Crohn's Disease with anti-TNF therapy consistently bemoans erratic response rates and inability to predict which patients will benefit. See, e.g., M. T. Abreu, "Anti-TNF Failures in Crohn's Disease," *Gastroenterol Hepatol* (N.Y.), 7(1):37-39 (January 2011); see also Ding et al., "Systematic review: predicting and optimising response to anti-TNF therapy in Crohn's disease—algorithm for practical management," *Aliment Pharmacol. Ther.,* 43(1):30-51 (January 2016) (reporting that "[p]rimary nonresponse to anti-TNF treatment affects 13-40% of patients.").

Provided technologies, among other things, permit care providers to distinguish between or among categories of subjects—e.g., subjects likely to benefit from a particular therapy (e.g., anti-TNF therapy) from those who are not, those who are more likely to achieve or suffer a particular outcome or side effect, etc. In some embodiments, such provided technologies thus reduce risks to patients, increase timing and quality of care for non-responder patient populations, increase efficiency of drug development, and/or avoid costs associated with administering ineffective therapy to non-responder patients or with treating side effects such patients experience upon receiving the relevant therapy (e.g., anti-TNF therapy).

In some embodiments, the present disclosure provides a method of treating subjects with particular therapy (e.g., anti-TNF therapy), the method comprising a step of: administering the therapy to subjects who have been determined to be responsive via a classifier established to distinguish between subjects expected to be responsive vs non-responsive to the therapy.

Among other things, embodiments of a classifier useful for determining whether a subject is responsive or non-responsive to certain therapies, and/or to achieve or suffer from a particular outcome or side effect, is described further herein, as well as methods of preparing such a classifier.

Provided technologies embody and/or arise from, among other things, certain insights that include, for example, identification of the source of a problem with certain conventional approaches to defining responder vs. non-responder populations and/or that represent particularly useful strategies for defining classifiers that distinguish between such populations.

For example, as described herein, the present disclosure utilizes an insight provided by WO 2019/178546 that one source of a problem with many conventional strategies for defining responder vs. non-responder populations through consideration of gene expression differences in the populations is that they typically prioritize or otherwise focus on highest fold (i.e., significant) changes; as described in WO 2019/178546, such an approach misses subtle but meaningful differences relevant to disease biology. Moreover, the present disclosure also utilizes the insight, also described in WO 2019/178546, that mapping of genes with altered expression levels onto a human interactome map (in particular onto a human interactome map that represents experimentally supported physical interactions between cellular components which, in some embodiments, explicitly excludes any theoretical, calculated, or other interaction that has been proposed but not experimentally validated), can provide a useful and effective classifier for defining responders vs. non-responders to certain therapies, and in particular to anti-TNF therapy. In some embodiments, genes included in such a classifier represent a connected module on the human interactome.

The present disclosure further provides an insight that particularly useful therapeutic classifiers are developed through use of cross-platform data. For example, the present disclosure teaches that combination of differential gene expression analysis with sequence analysis, e.g., single nucleotide polymorphism (SNP) analysis, of expressed sequences is particularly useful in development of therapeutic classifiers (i.e., of classifiers that predict likelihood that subject(s) will respond to and/or will achieve or suffer one or more particular outcome or side effect(s), etc. when/if administered a relevant therapy.

A significant known problem with various therapies (e.g., anti-TNF) therapies is that response rates are inconsistent. Indeed, recent international conferences designed to bring together leading scientists and clinicians in the fields of immunology and rheumatology to identify unmet needs in these fields almost universally identify uncertainty in response rates as an ongoing challenge. For example, the 19$^{th}$ annual International Targeted Therapies meeting, which held break-out sessions relating to challenges in treatment of a variety of diseases, including rheumatoid arthritis, psoriatic arthritis, axial spondyloarthritis, systemic lupus erythematous, and connective tissue diseases (e.g. Sjogren's syndrome, systemic sclerosis, vasculitis including Bechet's and IgG4 related disease), identified certain issues common to all of these diseases, specifically, "the need for better understanding the heterogeneity within each disease . . . so that predictive tools for therapeutic responses can be developed. See Winthrop, et al., "The unmet need in rheumatology: Reports from the targeted therapies meeting 2017," *Clin. Immunol.* pii: S1521-6616(17)30543-0, Aug. 12, 2017. Similarly, extensive literature relating to treatment of Crohn's Disease with anti-TNF therapy consistently bemoans erratic response rates and inability to predict which patients will benefit. See, e.g., M. T. Abreu, "Anti-TNF Failures in Crohn's Disease," *Gastroenterol Hepatol* (N.Y.), 7(1):37-39 (January 2011); see also Ding et al., "Systematic review: predicting and optimising response to anti-TNF therapy in Crohn's disease—algorithm for practical management," *Aliment Pharmacol. Ther.*, 43(1):30-51 (January 2016) (reporting that "[p]rimary nonresponse to anti-TNF treatment affects 13-40% of patients.").

Thus, a significant number of patients to whom anti-TNF therapy is currently being administered do not benefit from the treatment and could even be harmed. Known risks of serious infection and malignancy associated with anti-TNF therapy are so significant that product approvals typically require so-called "black box warnings" be included on the label. Other potential side effects of such therapy include, for example, congestive heart failure, demyelinating disease, and other systemic side effects. Furthermore, given that several weeks to months of treatment are required before a patient is identified as not responding to anti-TNF therapy (i.e., is a non-responder to anti-TNF therapy), proper treatment of such patients can be significantly delayed as a result of the current inability to identify responder vs non-responder subjects. See, e.g., Roda et al., "Loss of Response to Anti-TNFs: Definition, Epidemiology, and Management," *Clin. Tranl. Gastroenterol.*, 7(1): e135 (January 2016) (citing Hanauer et al., "ACCENT I Study group. Maintenance Infliximab for Crohn's disease: the ACCENT I randomized trial," *Lancet* 59:1541-1549 (2002); Sands et al., "Infliximab maintenance therapy for fistulizing Crohn's disease," *N. Engl. J. Med.* 350:876-885 (2004)).

Accordingly, in some embodiments, the present disclosure provides a method of treating subjects with anti-TNF therapy, the method comprising a step of: administering the anti-TNF therapy to subjects who have been determined to be responsive via a classifier established to distinguish between responsive and non-responsive prior subjects who have received the anti-TNF therapy wherein the classifier that is developed by assessing: one or more genes whose expression levels significantly correlate (e.g., in a linear and/or non-linear manner) to clinical responsiveness or non-responsiveness; and at least one of: presence of one or more single nucleotide polymorphisms (SNPs) in an expressed sequence of the one or more genes; or at least one clinical characteristic of the responsive and non-responsive prior subjects.

In some embodiments, the present disclosure provides a method of treating an inflammatory disease, disorder, or condition comprising a step of administering an anti-TNF therapy to subjects classified as responsive by application of a classifier determined to predict responsiveness of subjects with at least 90% accuracy across a population of at least 170 subjects.

In some embodiments, the present disclosure provides a method of developing a classifier for stratifying subjects with respect to one or more therapeutic attributes comprising steps of: analyzing sequence data of RNA expressed in subjects representing at least two different categories with respect to at least one of the therapeutic attributes; assessing the presence of one or more single nucleotide polymorphisms (SNPs) from the sequence data; determining the presence of the one or more SNPs correlates with the at least one therapeutic attribute; and including the one or more SNPs in the classifier.

In some embodiments, the present disclosure provides, in a method of developing a classifier for stratifying subjects with respect to one or more therapeutic attributes by analyzing sequence data of RNA expressed in subjects representing at least two different categories with respect to at least one of the therapeutic attributes, the improvement that comprises: assessing presence of one or more single nucleotide polymorphisms (SNPs) from the sequence data; determining the presence of the one or more SNPs correlates with the at least one therapeutic attribute; and including the one or more SNPs in the classifier.

In some embodiments, the present disclosure provides a method of treating subjects suffering from an autoimmune disorder, the method comprising a step of: administering an anti-TNF therapy to subjects who have been determined to be responsive via a classifier established to distinguish between responsive and non-responsive prior subjects in a cohort who have received the anti-TNF therapy; wherein the classifier is developed by assessing: one or more genes whose expression levels significantly correlate (e.g., in a linear and/or non-linear manner) to clinical responsiveness or non-responsiveness; at least one of: presence of one or more single nucleotide polymorphisms (SNPs) in an expressed sequence of the one or more genes; or at least one clinical characteristic of the responsive and non-responsive prior subjects; and wherein the classifier is validated by an independent cohort than the cohort who have received the anti-TNF therapy.

In some embodiments, the classifier predicts responsiveness of subjects with at least 90% accuracy across a population of at least 170 subjects. In some embodiments, the one or more genes are characterized by their topological properties when mapped on a human interactome map. In some embodiments, the SNPs are identified in reference to a human genome. In some embodiments, the classifier is developed by assessing each of: the one or more genes whose expression levels significantly correlate (e.g., in a linear and/or non-linear manner) to clinical responsiveness or non-responsiveness; presence of the one or more SNPs; and the at least one clinical characteristic.

In some embodiments, the one or more genes are selected from:

| | |
|---|---|
| ARPC1A | LOC100506083 |
| ATAT1 | MORN2 |
| ATRAID | NGF |
| CD27 | RHOBTB1 |
| CHMP7 | RNGTT |
| COMMD5 | SETD9 |
| CORO2B | SNX8 |
| CYSLTR2 | SPINT2 |
| DNAJC7 | SPON2 |
| GOLGA1 | SSNA1 |
| HPCA | STOML2 |
| IMPDH2 | SUOX |
| KAT8 | TMEM258 |
| KLHDC3 | UBL7-AS1 |

In some embodiments, the at least one clinical characteristic is selected from: body-mass index (BMI), gender, age, race, previous therapy treatment, disease duration, C-reactive protein level, presence of anti-cyclic citrullinated peptide, presence of rheumatoid factor, patient global assessment, treatment response rate (e.g., ACR20, ACR50, ACR70), and combinations thereof. In some embodiments, the classifier identifies at least 40% of subjects within a population that are non-responsive with at least 90% accuracy, wherein the population comprises at least 170 subjects.

In some embodiments, the anti-TNF therapy comprises administration of infliximab, adalimumab, etanercept, certolizumab pegol, golimumab, or biosimilars thereof. In some embodiments, the disease, disorder, or condition is selected from rheumatoid arthritis, psoriatic arthritis, ankylosing spondylitis, Crohn's disease, ulcerative colitis, chronic psoriasis, hidradenitis suppurativa, multiple sclerosis, and juvenile idiopathic arthritis. In some embodiments, the classifier is established using microarray analysis derived from the responsive and non-responsive prior subjects. In some embodiments, the classifier is validated using RNAseq data derived from the independent cohort. In some embodiments, the SNPs are selected from Table 5.

In some embodiments, the present disclosure provides a method of administering a therapy to a subject suffering from an autoimmune disease, the method comprising administering the therapy to subjects who have been classified as responsive or non-responsive via a classifier established to distinguish between responsive and non-responsive prior subjects in a cohort who have received the anti-TNF therapy; wherein, if the subject is classified as responsive by the classifier, administering an anti-TNF therapy; and if the subject is classified as non-responsive by the classifier, administering an alternative to anti-TNF therapy; and the classifier is developed by assessing: one or more genes whose expression levels significantly correlate (e.g., in a linear and/or non-linear manner) to clinical responsiveness or non-responsiveness; at least one of: presence of one or more single nucleotide polymorphisms (SNPs) in an expressed sequence of the one or more genes; or at least one clinical characteristic of the responsive and non-responsive prior subjects; and the classifier is validated by an independent cohort than the cohort who have received the anti-TNF therapy.

In some embodiments, the classifier predicts responsiveness of subjects with at least 90% accuracy across a population of at least 170 subjects. In some embodiments, the classifier is developed by assessing each of: the one or more genes whose expression levels significantly correlate (e.g., in a linear and/or non-linear manner) to clinical responsiveness or non-responsiveness; presence of the one or more SNPs; and the at least one clinical characteristic.

In some embodiments, the at least one clinical characteristic of the subject is selected from: body-mass index (BMI), gender, age, race, previous anti-TNF therapy treatment, disease duration (e.g., disease of RA), C-reactive protein level, presence of anti-cyclic citrullinated peptide, presence of rheumatoid factor, patient global assessment, treatment response rate to anti-TNF therapy (e.g., ACR20, ACR50, ACR70), and combinations thereof. In some embodiments, the anti-TNF therapy comprises administration of infliximab, adalimumab, etanercept, certolizumab pegol, golimumab, or biosimilars thereof.

In some embodiments, the alternative to anti-TNF therapy is selected from is selected from rituximab, sarilumab, tofacitinib citrate, leflunomide, vedolizumab, tocilizumab, anakinra, and abatacept.

In some embodiments, the disease, disorder, or condition is selected from rheumatoid arthritis, psoriatic arthritis, ankylosing spondylitis, Crohn's disease, ulcerative colitis, chronic psoriasis, hidradenitis suppurativa, multiple sclerosis, and juvenile idiopathic arthritis.

In some embodiments, the present disclosure provides a method of developing a classifier for stratifying subjects with respect to one or more therapeutic attributes comprising steps of: analyzing sequence data of RNA expressed in subjects representing at least two different categories with respect to at least one of the therapeutic attributes; assessing the presence of one or more single nucleotide polymorphisms (SNPs) from the sequence data; determining the presence of the one or more SNPs correlates with the at least one therapeutic attribute; and including the one or more SNPs in the classifier.

In some embodiments, the present disclosure provides, in a method of developing a classifier for stratifying subjects with respect to one or more therapeutic attributes by analyzing sequence data of RNA expressed in subjects representing at least two different categories with respect to at least one of the therapeutic attributes, the improvement that comprises: assessing presence of one or more single nucleotide polymorphisms (SNPs) from the sequence data; and determining the presence of the one or more SNPs correlates with the at least one therapeutic attribute; and including the one or more SNPs in the classifier.

In some embodiments, the one or more therapeutic attributes is selected from the group consisting of: risk of developing a particular disease, disorder or condition, likelihood of a particular outcome for a particular disease, disorder, or condition, likelihood of response to a particular therapy. In some embodiments, the one or more therapeutic attributes are the likelihood of response to a particular therapy. In some embodiments, the particular therapy is anti-TNF therapy. In some embodiments, assessing the presence of the one or more SNPs comprises comparing the sequence data of RNA to a reference human genome.

In some embodiments, the present disclosure provides a method of treating a subject suffering from an autoimmune disease, the method comprising steps of: (a) receiving, by a processor of a computing device, data corresponding to expression levels of each of one or more genes of the subject, where the genes are selected from Table 1; (b) automatically determining, by the processor, a classification of the subject as responsive or non-responsive to an anti-TNF therapy using the data received in step (a); and, optionally, (c) administering an alternative to anti-TNF therapy to the subject for treatment of the autoimmune disease if the subject is classified as non-responsive to the anti-TNF therapy; or administering the anti-TNF therapy if the subject is classified as responsive to the anti-TNF therapy.

In some embodiments, the processor in step (a) further receives data corresponding to at least one of: one or more clinical characteristics; or one or more single nucleotide polymorphisms (SNPs).

In some embodiments, the one or more clinical characteristics are selected from: body-mass index (BMI), gender, age, race, previous therapy treatment, disease duration, C-reactive protein (CRP) level, presence of anti-cyclic citrullinated peptide, presence of rheumatoid factor, patient global assessment, treatment response rate (e.g., ACR20, ACR50, ACR70), and combinations thereof. In some embodiments, the autoimmune disease is selected from rheumatoid arthritis, psoriatic arthritis, ankylosing spondylitis, Crohn's disease, ulcerative colitis, chronic psoriasis, hidradenitis suppurativa, and juvenile idiopathic arthritis. In some embodiments, the autoimmune disease is rheumatoid arthritis or ulcerative colitis.

In some embodiments, the alternative to anti-TNF therapy is selected from is selected from rituximab, sarilumab, tofacitinib citrate, leflunomide, vedolizumab, tocilizumab, anakinra, and abatacept. In some embodiments, the anti-TNF therapy is selected from infliximab, adalimumab, etanercept, certolizumab pegol, golimumab, or biosimilars thereof.

In some embodiments, step (b) comprises automatically determining said classification using a machine learning model. In some embodiments, the machine learning model is a random forest model.

In some embodiments, step (b) comprises automatically determining said classification without use of a clinical covariate classifier (CC). In some embodiments, step (b) comprises automatically determining said classification without use of a combined genomic-clinical classifier (GCC). In some embodiments, step (b) comprises automatically determining said classification without use of a clinical covariate classifier (CC) and without use of a combined genomic-clinical classifier (GCC).

In some embodiments, the present disclosure provides a method comprising the steps of: (a) receiving, by a processor of a computing device, data corresponding to expression levels of each of one or more genes of a subject suffering from an autoimmune disease (e.g., rheumatoid arthritis), said one or more genes comprising at least one member (e.g., one, two, three, four, five, six, seven, eight, nine, ten, or all eleven member(s)) selected from the group consisting of CORO2B, STOML2, CHMP7, SPINT2, CYSLTR2, SSNA1, IMPDH2, GOLGA1, SUOX, ARPC1A, and KLHDC3; (b) automatically determining, by the processor, a classification of the subject as non-responsive to an anti-TNF therapy using the data received in step (a); and, optionally, (c) prescribing and/or administering a second therapy (e.g., an alternative to the first therapy, e.g., an alternative to anti-TNF therapy) to the subject for treatment of the disease, thereby avoiding prescription of and/or administration of the first therapy to the subject.

In some embodiments the present disclosure provides a method comprising the steps of: (a) receiving, by a processor of a computing device, data corresponding to expression levels of each of one or more genes of a subject suffering from a disease (e.g., an autoimmune disease, e.g., rheumatoid arthritis), said one or more genes comprising at least one member (e.g., one, two, three, four, five, six, seven, eight, nine, ten, or all eleven member(s)) selected from the group consisting of CORO2B, STOML2, CHMP7, SPINT2, CYSLTR2, SSNA1, IMPDH2, GOLGA1, SUOX, ARPC1A, and KLHDC3; (b) automatically determining, by the processor, a classification of the subject as responsive to a first therapy (e.g., anti-TNF therapy) using the data received in step (a); and, optionally, (c) prescribing and/or administering the first therapy to the subject for treatment of the disease.

In some embodiments, step (b) comprises automatically determining said classification using a machine learning model (e.g., a random forest model). In some embodiments, step (b) comprises automatically determining said classification without use of a clinical covariate classifier (CC) and without use of a combined genomic-clinical classifier (GCC).

In some embodiments, the present disclosure provides a pipeline (e.g., a computer architecture pipeline) for analysis of genomic data (e.g., next gen RNA-seq data) of a subject (e.g., and for determination of a classification of said subject based on said genomic data), said pipeline comprising a plurality of modules, each module capable of being independently validated following an update of said module.

In some embodiments, said plurality of modules comprises one or more machine learning models.

In some embodiments, said plurality of modules comprises one or more known bioinformatics modules (e.g., RSEM and/or STAR) and one or more proprietary classification module(s).

In some embodiments, the present disclosure provides a method of classifying a subject suffering from an autoimmune disease as likely responsive or likely non-responsive to an anti-TNF therapy prior to any administration of said anti-TNF therapy to said subject, the method comprising steps of: (a) receiving, by a processor of a computing device, data corresponding to an expression level for the subject of each of one or more genes selected from the group consisting of the following:

| | |
|---|---|
| ARPC1A | LOC100506083 |
| ATAT1 | MORN2 |
| ATRAID | NGF |
| CD27 | RHOBTB1 |
| CHMP7 | RNGTT |
| COMMD5 | SETD9 |
| CORO2B | SNX8 |
| CYSLTR2 | SPINT2 |
| DNAJC7 | SPON2 |
| GOLGA1 | SSNA1 |
| HPCA | STOML2 |
| IMPDH2 | SUOX |
| KAT8 | TMEM258 |
| KLHDC3 | UBL7-AS1 | and (b) automatically determining, by the processor, a classification of the subject as responsive or non-responsive to the anti-TNF therapy using the data received in step (a).

In some embodiments, a method of classifying a subject suffering from an autoimmune disease as likely responsive or likely non-responsive to an anti-TNF therapy prior to any administration of said anti-TNF therapy to said subject, further comprises: (c) prescribing and/or administering an alternative to anti-TNF therapy to the subject for treatment of the autoimmune disease if the subject is classified in step (b) as non-responsive to the anti-TNF therapy; or administering the anti-TNF therapy to the subject if the subject is classified in step (b) as responsive to the anti-TNF therapy.

In some embodiments, the processor in step (a) further receives data corresponding to at least one of (i) and (ii) as follows: (i) one or more clinical characteristics of the subject; (ii) one or more single nucleotide polymorphisms (SNPs) for the subject.

In some embodiments, the processor in step (a) receives data corresponding to one or more clinical characteristics of the subject selected from the group consisting of body-mass index (BMI), gender, age, race, previous therapy treatment, disease duration, C-reactive protein (CRP) level, presence of anti-cyclic citrullinated peptide, presence of rheumatoid factor, patient global assessment, and treatment response rate (e.g., ACR20, ACR50, ACR70).

In some embodiments, the processor in step (a) receives data corresponding to one or more SNPs listed in Table 5.

In some embodiments, the autoimmune disease is a member selected from the group consisting of rheumatoid arthritis, psoriatic arthritis, ankylosing spondylitis, Crohn's disease, ulcerative colitis, chronic psoriasis, hidradenitis suppurativa, and juvenile idiopathic arthritis. In some embodiments, the autoimmune disease is rheumatoid arthritis or ulcerative colitis.

In some embodiments, the alternative to anti-TNF therapy comprises at least one member selected from the group consisting of rituximab, sarilumab, tofacitinib citrate, leflunomide, vedolizumab, tocilizumab, anakinra, and abatacept.

In some embodiments, the anti-TNF therapy comprises at least one member selected from the group consisting of infliximab, adalimumab, etanercept, certolizumab pegol, golimumab, and a biosimilar of any of the foregoing.

In some embodiments, the alternative to anti-TNF therapy does not comprise any member of the group consisting of infliximab, adalimumab, etanercept, certolizumab pegol, golimumab, and any biosimilar of any of the foregoing.

In some embodiments, step (b) comprises automatically determining said classification using a machine learning model. In some embodiments, the machine learning model is a random forest model.

In some embodiments, step (b) comprises automatically determining said classification without use of a clinical covariate classifier (CC). In some embodiments, step (b) comprises automatically determining said classification without use of a combined genomic-clinical classifier (GCC). In some embodiments, step (b) comprises automatically determining said classification without use of a clinical covariate classifier (CC) and without use of a combined genomic-clinical classifier (GCC).

In some embodiments, the present disclosure provides a method of classifying a subject suffering from an autoimmune disease as likely responsive or likely non-responsive to an anti-TNF therapy prior to any administration of said anti-TNF therapy to said subject, the method comprising the steps of: (a) receiving, by a processor of a computing device, data corresponding to an expression level of each of one or more genes of a subject suffering from the autoimmune disease said one or more genes comprising at least one member selected from the group consisting of CORO2B, STOML2, CHMP7, SPINT2, CYSLTR2, SSNA1, IMPDH2, GOLGA1, SUOX, ARPC1A, and KLHDC3; (b) automatically determining, by the processor, a classification of the subject as likely responsive or likely non-responsive to the anti-TNF therapy using the data received in step (a).

In some embodiments, a method of classifying a subject suffering from an autoimmune disease as likely responsive or likely non-responsive to an anti-TNF therapy prior to any administration of said anti-TNF therapy to said subject, further comprises: (c) prescribing and/or administering an alternative to anti-TNF therapy to the subject for treatment of the autoimmune disease if the subject is classified in step (b) as non-responsive to the anti-TNF therapy; or administering the anti-TNF therapy to the subject if the subject is classified in step (b) as responsive to the anti-TNF therapy.

In some embodiments, the autoimmune disease is rheumatoid arthritis.

In some embodiments, step (a) comprises receiving data corresponding to an expression level of each of at least two genes selected from the group consisting of CORO2B, STOML2, CHMP7, SPINT2, CYSLTR2, SSNA1, IMPDH2, GOLGA1, SUOX, ARPC1A, and KLHDC3.

In some embodiments, step (a) comprises receiving data corresponding to an expression level of each of at least three genes selected from the group consisting of CORO2B, STOML2, CHMP7, SPINT2, CYSLTR2, SSNA1, IMPDH2, GOLGA1, SUOX, ARPC1A, and KLHDC3.

In some embodiments, step (a) comprises receiving data corresponding to an expression level of each of at least five genes selected from the group consisting of CORO2B, STOML2, CHMP7, SPINT2, CYSLTR2, SSNA1, IMPDH2, GOLGA1, SUOX, ARPC1A, and KLHDC3.

In some embodiments, the processor in step (a) further receives data corresponding to at least one of (i) and (ii) as follows: (i) one or more clinical characteristics of the subject; (ii) one or more single nucleotide polymorphisms (SNPs) for the subject.

In some embodiments, the processor in step (a) receives data corresponding to one or more clinical characteristics of the subject selected from the group consisting of body-mass index (BMI), gender, age, race, previous therapy treatment, disease duration, C-reactive protein (CRP) level, presence of anti-cyclic citrullinated peptide, presence of rheumatoid factor, patient global assessment, and treatment response rate (e.g., ACR20, ACR50, ACR70).

In some embodiments, the processor in step (a) receives data corresponding to one or more SNPs listed in Table 5.

In some embodiments, the present disclosure provides a system for classifying a subject suffering from an autoimmune disease as likely responsive or likely non-responsive to an anti-TNF therapy prior to any administration of said anti-TNF therapy to said subject, the system comprising: a processor; and a memory having instructions thereon, the instructions, when executed by the processor, causing the processor to: (a) receive a set of data, said set of data comprising an expression level for the subject of each of one or more genes selected from the group consisting of the following:

| | |
|---|---|
| ARPC1A | LOC100506083 |
| ATAT1 | MORN2 |
| ATRAID | NGF |
| CD27 | RHOBTB1 |
| CHMP7 | RNGTT |
| COMMD5 | SETD9 |
| CORO2B | SNX8 |
| CYSLTR2 | SPINT2 |
| DNAJC7 | SPON2 |
| GOLGA1 | SSNA1 |
| HPCA | STOML2 |
| IMPDH2 | SUOX |
| KAT8 | TMEM258 |
| KLHDC3 | UBL7-AS1 | and (b) automatically determine a classification of the subject as responsive or non-responsive to the anti-TNF therapy using the set of data.

In some embodiments, the set of data further comprises data corresponding to at least one of (i) and (ii) as follows: (i) one or more clinical characteristics of the subject; (ii) one or more single nucleotide polymorphisms (SNPs) for the subject.

In some embodiments, the set of data comprises data corresponding to one or more clinical characteristics of the subject selected from the group consisting of body-mass index (BMI), gender, age, race, previous therapy treatment, disease duration, C-reactive protein (CRP) level, presence of anti-cyclic citrullinated peptide, presence of rheumatoid factor, patient global assessment, and treatment response rate (e.g., ACR20, ACR50, ACR70).

In some embodiments, the set of data comprises one or more SNPs listed in Table 5.

In some embodiments, the autoimmune disease is a member selected from the group consisting of rheumatoid arthritis, psoriatic arthritis, ankylosing spondylitis, Crohn's disease, ulcerative colitis, chronic psoriasis, hidradenitis suppurativa, and juvenile idiopathic arthritis. In some embodiments, the autoimmune disease is rheumatoid arthritis or ulcerative colitis. In some embodiments, the autoimmune disease is rheumatoid arthritis.

DEFINITIONS

Administration: As used herein, the term "administration" typically refers to the administration of a composition to a subject or system, for example to achieve delivery of an agent that is, or is included in or otherwise delivered by, the composition.

Agent: As used herein, the term "agent" refers to an entity (e.g., for example, a lipid, metal, nucleic acid, polypeptide, polysaccharide, small molecule, etc., or complex, combination, mixture or system [e.g., cell, tissue, organism] thereof), or phenomenon (e.g., heat, electric current or field, magnetic force or field, etc.).

Amino acid: As used herein, the term "amino acid" refers to any compound and/or substance that can be incorporated into a polypeptide chain, e.g., through formation of one or more peptide bonds. In some embodiments, an amino acid has the general structure $H_2N-C(H)(R)-COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. As used herein, the term "standard amino acid" refers to any of the twenty L-amino acids commonly found in naturally occurring peptides. "Nonstandard amino acid" refers to any amino acid, other than the standard amino acids, regardless of whether it is or can be found in a natural source. In some embodiments, an amino acid, including a carboxy- and/or amino-terminal amino acid in a polypeptide, can contain a structural modification as compared to the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared to the general structure. In some embodiments, such modification may, for example, alter the stability or the circulating half-life of a polypeptide containing the modified amino acid as compared to one containing an otherwise identical unmodified amino acid. In some embodiments, such modification does not significantly alter a relevant activity of a polypeptide containing the modified amino acid, as compared to one containing an otherwise identical unmodified amino acid. As will be clear from context, in some embodiments, the term "amino acid" may be used to refer to a free amino acid; in some embodiments it may be used to refer to an amino acid residue of a polypeptide, e.g., an amino acid residue within a polypeptide.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Antagonist: As used herein, the term "antagonist" may refer to an agent, or condition whose presence, level, degree, type, or form is associated with a decreased level or activity of a target. An antagonist may include an agent of any chemical class including, for example, small molecules, polypeptides, nucleic acids, carbohydrates, lipids, metals, and/or any other entity that shows the relevant inhibitory activity. In some embodiments, an antagonist may be a "direct antagonist" in that it binds directly to its target; in some embodiments, an antagonist may be an "indirect antagonist" in that it exerts its influence by means other than binding directly to its target; e.g., by interacting with a regulator of the target, so that the level or activity of the target is altered). In some embodiments, an "antagonist" may be referred to as an "inhibitor".

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; TransBodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., polyethylene glycol, etc.]).

Associated: Two events or entities are "associated" with one another, as that term is used herein, if the presence, level, degree, type and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Combination Therapy: As used herein, the term "combination therapy" refers to a clinical intervention in which a subject is simultaneously exposed to two or more therapeutic regimens (e.g. two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality. In some embodiments, combination therapy does not necessarily require that individual agents be administered together in a single composition (or even necessarily at the same time). In some embodiments, two or more therapeutic agents or modalities of a combination therapy are administered to a subject separately, e.g., in separate compositions, via separate administration routes (e.g., one agent orally and another agent intravenously), and/or at different time points. In some embodiments, two or more therapeutic agents may be administered together in a combination composition, or even in a combination compound (e.g., as part of a single chemical complex or covalent entity), via the same administration route, and/or at the same time.

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Corresponding to: As used herein, the phrase "corresponding to" refers to a relationship between two entities, events, or phenomena that share sufficient features to be reasonably comparable such that "corresponding" attributes are apparent. For example, in some embodiments, the term may be used in reference to a compound or composition, to designate the position and/or identity of a structural element in the compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids. For example, those skilled in the art will be aware of various sequence alignment strategies, including software programs such as, for example, BLAST, CS-BLAST, CUSASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that can be utilized, for example, to identify "corresponding" residues in polypeptides and/or nucleic acids in accordance with the present disclosure.

Dosing regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Improved, increased or reduced: As used herein, the terms "improved," "increased," or "reduced,", or grammatically comparable comparative terms thereof, indicate values that are relative to a comparable reference measurement. For example, in some embodiments, an assessed value achieved with an agent of interest may be "improved" relative to that obtained with a comparable reference agent. Alternatively or additionally, in some embodiments, an assessed value achieved in a subject or system of interest may be "improved" relative to that obtained in the same subject or system under different conditions (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc.).

Pharmaceutical composition: As used herein, the term "pharmaceutical composition" refers to an active agent, formulated together with one or more pharmaceutically acceptable carriers. In some embodiments, the active agent is present in unit dose amounts appropriate for administration in a therapeutic regimen to a relevant subject (e.g., in amounts that have been demonstrated to show a statistically significant probability of achieving a predetermined therapeutic effect when administered), or in a different, comparable subject (e.g., in a comparable subject or system that differs from the subject or system of interest in presence of one or more indicators of a particular disease, disorder or condition of interest, or in prior exposure to a condition or agent, etc.). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Reference: As used herein, the term "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Therapeutically effective amount: As used herein, the term "therapeutically effective amount" refers to an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder and/or condition. In some embodiments, a therapeutically effective amount is administered in a single dose; in some embodiments, multiple unit doses are required to deliver a therapeutically effective amount.

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature.

BRIEF DESCRIPTION OF THE DRAWINGS

FIG. 7A is a plot of features selected in top 100 vs. number of rounds of cross validation. FIG. 7C is a Receiver Operating Characteristic (ROC) curve showing the average area under the curve (AUC) for aggregate 20% withheld test sets throughout 100 rounds of cross validation. FIG. 7B illustrates predicted class probabilities of aggregate 20% withheld test set samples throughout 100 rounds of cross validation as dictated by each Random Forest model. FIG. 7D illustrates a principal component analysis of responders (red) and non-responders (black) to anti-TNF therapy when considering the 38 genes that ranked in the top 100 for 30 out of 100 rounds of cross validation.

FIG. 8A is an area under the curve (AUC) distribution of models built from both patients with and without seropositivity. FIG. 8B is an area under the curve (AUC) distribution of models built only with patients seropositive for RF and CCP. Baseline RNAseq data in seropositive samples, is best predictive of ACR50 outcome at 6 months for both male and female patients.

FIG. 9A illustrates a Receiver Operating Characteristic (ROC) curve showing average area under the curve (AUC) for aggregate 10% withheld cross validation repeated 10 times. FIG. 9B is a plot of negative predictive value (NPV) vs. true negative rate (TNR) for aggregate 10% withheld cross validation repeated 10 times. FIG. 9C is a plot of predicted probabilities for the aggregated validation set samples among responders and non-responders as dictated by the Random Forest model. FIG. 9D is a confusion matrix of aggregated validation set samples.

FIG. 12A illustrates a Receiver Operating Characteristic (ROC) curve showing area under the curve (AUC) for validation set samples. FIG. 12B is a plot of Negative Predictive Value (NPV) vs. True Negative Rate (TNR) for validation set samples. FIG. 12C is a plot of predicted class probability for each validation set sample as dictated by the Random Forest model. FIG. 12D is a confusion matrix related to validation of model for the prediction of response to anti-TNF therapy.

FIG. 13A illustrates a Receiver Operating Characteristic (ROC) curve showing area under the curve (AUC) for validation set samples. FIG. 13B is a plot of Negative Predictive Value (NPV) vs. True Negative Rate (TNR) for validation set samples. FIG. 13C is a plot of predicted class probability for each validation set sample as dictated by the Random Forest model. FIG. 13D is a confusion matrix related to validation of model among seropositive patients only (n=23) for the prediction of response to anti-TNF therapy.

DETAILED DESCRIPTION

Figure 1:
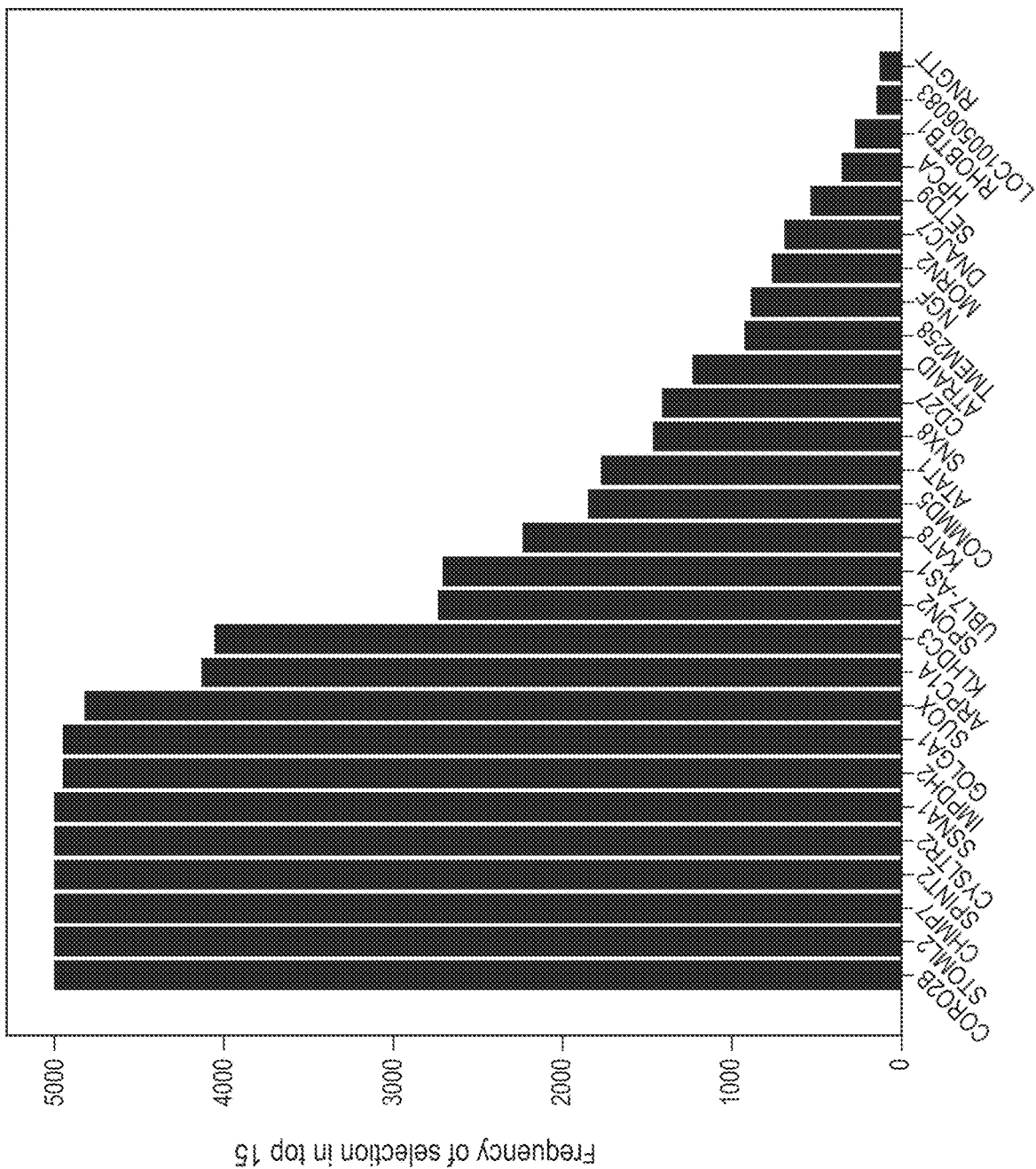
FIG. 1 is a graph of potential relative predictive value of the expression levels of particular genes for classification of subjects as responders to anti-TNF therapy.

Presented herein are systems and methods for the automated prediction of subject response to anti-TNF therapies. Also presented herein are modular systems for automated interpretation of genomic and/or multi-omic data.

(a) Provided Classifier(s)

The present disclosure provides a classifier and development of such a classifier that can identify (i.e., predict) which patients will or will not respond to a particular therapy. In some embodiments, a classifier is established to distinguish between responsive and non-responsive prior subjects who have received an anti-TNF therapy (e.g., a particular anti-TNF agent and/or regimen).

Among other things, the present disclosure encompasses the insight that expression level(s) for a certain set of genes, alone and in combination with one another, optionally coupled with certain clinical characteristics and/or with presence or absence of certain single nucleotide polymorphism(s), are useful for predicting response (e.g., one or more features of response) to anti-TNF therapy.

In some embodiments, the present disclosure provides a classifier that is or includes such gene expression level(s), clinical characteristic(s) and/or SNP(s), and demonstrates that it has been established to distinguish between subjects who do and who do not respond to anti-TNF therapy. In some embodiments, a provided classifier is established to distinguish, through retrospective analysis of historical (i.e., prior) subject population(s) who received anti-TNF therapy and whose responsiveness is known (e.g., was previously determined), between subjects (e.g., anti-TNF therapy naïve subjects) who are responsive or non-responsive to anti-TNF therapy. In some embodiments, a classifier that, when applied to such historical (i.e., prior) population(s) identifies at least 50% of non-responders within a cohort with at least 70% accuracy is considered "validated." In some embodiments, a classifier that, when applied to such historical (i.e., prior) population(s) identifies at least 60% of non-responders within a cohort with at least 70% accuracy is considered "validated." In some embodiments, a classifier that, when applied to such historical (i.e., prior) population(s) identifies at least 70% of non-responders within a cohort with at least 70% accuracy is considered "validated." In some embodiments, a classifier that, when applied to such historical (i.e., prior) population(s) identifies at least 80% of non-responders within a cohort with at least 70% accuracy is considered "validated." In some embodiments, a classifier that, when applied to such historical (i.e., prior) population(s) identifies at least 90% of non-responders within a cohort with at least 70% accuracy is considered "validated." In some embodiments, a classifier that, when applied to such historical (i.e., prior) population(s) identifies at least 99% of non-responders within a cohort with at least 70% accuracy is considered "validated."

In some embodiments, a classifier that, when applied to such historical (i.e., prior) population(s) identifies at least 50% of non-responders within a cohort with at least 80% accuracy is considered "validated." In some embodiments, a classifier that, when applied to such historical (i.e., prior) population(s) identifies at least 50% of non-responders within a cohort with at least 90% accuracy is considered "validated." In some embodiments, a classifier that, when applied to such historical (i.e., prior) population(s) identifies at least 50% of non-responders within a cohort with at least 99% accuracy is considered "validated."

In some embodiments, the present disclosure provides methods of treating subjects suffering from a disease, disorder, or condition, comprising administering an anti-TNF therapy to a subject(s) that has been determined through application of a provided classifier to be likely to respond to such anti-TNF therapy; alternatively or additionally, in some embodiments, the present disclosure provides methods of treating subjects suffering from a disease, disorder or condition, comprising withholding anti-TNF therapy, and/or administering an alternative to anti-TNF therapy to a subject(s) determined through application of a provided classifier to be unlikely to respond to such anti-TNF therapy.

In some embodiments, a provided classifier may be or comprise gene expression information for one or more genes. Alternatively or additionally, in some embodiments, a provided classifier may be or comprise presence or absence of one or more single nucleotide polymorphisms (SNP) and/or one or more clinical features or characteristics of a relevant subject.

In some embodiments, a classifier is developed by assessing each of the one or more genes whose expression levels significantly correlate (e.g., in a linear and/or non-linear manner) to clinical responsiveness or non-responsiveness; presence of the one or more SNPs; and at least one clinical characteristic.

In some embodiments, as described herein, a classifier is developed by retrospective analysis of one or more features (e.g., gene expression levels, presence or absence of one or more SNPs, etc.) of biological samples from patients (e.g., prior subjects) who have received anti-TNF therapy and have been determined to respond (i.e., are responders) or not to respond (i.e., are non-responders); alternatively or additionally, in some embodiments, a classifier is developed by retrospective analysis of one or more clinical characteristics of such patients, which may or may not involve assessment of any biological samples (and may be accomplished, for example, by reference to medical records). In some embodiments, all such patients have received the same anti-TNF therapy (optionally for the same or different periods of time); alternatively or additionally, in some embodiments, all such patients have been diagnosed with the same disease, disorder or condition. In some embodiments, patients whose biological samples are analyzed in the retrospective analysis had received different anti-TNF therapy (e.g., with a different anti-TNF agent and/or according to a different regimen);

alternatively or additionally, in some embodiments, patients whose biological samples are analyzed in the retrospective analysis have been diagnosed with different diseases, disorders, or conditions.

(i) Gene Expression

Typically, a gene expression aspect of a classifier as described herein is determined by assessing one or more genes whose expression levels significantly correlate (e.g., in a linear and/or non-linear manner) to clinical responsiveness or non-responsiveness; and at least one of: presence of one or more single nucleotide polymorphisms (SNPs) in an expressed sequence of the one or more genes; or at least one clinical characteristic of the responsive and non-responsive prior subjects. Genes whose expression levels show statistically significant differences between the responder and non-responder populations may be included in the gene response signature.

In some embodiments, the present disclosure embodies an insight that the source of a problem with certain prior efforts to identify or provide a classifier between responsive and non-responsive subjects is through comparison of gene expression levels in responder vs non-responder populations have emphasized and/or focused on (often solely on) genes that show the largest difference (e.g., greater than 2-fold change) in expression levels between the populations. The present disclosure appreciates that even genes those expression level differences are relatively small (e.g., less than 2-fold change in expression) provide useful information and are valuably included in a classifier in embodiments described herein.

Moreover, in some embodiments, the present disclosure embodies an insight that analysis of interaction patterns of genes whose expression levels show statistically significant differences (optionally including small differences) between responder and non-responder populations as described herein provides new and valuable information that materially improves the quality and predictive power of a classifier.

In some embodiments a provided classifier is or comprises a gene or set of genes that can be used to determine (e.g., whose expression level correlates with) whether a subject will or will not respond to a particular therapy (e.g., anti-TNF therapy). In some embodiments, a classifier is developed by assessing one or more genes whose expression levels significantly correlate (e.g., in a linear and/or non-linear manner) to clinical responsiveness or non-responsiveness; and at least one of: presence of one or more single nucleotide polymorphisms (SNPs); and at least one clinical characteristic of the responsive and non-responsive prior subjects.

In some embodiments, one or more genes for use in a classifier and/or for measuring gene expression are selected from genes in Table 1:

TABLE 1

| | |
|---|---|
| ARPC1A | LOC100506083 |
| ATAT1 | MORN2 |
| ATRAID | NGF |
| CD27 | RHOBTB1 |
| CHMP7 | RNGTT |
| COMMD5 | SETD9 |
| CORO2B | SNX8 |
| CYSLTR2 | SPINT2 |
| DNAJC7 | SPON2 |
| GOLGA1 | SSNA1 |
| HPCA | STOML2 |
| IMPDH2 | SUOX |
| KAT8 | TMEM258 |
| KLHDC3 | UBL7-AS1 |

In certain embodiments, gene expression levels of various subsets of the above-identified eleven identified genes (and/or the 17 additional genes shown in FIG. 1) are used (e.g., with or without weighting factors). For example, in certain embodiments, the classification model may be based on expression levels a subset of three, four, five, six, seven, eight, nine, or ten members of the set of eleven genes—CORO2B, STOML2, CHMP7, SPINT2, CYSLTR2, SSNA1, IMPDH2, GOLGA1, SUOX, ARPC1A, and KLHDC3—may be used, or, in certain embodiments, the classification model may be based on expression levels of a subset of the set of twenty-eight genes shown in FIG. 1. In certain embodiments, RNA sequencing (RNA-seq) data read counts of each of the genes in the classifier are used in the model. In certain embodiments, the RNA-seq read counts are provided as fragments per kilobase of exon per million reads (FPKMs).

Moreover, and surprisingly, the model based on gene expression levels of the set of eleven genes—CORO2B, STOML2, CHMP7, SPINT2, CYSLTR2, SSNA1, IMPDH2, GOLGA1, SUOX, ARPC1A, and KLHDC3—was found to be a better predictor of response/non-response to anti-TNF therapy than either a clinical covariate classifier (CC) or a combined genomic-clinical classifier (GCC).

In some embodiments, one, two, three, four, five, six, seven, eight, nine, ten, or all eleven genes of the set of eleven genes (CORO2B, STOML2, CHMP7, SPINT2, CYSLTR2, SSNA1, IMPDH2, GOLGA1, SUOX, ARPC1A, and KLHDC3) are measured to predict anti-TNF response. In some embodiments, one gene is measured. In some embodiments, two genes are selected. In some embodiments, three genes are selected. In some embodiments, four genes are selected. In some embodiments, five genes are selected. In some embodiments, six genes are selected. In some embodiments, seven genes are selected. In some embodiments, eight genes are selected. In some embodiments, nine genes are selected. In some embodiments, ten genes are selected. In some embodiments, eleven genes are selected. In some embodiments, more than eight genes are selected. In some embodiments, eight, nine, ten, or eleven genes are selected.

In some embodiments, a classification (i.e., a determination or prediction) of a subject as being responsive or non-responsive is determined using expression levels of one or more genes selected from CORO2B, STOML2, CHMP7, SPINT2, CYSLTR2, SSNA1, IMPDH2, GOLGA1, SUOX, ARPC1A, and KLHDC3. In some embodiments, the classification is determined using a machine learning model. In some embodiments, the machine learning model is a random forest model.

In some embodiments, provided methods determine classification of a subject as being a responder or non-responder without use of a clinical covariate classifier (CC). In some embodiments, provided methods determine classification of a subject as being a responder or non-responder without use of a combined genomic-clinical classifier (GCC). In some embodiments, provided methods determine classification of a subject as being a responder or non-responder without use of a clinical covariate classifier (CC) and without use of a combined genomic-clinical classifier (GCC).

In some embodiments, one or more genes for use in a classifier are selected from the group consisting of CORO2B, STOML2, CHMP7, SPINT2, CYSLTR2, SSNA1, IMPDH2, GOLGA1, SUOX, ARPC1A, and KLHDC3.

In some embodiments, a gene expression in a classifier can be identified using mRNA and/or protein expression datasets, for example as may be or have been prepared from validated biological data (e.g., biological data derived from publicly available databases such as Gene Expression Omnibus ("GEO")). In some embodiments, a classifier may be derived by comparing gene expression levels of known responsive and known non-responsive prior subjects to a specific therapy (e.g., anti-TNF therapy). In some embodiments, certain genes (i.e., signature genes) are selected from this cohort of gene expression data to be used in developing the classifier.

In some embodiments, signature genes are identified by methods analogous to those reported by Santolini, "A personalized, multiomics approach identifies genes involved in cardiac hypertrophy and heart failure," *Systems Biology and Applications*, (2018) 4:12; doi:10.1038/s41540-018-0046-3, which is incorporated herein by reference. In some embodiments, signature genes are identified by comparing gene expression levels of known responsive and non-responsive prior subjects and identifying significant changes between the two groups, wherein the significant changes can be large differences in expression (e.g., greater than 2-fold change), small differences in expression (e.g., less than 2-fold change), or both. In some embodiments, genes are ranked by significance of difference in expression. In some embodiments, significance is measured by Pearson correlation between gene expression and response outcome. In some embodiments, signature genes are selected from the ranking by significance of difference in expression. In some embodiments, the number of signature genes selected is less than the total number of genes analyzed. In some embodiments, 200 signature genes or less are selected. In some embodiments 100 genes or less are selected.

In some embodiments, signature genes are selected in conjunction with their location on a human interactome (HI), a map of protein-protein interactions. Use of the HI in this way encompasses a recognition that mRNA activity is dynamic and determines the actual over and under expression of proteins critical to understanding certain diseases. In some embodiments, genes associated with response to certain therapies (i.e., anti-TNF therapy) may cluster (i.e., form a cluster of genes) in discrete modules on the HI map. The existence of such clusters is associated with the existence of fundamental underlying disease biology. In some embodiments, a classifier is derived from signature genes selected from the cluster of genes on the HI map. Accordingly, in some embodiments, a classifier is derived from a cluster of genes associated with response to anti-TNF therapy on a human interactome map.

In some embodiments, genes associated with response to certain therapies exhibit certain topological properties when mapped onto a human interactome map. For example, in some embodiments, a plurality of genes associated with response to anti-TNF therapy and characterized by their position (i.e., topological properties, e.g., their proximity to one another) on a human interactome map.

In some embodiments, genes associated with response to certain therapies (i.e., anti-TNF therapy) may exist within close proximity to one another on the HI map. Said proximal genes, do not necessarily need to share fundamental underlying disease biology. That is, in some embodiments, proximal genes do not share significant protein interaction. Accordingly, in some embodiments, the classifier is derived from genes that are proximal on a human interactome map. In some embodiments, the classifier is derived from certain other topological features on a human interactome map.

In some embodiments, genes associated with response to certain therapies (i.e., anti-TNF therapy) may be determined by Diffusion State Distance (DSD) (see Cao, et al., *PLOS One*, 8(10): e76339 (Oct. 23, 2013)) when used in combination with the HI map.

In some embodiments, signature genes are selected by (1) ranking genes based on the significance of difference of expression of genes as compared to known responders and known non-responders; (2) selecting genes from the ranked genes and mapping the selected genes onto a human interactome map; and (3) selecting signature genes from the genes mapped onto the human interactome map.

In some embodiments, signature genes (e.g., selected from the Santolini method, or using various network topological properties including, but not limited to, clustering, proximity and diffusion-based methods) are provided to a probabilistic neural network to thereby provide (i.e., "train") the classifier. In some embodiments, the probabilistic neural network implements the algorithm proposed by D. F. Specht in "Probabilistic Neural Networks," *Neural Networks*, 3(1): 109-118 (1990), which is incorporated herein by reference. In some embodiments, the probabilistic neural network is written in the R-statistical language, and knowing a set of observations described by a vector of quantitative variables classifies observations into a given number of groups (e.g., responders and non-responders). The algorithm is trained with the data set of signature genes taken from known responders and non-responders and hypothesizes new observations that are provided. In some embodiments, the probabilistic neural network is one derived from the Comprehensive R Archive Network (CRAN). In some embodiments, signature genes are analyzed according to a Random Forest Model to provide a classifier.

(ii) Single Nucleotide Polymorphisms

The present disclosure further encompasses the insight that single nucleotide polymorphisms (SNPs) can be identified via RNA sequence data. That is, by comparison of RNA sequence data to a reference human genome, e.g., by mapping RNA sequence data to the GRCh38 human genome. Without being bound by theory, it is believed that the presence of SNPs that correlate to RNA sequences used in the classifier can facilitate identifying a subpopulation of subjects who respond or do not respond to certain therapies (e.g., anti-TNF therapies). That is, protein products of the discriminatory genes and SNP-containing RNAs can be analyzed using network medicine and pathway enrichment analyses. The proteins encoded by the discriminatory genes and SNP-containing RNAs included in the classifier can be overlaid on, for example, a map of the human interactome to help identify certain subpopulations of subjects by identifying certain sets of discriminatory genes.

In some embodiments, provided classifiers and methods of using such classifiers, incorporate an assessment related to single nucleotide polymorphisms (SNPs). In some embodiments, the present disclosure provides a method of developing a classifier for stratifying subjects with respect to one or more therapeutic attributes comprising steps of: analyzing sequence data of RNA expressed in subjects representing at least two different categories with respect to at least one of the therapeutic attributes; assessing the presence of one or more single nucleotide polymorphisms (SNPs) from the sequence data; determining the presence of the one or more SNPs correlates with the at least one therapeutic attribute; and including the one or more SNPs in the classifier.

In some embodiments, the present disclosure provides, in a method of developing a classifier for stratifying subjects with respect to one or more therapeutic attributes by analyzing sequence data of RNA expressed in subjects representing at least two different categories with respect to at least one of the therapeutic attributes, the improvement that comprises: assessing presence of one or more single nucleotide polymorphisms (SNPs) from the sequence data; and determining the presence of the one or more SNPs correlates with the at least one therapeutic attribute; and including presence of the one or more SNPs in the classifier.

In some embodiments, one or more SNPs are selected from:

| SNP |
|---|
| chr1.161644258 |
| chr1.2523811 |
| chr11.107967350 |
| chr17.38031857 |
| chr7.128580042 |
| rs10774624 |
| rs10985070 |
| rs11889341 |
| rs1571878 |
| rs1633360 |
| rs17668708 |
| rs1877030 |
| rs1893592 |
| rs1980422 |
| rs2228145 |
| rs2233424 |
| rs2236668 |
| rs2301888 |
| rs2476601 |
| rs3087243 |
| rs3218251 |
| rs331463 |
| rs34536443 |
| rs34695944 |
| rs4239702 |
| rs4272 |
| rs45475795 |
| rs508970 |
| rs5987194 |
| rs657075 |
| rs6715284 |
| rs706778 |
| rs72634030 |
| rs73013527 |
| rs73194058 |
| rs773125 |
| rs7752903 |
| rs8083786 |
| rs9653442 |

(iii) Clinical Characteristics

The classifier can also incorporate additional information in order to further improve predictive ability of the classifier to identify between responders and non-responders. For example, in some embodiments, a classifier is developed by assessing one or more genes whose expression levels significantly correlate (e.g., in a linear and/or non-linear manner) to clinical responsiveness or non-responsiveness; and at least one of presence of one or more single nucleotide polymorphisms (SNPs) in an expressed sequence of the one or more genes; or at least one clinical characteristic of the responsive and non-responsive prior subjects. That is, in some embodiments, a classifier is developed assessing by one or more genes whose expression levels significantly correlate (e.g., in a linear and/or non-linear manner) to clinical responsiveness or non-responsiveness and the presence of one or more single nucleotide polymorphisms (SNPs) in an expressed sequence of the one or more genes. In some embodiments, a classifier is developed assessing by one or more genes whose expression levels significantly correlate (e.g., in a linear and/or non-linear manner) to clinical responsiveness or non-responsiveness and at least one clinical characteristic of the responsive and non-responsive prior subjects.

The present disclosure further encompasses the insight that certain clinical characteristics (e.g., BMI, gender, age, and the like), can be incorporated into classifiers provided herein. In some embodiments, provided classifiers and methods of using such classifiers, incorporate an assessment related to clinical characteristics. In some embodiments, the present disclosure provides a method of developing a classifier for stratifying subjects with respect to one or more therapeutic attributes comprising steps of: analyzing sequence data of RNA expressed in subjects representing at least two different categories with respect to at least one of the therapeutic attributes; assessing the presence of one or more clinical characteristics; determining that expression related to said clinical characteristics correlate with the at least one therapeutic attribute; and including the one or more clinical characteristics in the classifier.

In some embodiments, at least one clinical characteristic is selected from: body-mass index (BMI), gender, age, race, previous therapy treatment, disease duration, C-reactive protein (CRP) level, presence of anti-cyclic citrullinated peptide, presence of rheumatoid factor, patient global assessment, treatment response rate (e.g., ACR20, ACR50, ACR70), and combinations thereof.

In some embodiments, a clinical characteristic is selected from:

| Clinical Characteristics |
|---|
| Age |
| Gender at birth |
| Duration of disease (in years) |
| Race (included white, asian, black, mixed race, Native American, Pacific Islander, and other) |
| History of fibromyalgia |
| History of chronic vascular disease (includes acute coronary syndrome, coronary artery disease, congestive heart failure, hypertension, myocardial infarction, peripheral arterial disease, stroke, unstable angina, cardiac arrest, revascularization procedure, and ventricular arrhythmia) |
| History of serious infection that led to hospitalization (includes infections of bursa or joint, cellulitis, sinusitis, diverticulitis, sepsis, pneumonia bronchitis gastro meningitis, urinary tract infection, upper respiratory infection, and tuberculosis) |
| History of cancer (includes breast, lung, skin, lymphoma but excludes non-melanoma skin) |
| BMI |
| Smoking status (includes never, previous or current) |
| Prednisone dose |
| DMARD dose |
| C-reactive protein level at baseline |
| DAS28-CRP at baseline |
| Swollen 28-joint count at baseline |
| Tender 28-joint count at baseline |
| Patient global assessment at baseline |
| Physician global assessment at baseline |
| CDAI at baseline |
| Modified health assessment questionnaire score at baseline |
| Patient pain assessment at baseline |
| EULAR response at baseline using DAS28-CRP (includes poor, moderate or good) |
| Anti-CCP status (positive or negative) |
| Anti-CCP titer at baseline |
| Rheumatoid factor status (positive or negative) |
| Rheumatoid factor titer at baseline |

(iv) Validating Classifiers

Alternatively or additionally, in some embodiments, a classifier can be trained in the probabilistic neural network using a cohort of known responders and non-responders using leave-one-out cross and/or k-fold cross validation. In some embodiments, such a process leaves one sample out (i.e., leave-one-out) of the analysis and trains the classifier only based on the remaining samples. In some embodiments, the updated classifier is then used to predict a probability of response for the sample that's left out. In some embodiments, such a process can be repeated iteratively, for example, until all samples have been left out once. In some embodiments, such a process randomly partitions a cohort of known responders and non-responders into k equal sizes groups. Of the k groups, a single group is retained as validation data for testing the model, and the remaining groups are used as training data. Such a process can be repeated k times, with each of the k groups being used exactly once as the validation data. In some embodiments, the outcome is a probability score for each sample in the training set. Such probability scores can correlate with actual response outcome. A Recursive Operating Curves (ROC) can be used to estimate the performance of the classifier. In some embodiments, an Area Under Curve (AUC) of about 0.6 or higher reflects a suitable validated classifier. In some embodiments, a Negative Predictive Value (NPV) of 0.9 reflects a suitable validated classifier. In some embodiments, a classifier can be tested in a completely independent (i.e., blinded) cohort to, for example, confirm the suitability (i.e., using leave-one-out and/or k-fold cross validation). Accordingly, in some embodiments, provided methods further comprise one or more steps of validating a classifier, for example, by assigning probability of response to a group of known responders and non-responders; and checking the classifier against a blinded group of responders and non-responders. The output of these processes is a trained classifier useful for establishing whether a subject will or will not respond to a particular therapy (e.g., anti-TNF therapy).

Accordingly, in some embodiments, the classifier is established to distinguish between responsive and non-responsive prior subjects who have received a type of therapy, e.g., anti-TNF therapy. This classifier can predict whether a subject will or will not respond to a given therapy. In some embodiments, the response and non-responsive prior subjects suffered from the same disease, disorder, or condition.

In some embodiments, genes of the subject are measured by at least one of a microarray, RNA sequencing, real-time quantitative reverse transcription PCR (qRT-PCR), bead array, ELISA, and protein expression.

In some embodiments, a classifier is validated using a cohort of subjects having previously been treated with anti-TNF therapy, but is independent from the cohort of subjects used to prepare the classifier. In some embodiments, the classifier is updated using gene expression data, SNP data, or clinical characteristics. In some embodiments, a classifier is considered "validated" when 90% or greater of non-responding subjects are predicted with 60% or greater accuracy within the validating cohort.

In some embodiments, the classifier predicts responsiveness of subjects with at least 60% accuracy predicting responsiveness across a population of at least 100 subjects. In some embodiments, the classifier predicts responsiveness of subjects with at least 60% accuracy across a population of at least 150 subjects. In some embodiments, the classifier predicts responsiveness of subjects with at least 60% accuracy across a population of at least 170 subjects. In some embodiments, the classifier predicts responsiveness of subjects with at least 60% accuracy across a population of at least 200 or more subjects.

In some embodiments, the classifier predicts responsiveness of subjects with at least 80% accuracy across a population of at least 100 subjects. In some embodiments, the classifier predicts responsiveness of subjects with at least 80% accuracy across a population of at least 150 subjects. In some embodiments, the classifier predicts responsiveness of subjects with at least 80% accuracy across a population of at least 170 subjects. In some embodiments, the classifier predicts responsiveness of subjects with at least 80% accuracy across a population of at least 200 or more subjects.

In some embodiments, the classifier predicts responsiveness of subjects with at least 90% accuracy across a population of at least 100 subjects. In some embodiments, the classifier predicts responsiveness of subjects with at least 90% accuracy across a population of at least 150 subjects. In some embodiments, the classifier predicts responsiveness of subjects with at least 90% accuracy across a population of at least 170 subjects. In some embodiments, the classifier predicts responsiveness of subjects with at least 90% accuracy across a population of at least 200 or more subjects.

(b) Detecting Gene Signature(s) and/or SNPs

Detecting gene signatures in a subject using a trained classifier is a routine matter for those of skill in the art. In other words, by first defining the gene signatures (from the classifier), a variety of methods can be used to determine whether a subject or group of subjects express the established gene signatures. For example, in some embodiments, a practitioner can obtain a blood or tissue sample from the subject prior to administering of therapy, and extract and analyze mRNA profiles from said blood or tissue sample. The analysis of mRNA profiles can be performed by any method known to those of skill in the art, including, but not limited gene arrays, RNA-sequencing, nanostring sequencing, real-time quantitative reverse transcription PCR (qRT-PCR), bead arrays, or enzyme-linked immunosorbent assay (ELISA). Accordingly, in some embodiments, the present disclosure provides methods of determining whether a subject is classified as a responder or non-responder, comprising measuring gene expression by at least one of a microarray, RNA sequencing, real-time quantitative reverse transcription PCR (qRT-PCR), bead array, and ELISA. In some embodiments, the present disclosure provides methods of determining whether a subject is classified as a responder or non-responder comprising measuring gene expression of a subject by RNA sequencing (i.e., RNAseq).

The present disclosure further encompasses the insight that single nucleotide polymorphisms (SNPs) can be identified via RNA sequence data. That is, by comparison of RNA sequence data to a reference human genome, e.g., by mapping RNA sequence data to the GRCh38 human genome. Without being bound by theory, it is believed that the presence of SNPs that correlate to RNA sequences used in the classifier can facilitate identifying a subpopulation of subjects who respond or do not respond to certain therapies (e.g., anti-TNF therapies). That is, protein products of the discriminatory genes and SNP-containing RNAs can be analyzed using network medicine and pathway enrichment analyses. The proteins encoded by the discriminatory genes and SNP-containing RNAs included in the classifier can be overlaid on, for example, a map of the human interactome to help identify certain subpopulations of subjects by identifying certain sets of discriminatory genes.

In some embodiments, gene expression is measured by subtracting background data, correcting for batch effects, and dividing by mean expression of housekeeping genes. See Eisenberg & Levanon, "Human housekeeping genes, revisited," *Trends in Genetics*, 29(10):569-574 (October 2013). In the context of microarray data analysis, background subtraction refers to subtracting the average fluorescent signal arising from probe features on a chip not complimentary to any mRNA sequence, i.e. signals that arise from non-specific binding, from the fluorescence signal intensity of each probe feature. The background subtraction can be performed with different software packages, such as Affymetrix® Gene Expression Console. Housekeeping genes are involved in basic cell maintenance and, therefore, are expected to maintain constant expression levels in all cells and conditions. The expression level of genes of interest, i.e., those in the response signature, can be normalized by dividing the expression level by the average expression level across a group of selected housekeeping genes. This housekeeping gene normalization procedure calibrates the gene expression level for experimental variability. Further, normalization methods such as robust multi-array average ("RMA") correct for variability across different batches of microarrays, are available in R packages recommended by either Illumina® and/or Affymetrix® array platforms. The normalized data is log transformed, and probes with low detection rates across samples are removed. Furthermore, probes with no available genes symbol or Entrez ID are removed from the analysis.

In some embodiments, the present disclosure provides a kit comprising a classifier established to distinguish between responsive and non-responsive prior subjects who have received anti-TNF therapy.

(c) Using Classifiers (i) Patient Stratification

Among other things, the present disclosure provides technologies for predicting responsiveness to anti-TNF therapies. In some embodiments, provided technologies exhibit consistency and/or accuracy across cohorts superior to previous methodologies.

Thus, the present disclosure provides technologies for patient stratification, defining and/or distinguishing between responder and non-responder populations. For example, in some embodiments, the present disclosure provides methods for treating subjects with anti-TNF therapy, which methods, in some embodiments, comprise a step of: administering the anti-TNF therapy to subjects who have been determined to be responsive via a classifier established to distinguish between responsive and non-responsive prior subjects who have received the anti-TNF therapy.

In some embodiments, the present disclosure provides a method of developing a classifier for stratifying subjects with respect to one or more therapeutic attributes comprising steps of: analyzing sequence data of RNA expressed in subjects representing at least two different categories with respect to at least one of the therapeutic attributes; assessing the presence of one or more single nucleotide polymorphisms (SNPs) from the sequence data; determining the presence of the one or more SNPs correlates with the at least one therapeutic attribute; and including the one or more SNPs in the classifier.

(ii) Therapy Monitoring

Further, the present disclosure provides technologies for monitoring therapy for a given subject or cohort of subjects. As a subject's gene expression level can change over time, it may, in some instances, be necessary or desirable to evaluate a subject at one or more points in time, for example, at specified and or periodic intervals.

In some embodiments, repeated monitoring under time permits or achieves detection of one or more changes in a subject's gene expression profile or characteristics that may impact ongoing treatment regimens. In some embodiments, a change is detected in response to which particular therapy administered to the subject is continued, is altered, or is suspended. In some embodiments, therapy may be altered, for example, by increasing or decreasing frequency and/or amount of administration of one or more agents or treatments with which the subject is already being treated. Alternatively or additionally, in some embodiments, therapy may be altered by addition of therapy with one or more new agents or treatments. In some embodiments, therapy may be altered by suspension or cessation of one or more particular agents or treatments.

To give but one example, if a subject is initially classified as responsive (because the subject's gene expression was determined, via classifier, to be associated with a disease, disorder, or condition), a given anti-TNF therapy can then be administered. At a given interval (e.g., every six months, every year, etc.), the subject can be tested again to ensure that they still qualify as "responsive" to a given anti-TNF therapy. In the event the gene expression levels for a given subject change over time, and the subject no longer expresses genes associated with the disease, disorder, or condition, or now expresses genes associated with non-responsiveness, the subject's therapy can be altered to suit the change in gene expression.

Accordingly, in some embodiments, the present disclosure provides methods of administering therapy to a subject previously established via classifier as responsive with anti-TNF therapy.

In some embodiments, the present disclosure provides methods further comprising determining, prior to the administering, that a subject is not a responder via a classifier; and administering a therapy alternative to anti-TNF therapy.

In some embodiments, genes of the subject are measured by at least one of a microarray, RNA sequencing, real-time quantitative reverse transcription PCR (qRT-PCR), bead array, ELISA, and protein expression.

In some embodiments, the subject suffers from a disease, disorder, or condition selected from rheumatoid arthritis, psoriatic arthritis, ankylosing spondylitis, Crohn's disease, ulcerative colitis, chronic psoriasis, hidradenitis suppurativa, multiple sclerosis, and juvenile idiopathic arthritis.

In some embodiments, the anti-TNF therapy is or comprises administration of infliximab, adalimumab, etanercept, certolizumab pegol, golimumab, or biosimilars thereof. In some embodiments, the anti-TNF therapy is or comprises administration of infliximab or adalimumab.

In some embodiments, the responsive and non-responsive prior subjects suffered from the same disease, disorder, or condition.

In some embodiments, the subjects to whom the anti-TNF therapy is administered are suffering from the same disease, disorder or condition as the prior responsive and non-responsive prior subjects.

In some embodiments, the disease, disorder, or condition is selected from rheumatoid arthritis, psoriatic arthritis, ankylosing spondylitis, Crohn's disease, ulcerative colitis, chronic psoriasis, hidradenitis suppurativa, multiple sclerosis, and juvenile idiopathic arthritis.

In some embodiments, the disease, disorder, or condition is rheumatoid arthritis.

In some embodiments, the disease, disorder, or condition is ulcerative colitis.

(d) Methods of Treatment

In some embodiments, a subject or population with respect to which anti-TNF therapy is administered, or from which anti-TNF therapy is withheld (and/or alternative therapy is administered) is one that is determined to exhibit a particular expression level one or more genes, and typically for a plurality of genes. In some embodiments, one or more genes is determined to have an expression level below a particular threshold; alternatively or additionally, in some embodiments, one or more genes is determined to have an expression level below a particular threshold. In some embodiments, a particular set of genes is determined to have a pattern of expression in which each is assessed relative to a particular threshold (and, e.g., is determined to be above, below, or comparable with such threshold).

In some embodiments, the present disclosure provides a method of treating subjects suffering from a disease, disorder, or condition comprising administering an alternative to anti-TNF therapy to a subject that has been determined to exhibit less than a particular expression level of one or more genes.

Accordingly, in some embodiments, the present disclosure provides a method comprising the steps of:

(a) receiving, by a processor of a computing device, data corresponding to expression levels of each of one or more genes of a subject suffering from an inflammatory disease (e.g., an autoimmune disorder, rheumatoid arthritis), said one or more genes comprising at least one member (e.g., one, two, three, four, five, six, seven, eight, nine, ten, or all eleven member(s)) selected from the group consisting of CORO2B, STOML2, CHMP7, SPINT2, CYSLTR2, SSNA1, IMPDH2, GOLGA1, SUOX, ARPC1A, and KLHDC3;

(b) automatically determining, by the processor, a classification of the subject as non-responsive to an anti-TNF therapy using the data received in step (a); and, optionally, (c) prescribing and/or administering a second therapy (e.g., an alternative to anti-TNF therapy) to the subject for treatment of the disease, thereby avoiding prescription of and/or administration of the first therapy to the subject.

In some embodiments, the present disclosure provides a method comprising the steps of:

(a) receiving, by a processor of a computing device, data corresponding to expression levels of each of one or more genes of a subject suffering from a disease (e.g., an autoimmune disease, e.g., rheumatoid arthritis), said one or more genes comprising at least one member (e.g., one, two, three, four, five, six, seven, eight, nine, ten, or all eleven member(s)) selected from the group consisting of CORO2B, STOML2, CHMP7, SPINT2, CYSLTR2, SSNA1, IMPDH2, GOLGA1, SUOX, ARPC1A, and KLHDC3;

(b) automatically determining, by the processor, a classification of the subject as responsive to a first therapy (e.g., anti-TNF therapy) using the data received in step (a); and, optionally, (c) prescribing and/or administering the first therapy to the subject for treatment of the disease.

In some embodiments, the present disclosure provides methods of administering the anti-TNF therapy to subjects who have been determined to be responsive via a classifier established to distinguish between responsive and non-responsive prior subjects who have received the anti-TNF therapy (i.e., wherein the classifier has been established, through retrospective analysis, to distinguish between those who did vs those who did not respond to anti-TNF therapy that they received); wherein the classifier that is developed by assessing: one or more genes whose expression levels significantly correlate (e.g., in a linear and/or non-linear manner) to clinical responsiveness or non-responsiveness; and at least one of: presence of one or more single nucleotide polymorphisms (SNPs) in an expressed sequence; and at least one clinical characteristic of the responsive and non-responsive prior subjects.

TNF-mediated disorders are currently treated by inhibition of TNF, and in particular by administration of an anti-TNF agent (i.e., by anti-TNF therapy). Examples of anti-TNF agents approved for use in the United States include monoclonal antibodies such as adalimumab (Humira®), certolizumab pegol (Cimiza®), infliximab (Remicade®), and decoy circulating receptor fusion proteins such as etanercept (Enbrel®). These agents are currently approved for use in treatment of indications, according to dosing regimens, as set forth below in Table 2:

TABLE 2

| Indication | Adalimumab[1] | Certolizumab Pegol[1] | Infliximab[2] | Etanercept[1] | Golimumab[1] | Golimumab[2] |
|---|---|---|---|---|---|---|
| Juvenile Idiopathic Arthritis | 10 kg (22 lbs) to <15 kg (33 lbs): 10 mg every other week 15 kg (33 lbs) to <30 kg (66 lbs): 20 mg every other week ≥30 kg (66 lbs): 40 mg every other week | N/A | N/A | 0.8 mg/kg weekly, with a maximum of 50 mg per week | N/A | N/A |
| Psoriatic Arthritis | 40 mg every other week | 400 mg initially and at week 2 and 4, followed by 200 mg every other week; for maintenance dosing, 400 mg every 4 weeks | 5 mg/kg at 0, 2 and 6 weeks, then every 8 weeks | 50 mg once weekly with or without methotrexate | 50 mg administered by subcutaneous injection once a month | N/A |
| Rheumatoid Arthritis | 40 mg every other week | 400 mg initially and at Weeks 2 and 4, followed by 200 mg every other week; for maintenance dosing, 400 mg every 4 weeks | In conjunction with methotrexate, 3 mg/kg at 0, 2 and 6 weeks, then every 8 weeks | 50 mg once weekly with or without methotrexate | 50 mg once a month | 2 mg/kg intravenous infusion over 30 minutes at weeks 0 and 4, then every 8 weeks |

TABLE 2-continued

| Indication | Adalimumab[1] | Certolizumab Pegol[1] | Infliximab[2] | Etanercept[1] | Golimumab[1] | Golimumab[2] |
|---|---|---|---|---|---|---|
| Ankylosing Spondylitis | 40 mg every other week | 400 mg (given as 2 subcutaneous injections of 200 mg each) initially and at weeks 2 and 4, followed by 200 mg every other week or 400 mg every 4 weeks | 5 mg/kg at 0, 2 and 6 weeks, then every 6 weeks | 50 mg once weekly | 50 mg administered by subcutaneous injection once a month | N/A |
| Adult Crohn's Disease | Initial dose (Day 1): 160 mg Second dose two weeks later (Day 15): 80 mg Two weeks later (Day 29): Begin a maintenance dose of 40 mg every other week | 400 mg initially and at Weeks 2 and 4 Continue with 400 mg every four weeks | 5 mg/kg at 0, 2 and 6 weeks, then every 8 weeks. | N/A | N/A | N/A |
| Pediatric Crohn's Disease | 17 kg (37 lbs) to <40 kg (88 lbs): Initial dose (Day 1): 80 mg Second dose two weeks later (Day 15): 40 mg Two weeks later (Day 29): Begin a maintenance dose of 20 mg every other week ≥40 kg (88 lbs): Initial dose (Day 1): 160 mg Second dose two weeks later (Day 15): 80 mg Two weeks later (Day 29): Begin a maintenance dose of 40 mg every other week | N/A | 5 mg/kg at 0, 2 and 6 weeks, then every 8 weeks. | N/A | N/A | N/A |
| Ulcerative Colitis | Initial dose (Day 1): 160 mg Second dose two weeks later (Day 15): 80 mg Two weeks later (Day 29): Begin a maintenance dose of 40 mg every other week | N/A | 5 mg/kg at 0, 2 and 6 weeks, then every 8 weeks. | N/A | N/A | N/A |
| Plaque Psoriasis | 80 mg initial dose; 40 mg every other week beginning one week after initial dose | N/A | N/A | 50 mg twice weekly for 3 months, followed by 50 mg once weekly | N/A | N/A |
| Hidradenitis Suppurativa | Initial dose (Day 1): 160 mg Second dose two weeks later (Day 15): 80 mg Third dose (Day 29) and subsequent doses: 40 mg every week | N/A | N/A | N/A | N/A | N/A |

TABLE 2-continued

| Indication | Adalimumab[1] | Certolizumab Pegol[1] | Infliximab[2] | Etanercept[1] | Golimumab[1] | Golimumab[2] |
|---|---|---|---|---|---|---|
| Uveitis | 80 mg initial dose; 40 mg every other week beginning one week after initial dose | N/A | N/A | N/A | N/A | N/A |

[1]Administered by subcutaneous injection.
[2]Administered by intravenous infusion.

The present disclosure provides technologies relevant to anti-TNF therapy, including those therapeutic regimens as set forth in Table 2. In some embodiments, the anti-TNF therapy is or comprises administration of infliximab (Remicade®), adalimumab (Humira®), certolizumab pegol (Cimiza®), etanercept (Enbrel®), or biosimilars thereof. In some embodiments, the anti-TNF therapy is or comprises administration of infliximab (Remicade®) or adalimumab (Humira®). In some embodiments, the anti-TNF therapy is or comprises administration of infliximab (Remicade®). In some embodiments, the anti-TNF therapy is or comprises administration of adalimumab (Humira®).

In some embodiments, the anti-TNF therapy is or comprises administration of a biosimilar anti-TNF agent. In some embodiments, the anti-TNF agent is selected from infliximab biosimilars such as CT-P13, BOW015, SB2, Inflectra, Renflexis, and Ixifi, adalimumab biosimilars such as ABP 501 (AMGEVITA™), Adfrar, and Hulio™ and etanercept biosimilars such as HD203, SB4 (Benepali®), GP2015, Erelzi, and Intacept.

In some embodiments, the present disclosure provides a method of treating subjects suffering from an autoimmune disorder, the method comprising a step of: administering an anti-TNF therapy to subjects who have been determined to be responsive via a classifier established to distinguish between responsive and non-responsive prior subjects in a cohort who have received the anti-TNF therapy; wherein the classifier is developed by assessing: one or more genes whose expression levels significantly correlate (e.g., in a linear and/or non-linear manner) to clinical responsiveness or non-responsiveness; at least one of: presence of one or more single nucleotide polymorphisms (SNPs) in an expressed sequence of the one or more genes; or at least one clinical characteristic of the responsive and non-responsive prior subjects; and wherein the classifier is validated by an independent cohort than the cohort who have received the anti-TNF therapy.

In some embodiments, data derived from subjects in the cohort who have received the anti-TNF therapy is of one type (e.g., microarray, RNAseq, etc.), and the data used to validate the classifier in the independent cohort is derived from a different type (e.g., microarray, RNAseq). Accordingly, some embodiments, the classifier is established using microarray analysis derived from the responsive and non-responsive prior subjects. In some embodiments, the classifier is validated using RNAseq data derived from the independent cohort.

As provided herein, gene expression levels of certain gene combinations, optionally coupled with certain clinical characteristics, can be used to determine whether a patient/subject does or does not respond to a particular therapy (e.g., an anti-TNF therapy). For example, in some embodiment, validated random forest model based on gene expression levels of a set of eleven genes—CORO2B, STOML2, CHMP7, SPINT2, CYSLTR2, SSNA1, IMPDH2, GOLGA1, SUOX, ARPC1A, and KLHDC3—achieved an area under curve (AUC) of 0.72, a negative predictive value (NPV) of 0.85, and a true negative rate (TNR) of 0.61 in the classification of subjects as responders to anti-TNF therapy. Without being bound by theory, it appears these genes are highly relevant to inflammatory processes, RA, autoimmunity and the mechanism of action of anti-TNF agents. The high NPV achieved is particularly valuable for identification of non-responders, important in the treatment of RA where drug side effects may be severe and where it may take a long time for LDA or remission to be achieved. For example, a rheumatologist may be able to accurately predict that a given subject suffering from RA will not respond to anti-TNF therapy, and thus be able to prescribe an alternative therapy instead, thereby allowing the subject to avoid the side effect risk of anti-TNF drugs and the delay caused by ineffective disease treatment.

In some embodiments, the subject suffers from a disease, disorder, or condition selected from rheumatoid arthritis, psoriatic arthritis, ankylosing spondylitis, Crohn's disease, ulcerative colitis, chronic psoriasis, hidradenitis suppurativa, and juvenile idiopathic arthritis.

In some embodiments, the anti-TNF therapy is or comprises administration of infliximab, adalimumab, etanercept, certolizumab pegol, golimumab, or biosimilars thereof. In some embodiments, the anti-TNF therapy is or comprises administration of infliximab or adalimumab.

In some embodiments, the therapy alternative to anti-TNF therapy is selected from rituximab (Rituxan®), sarilumab (Kevzara®), tofacitinib citrate (Xeljanz®), leflunomide) (Arava®, vedolizumab (Entyvio®), tocilizumab (Actemra®), anakinra (Kineret®), and abatacept (Orencia®).

In general, provided disclosures are useful in any context in which administration of anti-TNF therapy is contemplated or implemented. In some embodiments, provided technologies are useful in the diagnosis and/or treatment of subjects suffering from a disease, disorder, or condition associated with aberrant (e.g., elevated) TNF expression and/or activity. In some embodiments, provided technologies are useful in monitoring subjects who are receiving or have received anti-TNF therapy. In some embodiments, provided technologies identify whether a subject will or will not respond to a given anti-TNF therapy. In some embodiments, the provided technologies identify whether a subject will develop resistance to a given anti-TNF therapy.

(e) Diseases, Disorders or Conditions

In general, provided disclosures are useful in any context in which administration of anti-TNF therapy is contemplated or implemented. In some embodiments, provided technologies are useful in the diagnosis and/or treatment of subjects suffering from a disease, disorder, or condition associated with aberrant (e.g., elevated) TNF expression and/or activity. In some embodiments, provided technologies are useful in monitoring subjects who are receiving or have received anti-TNF therapy. In some embodiments, provided technologies identify whether a subject will or will not respond to a given anti-TNF therapy. In some embodiments, the provided technologies identify whether a subject will develop resistance to a given anti-TNF therapy.

Accordingly, the present disclosure provides technologies relevant to treatment of the various disorders related to TNF, including those listed in Table 2. In some embodiments, a subject is suffering from a disease, disorder, or condition selected from rheumatoid arthritis, psoriatic arthritis, ankylosing spondylitis, Crohn's disease (adult or pediatric), ulcerative colitis, inflammatory bowel disease, chronic psoriasis, plaque psoriasis, hidradenitis suppurativa, asthma, uveitis, and juvenile idiopathic arthritis. In some embodiments, the disease, disorder, or condition is rheumatoid arthritis. In some embodiments, the disease, disorder, or condition is psoriatic arthritis. In some embodiments, the disease, disorder, or condition is ankylosing spondylitis. In some embodiments, the disease, disorder, or condition is Crohn's disease. In some embodiments, the disease, disorder, or condition is adult Crohn's disease. In some embodiments, the disease, disorder, or condition is pediatric Crohn's disease. In some embodiments, the disease, disorder, or condition is inflammatory bowel disease. In some embodiments, the disease, disorder, or condition is ulcerative colitis. In some embodiments, the disease, disorder, or condition is chronic psoriasis. In some embodiments, the disease, disorder, or condition is plaque psoriasis. In some embodiments, the disease, disorder, or condition is hidradenitis suppurativa. In some embodiments, the disease, disorder, or condition is asthma. In some embodiments, the disease, disorder, or condition is uveitis. In some embodiments, the disease, disorder, or condition is juvenile idiopathic arthritis.

In some embodiments, the disease, disorder or condition is granuloma annulare, necrobiosis lipoidica, hiradenitis suppurativa, pyoderma gangrenossum, Sweet's syndrome, subcorneal pustular dermatosis, systemic lupus erythematosus, scleroderma, dermatomyositis, Behcet's disease, acute/chronic graft versus host disease, pityriasis rubra pilaris, Sjorgren's syndrome, Wegener's granulomatosis, polymyalgia rheumatic, dermatomyositis, and pyoderma gangrenosum.

Further, as noted, the present disclosure provides technologies that allow practitioners to reliably and consistently predict response in a cohort of subjects. In particular, for example, the rate of response for some anti-TNF therapies is less than 35% within a given cohort of subjects. The provided technologies allow for prediction of greater than 65% accuracy within a cohort of subjects a response rate (i.e., whether certain subjects will or will not respond to a given therapy). In some embodiments, the methods and systems described herein predict 65% or greater the subjects that are responders (i.e., will respond to anti-TNF therapy) within a given cohort. In some embodiments, the methods and systems described herein predict 70% or greater the subjects that are responders within a given cohort. In some embodiments, the methods and systems described herein predict 80% or greater the subjects that are responders within a given cohort. In some embodiments, the methods and systems described herein predict 90% or greater the subjects that are responders within a given cohort. In some embodiments, the methods and systems described herein predict 100% the subjects that are responders within a given cohort. In some embodiments, the methods and systems described herein predict 65% or greater the subjects that are non-responders (i.e., will not respond to anti-TNF therapy) within a given cohort. In some embodiments, the methods and systems described herein predict 70% or greater the subjects that are non-responders within a given cohort. In some embodiments, the methods and systems described herein predict 80% or greater the subjects that are non-responders within a given cohort. In some embodiments, the methods and systems described herein predict 90% or greater the subjects that are non-responders within a given cohort. In some embodiments, the methods and systems described herein predict 100% of the subjects that are non-responders within a given cohort.

(f) Pipeline Analysis

Also described herein is a pipeline for analysis of genomic data with a modular architecture that allows for traceability and V&V testing/documentation required of clinical software, yet flexible to allow for updates of components over time. Next generation sequencing (NGS) of DNA and RNA (RNAseq) is a rapidly evolving field, with improvements to the bioinformatics algorithms and components regularly becoming available. This is in conflict with the standard IVD software which is traditionally locked down and validated. Any modification to the software necessitates extensive reverification and revalidation. In certain embodiments, the pipeline described herein allows for use of existing state of the art bioinformatics modules, e.g. RSEM, STAR, which are algorithms written in R, to be assembled in a pipeline together with one or more proprietary algorithms. Each module is "encapsulated" in a wrapper. Each component of the pipeline may be verified independently. The full pipeline would be verified and the system, with use of wet-lab generated data, would be validated. If any component of the pipeline were to be updated in the future, e.g. RSEM, STAR or one or more of the proprietary algorithms, then a facile V&V could be completed by verifying the upgraded component, verifying the system with the upgraded component, and reanalysis of previously generated wet lab data.

Figure 2:
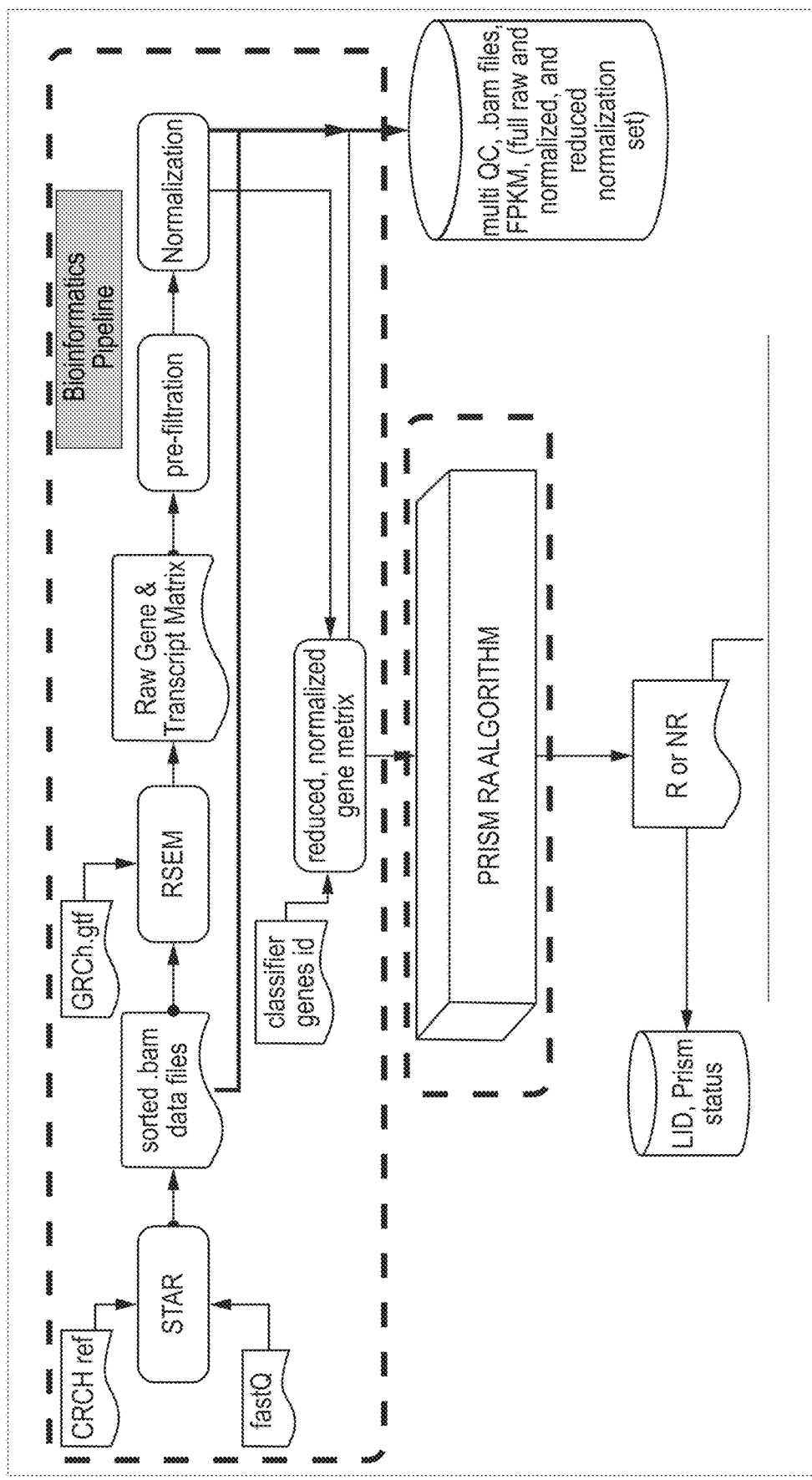
FIG. 2 is an illustration of an example embodiment incorporating (in the Red Box) a RNAseq bioinformatics pipeline, and (in the Blue Box), an exemplary proprietary algorithm (e.g., in this example, the PrismRA® algorithm).
Figure 3:
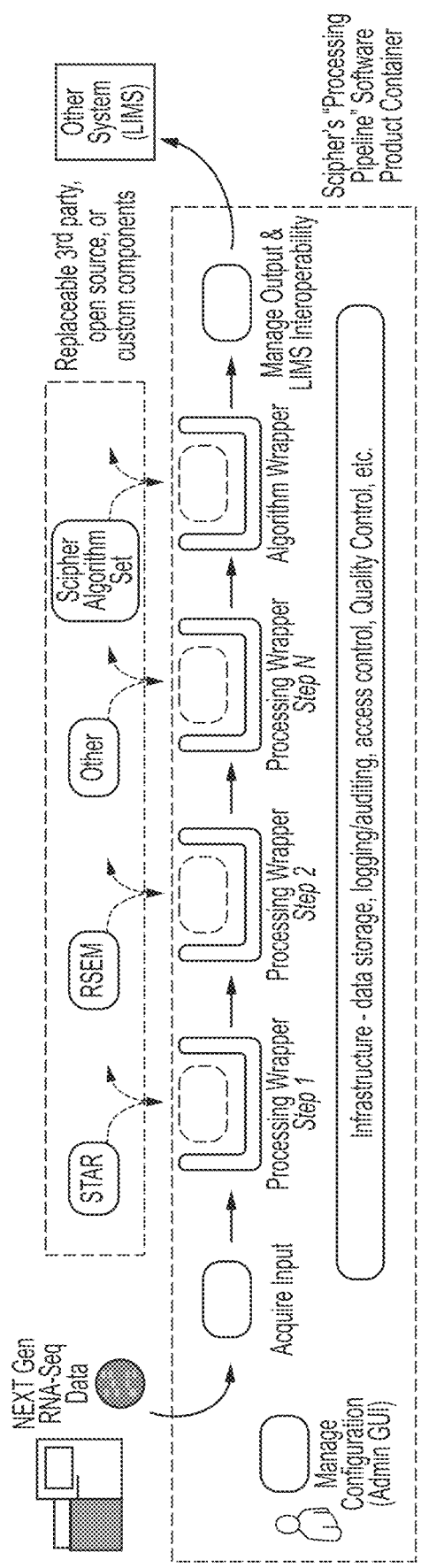
FIG. 3 is an illustrative pipeline for modular processing of RNA-seq data for use in classification (e.g., diagnostics, identification of responsiveness to particular treatment, and other applications).

FIG. 2 depicts an illustrative embodiment of the RNA-seq bioinformatics pipeline, as it can be used to produce input for a proprietary classification algorithm—in this example, a proprietary algorithm that produces a classification result of R (responder to a particular therapy) or NR (non-responder to the therapy). Other kinds of classification may be performed.

Figure 4:
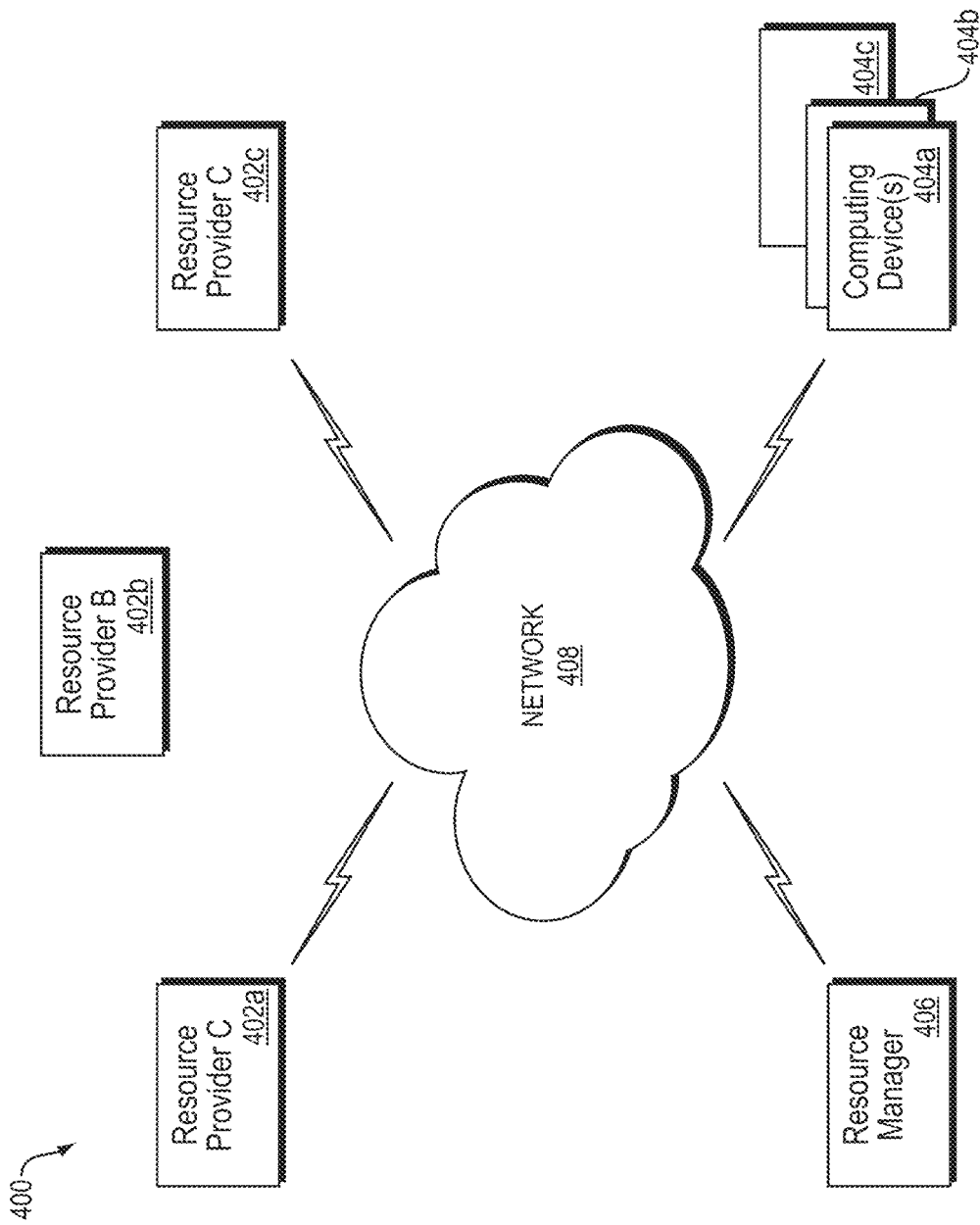
FIG. 4 is an example network environment and computing devices for use in various embodiments.

As illustrated in the exemplary embodiment in FIG. 2:
1. RNAseq bioinformatics pipeline
   a. The application reads fastq file and patient identifier and returns a structured text report featuring the same patient identifier along with a series of attributes values (format may be, for example, XML, JSON, or other options).
   b. The input files are fastq text data file (~30M reads on average, ~1.4G file size per file).
   c. The procedure starting from fastq input file to the final report includes:
      i. the alignment of the fastq short reads records to a reference genome assembly (Human Genome Assembly GRCh37 or GRCh38) with the Spliced Transcripts Alignment to a Reference (STAR) aligner [Dobin et al., 2013]
      ii. the quantification of transcript abundance with the RNA-Seq by Expectation-Maximization (RSEM) software package (Li and Wewey, 2011).

iii. Optional normalization by custom method
2. PrismRA® algorithm (illustrative proprietary algorithm)
   a. The modeling of a set binary outcomes w.r.t. the input data matrix produced in the prior step with an R package. This R package will feature dependencies to other packages, including glmnet, beanplots, pROC and samr.
3. QC tracking and triggers
   a. In addition to the final text report, the application can write and read intermediary QC reports whose values trigger different behavior of the software.
   b. The QC reports are generated from fastq file with the FastQC package (which requires the Picard BAM/SAM Libraries) and from BAM files with the RNA-SeQC package.
4. Data Traceability, Security, Privacy, Compliance
   a. Results are fully traceable to all inputs and processes.
   b. Data privacy and security: e.g., 21 CFR Part 11, HIPAA and ISO27001 Security compliance; GDPR compliance.
   c. Stability:
      i. The software is insulated from automatic package updates.
      ii. The software is portable, e.g., within a container that can be deployed on premise or on a private cloud As shown in FIG. 4, an implementation of a network environment 400 for use in providing systems, methods, and architectures as described herein is shown and described. In brief overview, referring now to FIG. 4, a block diagram of an exemplary cloud computing environment 400 is shown and described. The cloud computing environment 400 may include one or more resource providers 402a, 402b, 402c (collectively, 402). Each resource provider 402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 402 may be connected to any other resource provider 402 in the cloud computing environment 400. In some implementations, the resource providers 402 may be connected over a computer network 408. Each resource provider 402 may be connected to one or more computing device 404a, 404b, 404c (collectively, 404), over the computer network 408.

The cloud computing environment 400 may include a resource manager 406. The resource manager 406 may be connected to the resource providers 402 and the computing devices 404 over the computer network 408. In some implementations, the resource manager 406 may facilitate the provision of computing resources by one or more resource providers 402 to one or more computing devices 404. The resource manager 406 may receive a request for a computing resource from a particular computing device 404. The resource manager 406 may identify one or more resource providers 402 capable of providing the computing resource requested by the computing device 404. The resource manager 406 may select a resource provider 402 to provide the computing resource. The resource manager 406 may facilitate a connection between the resource provider 402 and a particular computing device 404. In some implementations, the resource manager 406 may establish a connection between a particular resource provider 402 and a particular computing device 404. In some implementations, the resource manager 406 may redirect a particular computing device 404 to a particular resource provider 402 with the requested computing resource.

Figure 5:
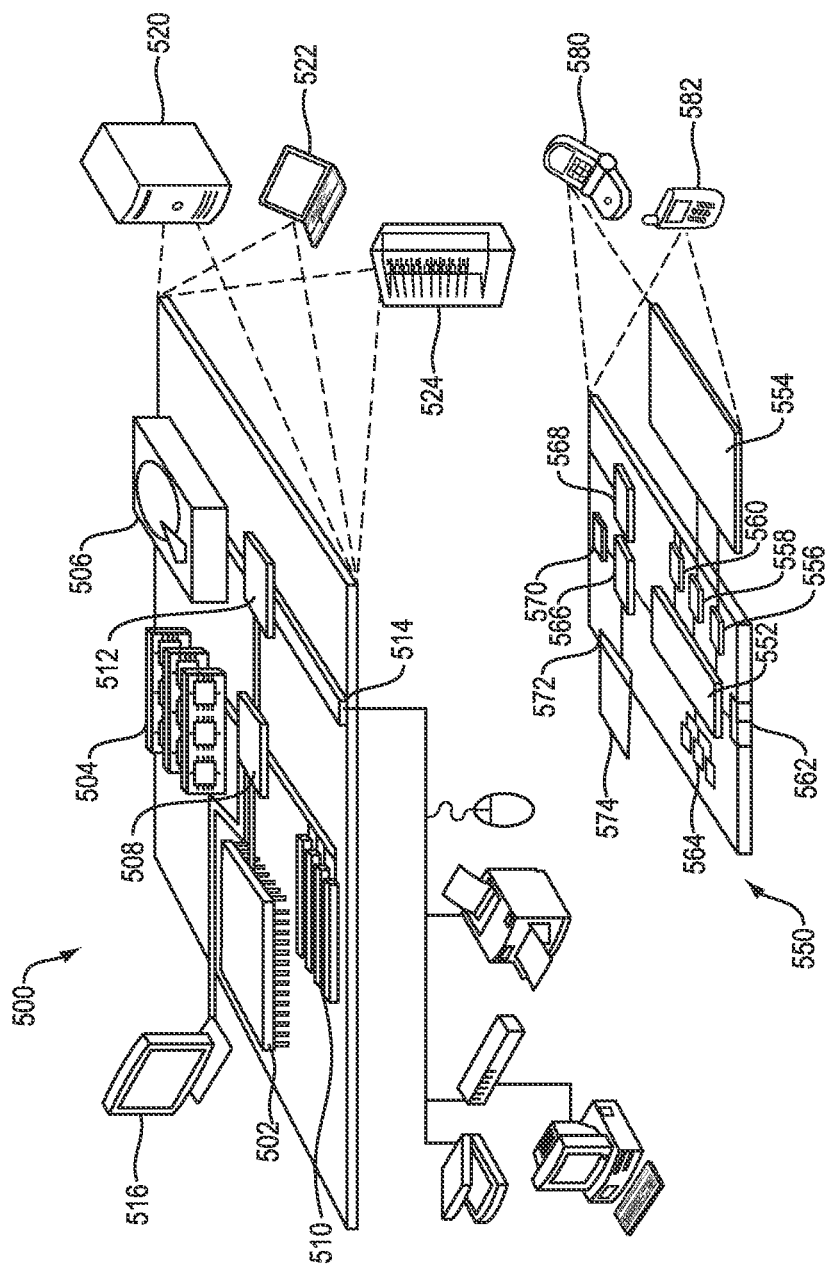
FIG. 5 shows an example of a computing device 500 and a mobile computing device 550 that can be used to implement the techniques described in this disclosure.

FIG. 5 shows an example of a computing device 500 and a mobile computing device 550 that can be used to implement the techniques described in this disclosure. The computing device 500 is intended to represent various forms of digital computers, such as laptops, desktops, workstations, personal digital assistants, servers, blade servers, mainframes, and other appropriate computers. The mobile computing device 550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 500 includes a processor 502, a memory 504, a storage device 506, a high-speed interface 508 connecting to the memory 504 and multiple high-speed expansion ports 510, and a low-speed interface 512 connecting to a low-speed expansion port 514 and the storage device 506. Each of the processor 502, the memory 504, the storage device 506, the high-speed interface 508, the high-speed expansion ports 510, and the low-speed interface 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as a display 516 coupled to the high-speed interface 508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 504 stores information within the computing device 500. In some implementations, the memory 504 is a volatile memory unit or units. In some implementations, the memory 504 is a non-volatile memory unit or units. The memory 504 may also be another form of computer-readable medium, such as a magnetic or optical disk.

The storage device 506 is capable of providing mass storage for the computing device 500. In some implementations, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 502), perform one or more methods, such as those described above. The instructions can also be stored by one or more storage devices such as computer- or machine-readable mediums (for example, the memory 504, the storage device 506, or memory on the processor 502).

The high-speed interface 508 manages bandwidth-intensive operations for the computing device 500, while the low-speed interface 512 manages lower bandwidth-intensive operations. Such allocation of functions is an example only. In some implementations, the high-speed interface 508 is coupled to the memory 504, the display 516 (e.g., through a graphics processor or accelerator), and to the high-speed expansion ports 510, which may accept various expansion cards (not shown). In the implementation, the low-speed interface 512 is coupled to the storage device 506 and the low-speed expansion port 514. The low-speed expansion port 514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. In addition, it may be implemented in a personal computer such as a laptop computer 522. It may also be implemented as part of a rack server system 524. Alternatively, components from the computing device 500 may be combined with other components in a mobile device (not shown), such as a mobile computing device 550. Each of such devices may contain one or more of the computing device 500 and the mobile computing device 550, and an entire system may be made up of multiple computing devices communicating with each other.

The mobile computing device 550 includes a processor 552, a memory 564, an input/output device such as a display 554, a communication interface 566, and a transceiver 568, among other components. The mobile computing device 550 may also be provided with a storage device, such as a micro-drive or other device, to provide additional storage. Each of the processor 552, the memory 564, the display 554, the communication interface 566, and the transceiver 568, are interconnected using various buses, and several of the components may be mounted on a common motherboard or in other manners as appropriate.

The processor 552 can execute instructions within the mobile computing device 550, including instructions stored in the memory 564. The processor 552 may be implemented as a chipset of chips that include separate and multiple analog and digital processors. The processor 552 may provide, for example, for coordination of the other components of the mobile computing device 550, such as control of user interfaces, applications run by the mobile computing device 550, and wireless communication by the mobile computing device 550.

The processor 552 may communicate with a user through a control interface 558 and a display interface 556 coupled to the display 554. The display 554 may be, for example, a TFT (Thin-Film-Transistor Liquid Crystal Display) display or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may provide communication with the processor 552, so as to enable near area communication of the mobile computing device 550 with other devices. The external interface 562 may provide, for example, for wired communication in some implementations, or for wireless communication in other implementations, and multiple interfaces may also be used.

The memory 564 stores information within the mobile computing device 550. The memory 564 can be implemented as one or more of a computer-readable medium or media, a volatile memory unit or units, or a non-volatile memory unit or units. An expansion memory 574 may also be provided and connected to the mobile computing device 550 through an expansion interface 572, which may include, for example, a SIMM (Single In Line Memory Module) card interface. The expansion memory 574 may provide extra storage space for the mobile computing device 550, or may also store applications or other information for the mobile computing device 550. Specifically, the expansion memory 574 may include instructions to carry out or supplement the processes described above, and may include secure information also. Thus, for example, the expansion memory 574 may be provide as a security module for the mobile computing device 550, and may be programmed with instructions that permit secure use of the mobile computing device 550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 552), perform one or more methods, such as those described above. The instructions can also be stored by one or more storage devices, such as one or more computer- or machine-readable mediums (for example, the memory 564, the expansion memory 574, or memory on the processor 552). In some implementations, the instructions can be received in a propagated signal, for example, over the transceiver 568 or the external interface 562.

The mobile computing device 550 may communicate wirelessly through the communication interface 566, which may include digital signal processing circuitry where necessary. The communication interface 566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 568 using a radio-frequency. In addition, short-range communication may occur, such as using a Bluetooth®, Wi-Fi™, or other such transceiver (not shown). In addition, a GPS (Global Positioning System) receiver module 570 may provide additional navigation- and location-related wireless data to the mobile computing device 550, which may be used as appropriate by applications running on the mobile computing device 550.

The mobile computing device 550 may also communicate audibly using an audio codec 560, which may receive spoken information from a user and convert it to usable digital information. The audio codec 560 may likewise generate audible sound for a user, such as through a speaker, e.g., in a handset of the mobile computing device 550. Such sound may include sound from voice telephone calls, may include recorded sound (e.g., voice messages, music files, etc.) and may also include sound generated by applications operating on the mobile computing device 550.

The mobile computing device 550 may be implemented in a number of different forms, as shown in the figure. For example, it may be implemented as a cellular telephone 580. It may also be implemented as part of a smart-phone 582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. In view of the structure, functions and apparatus of the systems and methods described here, in some implementations.

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are provided for the convenience of the reader—the presence and/or placement of a header is not intended to limit the scope of the subject matter described herein.

(g) Exemplary Embodiments

The following numbered embodiments, while non-limiting, are exemplary of certain aspects of the disclosure:

Embodiment 1. A method of treating subjects suffering from an autoimmune disorder, the method comprising a step of:
administering an anti-TNF therapy to subjects who have been determined to be responsive via a classifier established to distinguish between responsive and non-responsive prior subjects in a cohort who have received the anti-TNF therapy;
wherein the classifier is developed by assessing:
one or more genes whose expression levels significantly correlate (e.g., in a linear and/or non-linear manner) to clinical responsiveness or non-responsiveness;

at least one of:
  presence of one or more single nucleotide polymorphisms (SNPs) in an expressed sequence of the one or more genes; or
  at least one clinical characteristic of the responsive and non-responsive prior subjects; and
wherein the classifier is validated by an independent cohort than the cohort who have received the anti-TNF therapy.

Embodiment 2. The method of Embodiment 1, wherein the classifier predicts responsiveness of subjects with at least 90% accuracy across a population of at least 170 subjects.

Embodiment 3. The method of Embodiments 1 or 2, wherein the one or more genes are characterized by their topological properties when mapped on a human interactome map.

Embodiment 4. The method of any one of Embodiments 1-3, wherein the SNPs are identified in reference to a human genome.

Embodiment 5. The method of any one of Embodiments 1-4, wherein the classifier is developed by assessing each of:
  the one or more genes whose expression levels significantly correlate (e.g., in a linear and/or non-linear manner) to clinical responsiveness or non-responsiveness;
presence of the one or more SNPs; and the at least one clinical characteristic.

Embodiment 6. The method of any one of Embodiments 1-5, wherein the one or more genes are selected from:

| | |
|---|---|
| ARPC1A | LOC100506083 |
| ATAT1 | MORN2 |
| ATRAID | NGF |
| CD27 | RHOBTB1 |
| CHMP7 | RNGTT |
| COMMD5 | SETD9 |
| CORO2B | SNX8 |
| CYSLTR2 | SPINT2 |
| DNAJC7 | SPON2 |
| GOLGA1 | SSNA1 |
| HPCA | STOML2 |
| IMPDH2 | SUOX |
| KAT8 | TMEM258 |
| KLHDC3 | UBL7-AS1 |

Embodiment 7. The method of any one of Embodiments 1-6, wherein the at least one clinical characteristic is selected from: body-mass index (BMI), gender, age, race, previous therapy treatment, disease duration, C-reactive protein level, presence of anti-cyclic citrullinated peptide, presence of rheumatoid factor, patient global assessment, treatment response rate (e.g., ACR20, ACR50, ACR70), and combinations thereof Embodiment 8. The method of any one of Embodiments 1-6, wherein the classifier identifies at least 40% of subjects within a population that are non-responsive with at least 90% accuracy, wherein the population comprises at least 170 subjects.

Embodiment 9. The method of any one of Embodiments 1-8, wherein the anti-TNF therapy comprises administration of infliximab, adalimumab, etanercept, certolizumab pegol, golimumab, or biosimilars thereof.

Embodiment 10. The method of any one of Embodiments 1-9, wherein the disease, disorder, or condition is selected from rheumatoid arthritis, psoriatic arthritis, ankylosing spondylitis, Crohn's disease, ulcerative colitis, chronic psoriasis, hidradenitis suppurativa, multiple sclerosis, and juvenile idiopathic arthritis.

Embodiment 11. The method of any one of Embodiments 1-10, wherein the classifier is established using microarray analysis derived from the responsive and non-responsive prior subjects.

Embodiment 12. The method of any one of Embodiments 1-11, wherein the classifier is validated using RNAseq data derived from the independent cohort.

Embodiment 13. The method of any one of Embodiments 1-12, wherein the SNPs are selected from Table 5.

Embodiment 14. A method of administering a therapy to a subject suffering from an autoimmune disease, the method comprising
  administering the therapy to subjects who have been classified as responsive or non-responsive via a classifier established to distinguish between responsive and non-responsive prior subjects in a cohort who have received the anti-TNF therapy;
  wherein, if the subject is classified as responsive by the classifier, administering an anti-TNF therapy; and if the subject is classified as non-responsive by the classifier, administering an alternative to anti-TNF therapy; and
the classifier is developed by assessing:
  one or more genes whose expression levels significantly correlate (e.g., in a linear and/or non-linear manner) to clinical responsiveness or non-responsiveness;
at least one of:
  presence of one or more single nucleotide polymorphisms (SNPs) in an expressed sequence of the one or more genes; or
  at least one clinical characteristic of the responsive and non-responsive prior subjects; and
the classifier is validated by an independent cohort than the cohort who have received the anti-TNF therapy.

Embodiment 15. The method of Embodiment 14, wherein the classifier predicts responsiveness of subjects with at least 90% accuracy across a population of at least 170 subjects.

Embodiment 16. The method of Embodiment 15, wherein the classifier is developed by assessing each of:
  the one or more genes whose expression levels significantly correlate (e.g., in a linear and/or non-linear manner) to clinical responsiveness or non-responsiveness;
  presence of the one or more SNPs; and
  the at least one clinical characteristic.

Embodiment 17. The method of any one of Embodiments 14-16, wherein the at least one clinical characteristic is selected from: body-mass index (BMI), gender, age, race, previous therapy treatment, disease duration, C-reactive protein level, presence of anti-cyclic citrullinated peptide, presence of rheumatoid factor, patient global assessment, treatment response rate (e.g., ACR20, ACR50, ACR70), and combinations thereof.

Embodiment 18. The method of any one of Embodiments 14-17, wherein the anti-TNF therapy comprises administration of infliximab, adalimumab, etanercept, certolizumab pegol, golimumab, or biosimilars thereof.

Embodiment 19. The method of any one of Embodiments 14-18, wherein the alternative to anti-TNF therapy is selected from is selected from rituximab, sarilumab, tofacitinib citrate, leflunomide, vedolizumab, tocilizumab, anakinra, and abatacept.

Embodiment 20. The method of Embodiment 19, wherein the disease, disorder, or condition is selected from rheumatoid arthritis, psoriatic arthritis, ankylosing spondylitis, Crohn's disease, ulcerative colitis, chronic psoriasis, hidradenitis suppurativa, multiple sclerosis, and juvenile idiopathic arthritis.

Embodiment 21. A method of developing a classifier for stratifying subjects with respect to one or more therapeutic attributes comprising steps of:
analyzing sequence data of RNA expressed in subjects representing at least two different categories with respect to at least one of the therapeutic attributes;
assessing the presence of one or more single nucleotide polymorphisms (SNPs) from the sequence data;
determining the presence of the one or more SNPs correlates with the at least one therapeutic attribute; and
including the one or more SNPs in the classifier.

Embodiment 22. The method of Embodiment 21, wherein the one or more therapeutic attributes is selected from the group consisting of: risk of developing a particular disease, disorder or condition, likelihood of a particular outcome for a particular disease, disorder, or condition, likelihood of response to a particular therapy.

Embodiment 23. The method of Embodiments 21 or 22, wherein the one or more therapeutic attributes are the likelihood of response to a particular therapy.

Embodiment 24. The method of any one of Embodiments 21-23, wherein the particular therapy is anti-TNF therapy.

Embodiment 25. In a method of developing a classifier for stratifying subjects with respect to one or more therapeutic attributes by analyzing sequence data of RNA expressed in subjects representing at least two different categories with respect to at least one of the therapeutic attributes, the improvement that comprises:
assessing presence of one or more single nucleotide polymorphisms (SNPs) from the sequence data; and
determining the presence of the one or more SNPs correlates with the at least one therapeutic attribute; and
including the one or more SNPs in the classifier.

Embodiment 26. The method of Embodiment 25, wherein the one or more therapeutic attributes is selected from the group consisting of: risk of developing a particular disease, disorder or condition, likelihood of a particular outcome for a particular disease, disorder, or condition, likelihood of response to a particular therapy.

Embodiment 27. The method of Embodiments 25 or 26, wherein the one or more therapeutic attributes are the likelihood of response to a particular therapy.

Embodiment 28. The method of any one of Embodiments 25-27, wherein the particular therapy is anti-TNF therapy.

Embodiment 29. The method of any one of Embodiments 25-28, wherein assessing the presence of the one or more SNPs comprises comparing the sequence data of RNA to a reference human genome.

Embodiment 30. A method of treating a subject suffering from an autoimmune disease, the method comprising steps of:
(a) receiving, by a processor of a computing device, data corresponding to expression levels of each of one or more genes of the subject, where the genes are selected from Table 1;
(b) automatically determining, by the processor, a classification of the subject as responsive or non-responsive to an anti-TNF therapy using the data received in step (a); and, optionally,
(c) administering an alternative to anti-TNF therapy to the subject for treatment of the autoimmune disease if the subject is classified as non-responsive to the anti-TNF therapy; or administering the anti-TNF therapy if the subject is classified as responsive to the anti-TNF therapy.

Embodiment 31. The method of Embodiment 30, wherein the processor in step (a) further receives data corresponding to at least one of:
one or more clinical characteristics; or
one or more single nucleotide polymorphisms (SNPs).

Embodiment 32. The method of Embodiments 30 or 31, wherein the one or more clinical characteristics are selected from: body-mass index (BMI), gender, age, race, previous therapy treatment, disease duration, C-reactive protein (CRP) level, presence of anti-cyclic citrullinated peptide, presence of rheumatoid factor, patient global assessment, treatment response rate (e.g., ACR20, ACR50, ACR70), and combinations thereof.

Embodiment 33. The method of any one of Embodiments 30-32, wherein the autoimmune disease is selected from rheumatoid arthritis, psoriatic arthritis, ankylosing spondylitis, Crohn's disease, ulcerative colitis, chronic psoriasis, hidradenitis suppurativa, and juvenile idiopathic arthritis.

Embodiment 34. The method of any one of Embodiments 30-33, wherein the autoimmune disease is rheumatoid arthritis or ulcerative colitis.

Embodiment 35. The method of any one of Embodiments 30-34, wherein the alternative to anti-TNF therapy is selected from is selected from rituximab, sarilumab, tofacitinib citrate, leflunomide, vedolizumab, tocilizumab, anakinra, and abatacept.

Embodiment 36. The method of any one of Embodiments 30-34, wherein the anti-TNF therapy is selected from infliximab, adalimumab, etanercept, certolizumab pegol, golimumab, or biosimilars thereof.

Embodiment 37. The method of any one of Embodiments 30-36, wherein step (b) comprises automatically determining said classification using a machine learning model.

Embodiment 38. The method of Embodiment 37, wherein the machine learning model is a random forest model.

Embodiment 39. The method of any one of Embodiments 30-38, wherein step (b) comprises automatically determining said classification without use of a clinical covariate classifier (CC).

Embodiment 40. The method of any one of Embodiments 30-38, wherein step (b) comprises automatically determining said classification without use of a combined genomic-clinical classifier (GCC).

Embodiment 41. The method of any one of Embodiments 30-38, wherein step (b) comprises automatically determining said classification without use of a clinical covariate classifier (CC) and without use of a combined genomic-clinical classifier (GCC).

Embodiment 42. A method comprising the steps of:
(a) receiving, by a processor of a computing device, data corresponding to expression levels of each of one or more genes of a subject suffering from an autoimmune disease (e.g., rheumatoid arthritis), said one or more genes comprising at least one member (e.g., one, two, three, four, five, six, seven, eight, nine, ten, or all eleven member(s)) selected from the group consisting of CORO2B, STOML2, CHMP7, SPINT2, CYSLTR2, SSNA1, IMPDH2, GOLGA1, SUOX, ARPC1A, and KLHDC3;
(b) automatically determining, by the processor, a classification of the subject as non-responsive to an anti-TNF therapy using the data received in step (a); and, optionally, (c) prescribing and/or administering a second therapy (e.g., an alternative to the first therapy, e.g., an alternative to anti-TNF therapy) to the subject for treatment of the disease, thereby avoiding prescription of and/or administration of the first therapy to the subject.

Embodiment 43. A method comprising the steps of:
 (a) receiving, by a processor of a computing device, data corresponding to expression levels of each of one or more genes of a subject suffering from a disease (e.g., an autoimmune disease, e.g., rheumatoid arthritis), said one or more genes comprising at least one member (e.g., one, two, three, four, five, six, seven, eight, nine, ten, or all eleven member(s)) selected from the group consisting of CORO2B, STOML2, CHMP7, SPINT2, CYSLTR2, SSNA1, IMPDH2, GOLGA1, SUOX, ARPC1A, and KLHDC3;
 (b) automatically determining, by the processor, a classification of the subject as responsive to a first therapy (e.g., anti-TNF therapy) using the data received in step (a); and, optionally,
 (c) prescribing and/or administering the first therapy to the subject for treatment of the disease.

Embodiment 44. The method of Embodiments 42 or 43, wherein step (b) comprises automatically determining said classification using a machine learning model (e.g., a random forest model).

Embodiment 45. The method of any one of Embodiments 43 to 44, wherein step (b) comprises automatically determining said classification without use of a clinical covariate classifier (CC) and without use of a combined genomic-clinical classifier (GCC).

Embodiment 46. A pipeline (e.g., a computer architecture pipeline) for analysis of genomic data (e.g., next gen RNA-seq data) of a subject (e.g., and for determination of a classification of said subject based on said genomic data), said pipeline comprising a plurality of modules, each module capable of being independently validated following an update of said module.

Embodiment 47. The pipeline of Embodiment 46, wherein said plurality of modules comprises one or more machine learning models.

Embodiment 48. The pipeline of Embodiment 46 or 47, wherein said plurality of modules comprises one or more known bioinformatics modules (e.g., RSEM and/or STAR) and one or more proprietary classification module(s).

Embodiment 49. A method of classifying a subject suffering from an autoimmune disease as likely responsive or likely non-responsive to an anti-TNF therapy prior to any administration of said anti-TNF therapy to said subject, the method comprising steps of:
 (a) receiving, by a processor of a computing device, data corresponding to an expression level for the subject of each of one or more genes selected from the group consisting of the following:

| | |
|---|---|
| ARPC1A | LOC100506083 |
| ATAT1 | MORN2 |
| ATRAID | NGF |
| CD27 | RHOBTB1 |
| CHMP7 | RNGTT |
| COMMD5 | SETD9 |
| CORO2B | SNX8 |
| CYSLTR2 | SPINT2 |
| DNAJC7 | SPON2 |
| GOLGA1 | SSNA1 |
| HPCA | STOML2 |
| IMPDH2 | SUOX |
| KAT8 | TMEM258 |
| KLHDC3 | UBL7-AS1; | and
 (b) automatically determining, by the processor, a classification of the subject as responsive or non-responsive to the anti-TNF therapy using the data received in step (a).

Embodiment 50. The method of Embodiment 49, further comprising:
 (c) prescribing and/or administering an alternative to anti-TNF therapy to the subject for treatment of the autoimmune disease if the subject is classified in step (b) as non-responsive to the anti-TNF therapy; or administering the anti-TNF therapy to the subject if the subject is classified in step (b) as responsive to the anti-TNF therapy.

Embodiment 51. The method of Embodiment 49 or 50, wherein the processor in step (a) further receives data corresponding to at least one of (i) and (ii) as follows:
(i) one or more clinical characteristics of the subject;
(ii) one or more single nucleotide polymorphisms (SNPs) for the subject.

Embodiment 52. The method of any one of Embodiments 49 to 51, wherein the processor in step (a) receives data corresponding to one or more clinical characteristics of the subject selected from the group consisting of body-mass index (BMI), gender, age, race, previous therapy treatment, disease duration, C-reactive protein (CRP) level, presence of anti-cyclic citrullinated peptide, presence of rheumatoid factor, patient global assessment, and treatment response rate (e.g., ACR20, ACR50, ACR70).

Embodiment 53. The method of any one of Embodiments 49 to 52, wherein the processor in step (a) receives data corresponding to one or more SNPs listed in Table 5.

Embodiment 54. The method of any one of Embodiments 49 to 53, wherein the autoimmune disease is a member selected from the group consisting of rheumatoid arthritis, psoriatic arthritis, ankylosing spondylitis, Crohn's disease, ulcerative colitis, chronic psoriasis, hidradenitis suppurativa, and juvenile idiopathic arthritis.

Embodiment 55. The method of any one of Embodiments 49 to 54, wherein the autoimmune disease is rheumatoid arthritis or ulcerative colitis.

Embodiment 56. The method of any one of Embodiments 49 to 55, wherein the alternative to anti-TNF therapy comprises at least one member selected from the group consisting of rituximab, sarilumab, tofacitinib citrate, leflunomide, vedolizumab, tocilizumab, anakinra, and abatacept.

Embodiment 57. The method of any one of Embodiments 49 to 55, wherein the anti-TNF therapy comprises at least one member selected from the group consisting of infliximab, adalimumab, etanercept, certolizumab pegol, golimumab, and a biosimilar of any of the foregoing.

Embodiment 58. The method of any one of Embodiments 44 to 52, wherein the alternative to anti-TNF therapy does not comprise any member of the group consisting of infliximab, adalimumab, etanercept, certolizumab pegol, golimumab, and any biosimilar of any of the foregoing.

Embodiment 59. The method of any one of Embodiments 49 to 58, wherein step (b) comprises automatically determining said classification using a machine learning model.

Embodiment 60. The method of Embodiment 59, wherein the machine learning model is a random forest model.

Embodiment 61. The method of any one of Embodiments 49 to 60, wherein step (b) comprises automatically determining said classification without use of a clinical covariate classifier (CC).

Embodiment 62. The method of any one of Embodiments 49 to 60, wherein step (b) comprises automatically determining said classification without use of a combined genomic-clinical classifier (GCC).

Embodiment 63. The method of any one of Embodiments 49 to 60, wherein step (b) comprises automatically determining said classification without use of a clinical covariate classifier (CC) and without use of a combined genomic-clinical classifier (GCC).

Embodiment 64. A method of classifying a subject suffering from an autoimmune disease as likely responsive or likely non-responsive to an anti-TNF therapy prior to any administration of said anti-TNF therapy to said subject, the method comprising the steps of:
(a) receiving, by a processor of a computing device, data corresponding to an expression level of each of one or more genes of a subject suffering from the autoimmune disease said one or more genes comprising at least one member selected from the group consisting of CORO2B, STOML2, CHMP7, SPINT2, CYSLTR2, SSNA1, IMPDH2, GOLGA1, SUOX, ARPC1A, and KLHDC3;
(b) automatically determining, by the processor, a classification of the subject as likely responsive or likely non-responsive to the anti-TNF therapy using the data received in step (a).

Embodiment 65. The method of Embodiment 64, further comprising:
(c) prescribing and/or administering an alternative to anti-TNF therapy to the subject for treatment of the autoimmune disease if the subject is classified in step (b) as non-responsive to the anti-TNF therapy; or administering the anti-TNF therapy to the subject if the subject is classified in step (b) as responsive to the anti-TNF therapy Embodiment 66. The method of Embodiment 64 or 65, wherein the autoimmune disease is rheumatoid arthritis.

Embodiment 67. The method of any one of Embodiments 64 to 66, wherein step (a) comprises receiving data corresponding to an expression level of each of at least two genes selected from the group consisting of CORO2B, STOML2, CHMP7, SPINT2, CYSLTR2, SSNA1, IMPDH2, GOLGA1, SUOX, ARPC1A, and KLHDC3.

Embodiment 68. The method of any one of Embodiments 64 to 66, wherein step (a) comprises receiving data corresponding to an expression level of each of at least three genes selected from the group consisting of CORO2B, STOML2, CHMP7, SPINT2, CYSLTR2, SSNA1, IMPDH2, GOLGA1, SUOX, ARPC1A, and KLHDC3.

Embodiment 69. The method of any one of Embodiments 64 to 66, wherein step (a) comprises receiving data corresponding to an expression level of each of at least five genes selected from the group consisting of CORO2B, STOML2, CHMP7, SPINT2, CYSLTR2, SSNA1, IMPDH2, GOLGA1, SUOX, ARPC1A, and KLHDC3.

Embodiment 70. The method of any one of Embodiments 64 to 69, wherein the processor in step (a) further receives data corresponding to at least one of (i) and (ii) as follows:
(i) one or more clinical characteristics of the subject;
(ii) one or more single nucleotide polymorphisms (SNPs) for the subject.

Embodiment 71. The method of any one of Embodiments 64 to 70, wherein the processor in step (a) receives data corresponding to one or more clinical characteristics of the subject selected from the group consisting of body-mass index (BMI), gender, age, race, previous therapy treatment, disease duration, C-reactive protein (CRP) level, presence of anti-cyclic citrullinated peptide, presence of rheumatoid factor, patient global assessment, and treatment response rate (e.g., ACR20, ACR50, ACR70).

Embodiment 72. The method of any one of Embodiments 64 to 71, wherein the processor in step (a) receives data corresponding to one or more SNPs listed in Table 5.

Embodiment 73. A system for classifying a subject suffering from an autoimmune disease as likely responsive or likely non-responsive to an anti-TNF therapy prior to any administration of said anti-TNF therapy to said subject, the system comprising:
a processor; and
a memory having instructions thereon, the instructions, when executed by the processor, causing the processor to:
(a) receive a set of data, said set of data comprising an expression level for the subject of each of one or more genes selected from the group consisting of the following:

| | |
|---|---|
| ARPC1A | LOC100506083 |
| ATAT1 | MORN2 |
| ATRAID | NGF |
| CD27 | RHOBTB1 |
| CHMP7 | RNGTT |
| COMMD5 | SETD9 |
| CORO2B | SNX8 |
| CYSLTR2 | SPINT2 |
| DNAJC7 | SPON2 |
| GOLGA1 | SSNA1 |
| HPCA | STOML2 |
| IMPDH2 | SUOX |
| KAT8 | TMEM258 |
| KLHDC3 | UBL7-AS1; | and
(b) automatically determine a classification of the subject as responsive or non-responsive to the anti-TNF therapy using the set of data.

Embodiment 74. The system of Embodiment 73, wherein the set of data further comprises data corresponding to at least one of (i) and (ii) as follows:
(i) one or more clinical characteristics of the subject;
(ii) one or more single nucleotide polymorphisms (SNPs) for the subject.

Embodiment 75. The system of Embodiment 74, wherein the set of data comprises data corresponding to one or more clinical characteristics of the subject selected from the group consisting of body-mass index (BMI), gender, age, race, previous therapy treatment, disease duration, C-reactive protein (CRP) level, presence of anti-cyclic citrullinated peptide, presence of rheumatoid factor, patient global assessment, and treatment response rate (e.g., ACR20, ACR50, ACR70).

Embodiment 76. The system of Embodiment 74 or 75, wherein the set of data comprises one or more SNPs listed in Table 5.

Embodiment 77. The system of any one of Embodiments 74 to 76, wherein the autoimmune disease is a member selected from the group consisting of rheumatoid arthritis, psoriatic arthritis, ankylosing spondylitis, Crohn's disease, ulcerative colitis, chronic psoriasis, hidradenitis suppurativa, and juvenile idiopathic arthritis.

Embodiment 78. The system of any one of Embodiments 74 to 76, wherein the autoimmune disease is rheumatoid arthritis or ulcerative colitis.

Embodiment 79. The system of any one of Embodiments 74 to 76, wherein the autoimmune disease is rheumatoid arthritis.

EXEMPLIFICATION

Example 1

Introduction

Autoimmune diseases such as RA collectively affect millions of patients and their treatments represent a significant component of overall healthcare expenditure and thus require attention in order to improve patient outcome Autoimmune diseases can be divided into two groups of organ-specific and systemic autoimmunity. Rheumatoid diseases including rheumatoid arthritis (RA) belong to the systemic autoimmune diseases which primarily, manifests in synovial joints and eventually causes irreversible destruction of tendons, cartilage, and bone. Although there is no current cure for RA, significant improvements have been made to manage the treatment of these patients mainly through the development of anti-TNF agents, which act to neutralize the pro-inflammatory signalling of this cytokine. Such therapies (e.g., adalimumab (Humira®), etanercept (Enbrel®), infliximab (Remicade®), golimumab (Simponi®), and certolizumab pegol (Cimzia®)) have significantly improved the treatment outcome of some RA patients.

Roughly one-third of RA patients show a clinical response to anti-TNF therapies, sometimes achieving remission. Disease progression in these so called "responder" patients, is likely a result of inappropriate TNF-driven pro-inflammatory responses.

The biologic therapies most widely used to treat RA are anti-TNFs. The introduction of this class of drugs has transformed the treatment of RA by achieving LDA or remission for some patients. However, the proportion of patients reaching these treatment targets is low: approximately 34% across multiple clinical studies. For patients failing to respond to anti-TNFs there are alternative approved therapies available such as anti-CD20, co-stimulation blockade, JAK and anti-IL6 therapy. However, patients are switched onto such alterative therapy only after first cycling through different anti-TNFs, which could take over 1 year, while symptoms persist and the disease progresses further making it more difficult to reach treatment targets.

The concept of treating to target, getting patients to LDA or remission as quickly as possible to halt or minimize damage progression has become widely accepted, yet often difficult to achieve in many patients. RA is evaluated using scales of disease severity based on clinical assessments by rheumatologists and patients. Mild, moderate, or severe disease activity is determined in the case of RA using: an assessment of the number of swollen and tender joints; patient and physician-reported assessment of pain, function and global health; as well as serum biomarker levels, which when combined, generate a disease activity score (DAS). Moderate to severe disease activity indicates that a patient's symptoms are no longer being effectively managed. Response to therapy is monitored using the change in DAS and treating to internationally agreed DAS28 scores corresponding to LDA or remission levels.

Cross-cohort irreproducibility due to sample handling, library prep and lower biological signal in blood vs. synovial RA, like most complex diseases, is a collection of different diseases sharing common symptomatic endpoints and therefore a personalized medicine approach is needed to ensure that patients are prescribed a targeted therapy optimal for their individual disease biology. Personalized health care in complex diseases particularly makes sense when response rates to any given therapy are low, serious side effects are associated with each, and alternative effective therapies are available to offer patients. All of these factors apply to RA. By targeting an individual's biology with a complementary therapy physicians, patients, and payers will most efficiently achieve treatment targets. In addition, new therapies should be developed to specifically target non-responders to existing therapies based on their unique disease biology. This is even more important when the high drug, general healthcare and societal costs associated with patients who do not respond to current standard-of-care therapy are considered.

A test that predicts non-response to anti-TNFs prior to initiation of therapy will enable patients to be switched onto alternative therapies faster compared to current standard-of-care, resulting in more patients reaching the treatment target of LDA or remission. Such a predictive response test and its impact on patient care would provide substantial clinical benefits to patients and savings to the healthcare system.

Matching the active disease mechanisms of a given patient at the molecular level, to the mechanism of action of a therapeutic, will significantly improve response rates, allowing more patients to reach treatment goals of low disease activity (LDA) or remission. Achieving treatment targets has significantly meaningful clinical benefits for RA patients in early stages compared to the routine practice of waiting for disease symptoms to significantly worsen before considering alternative therapy.

Figure 6A:
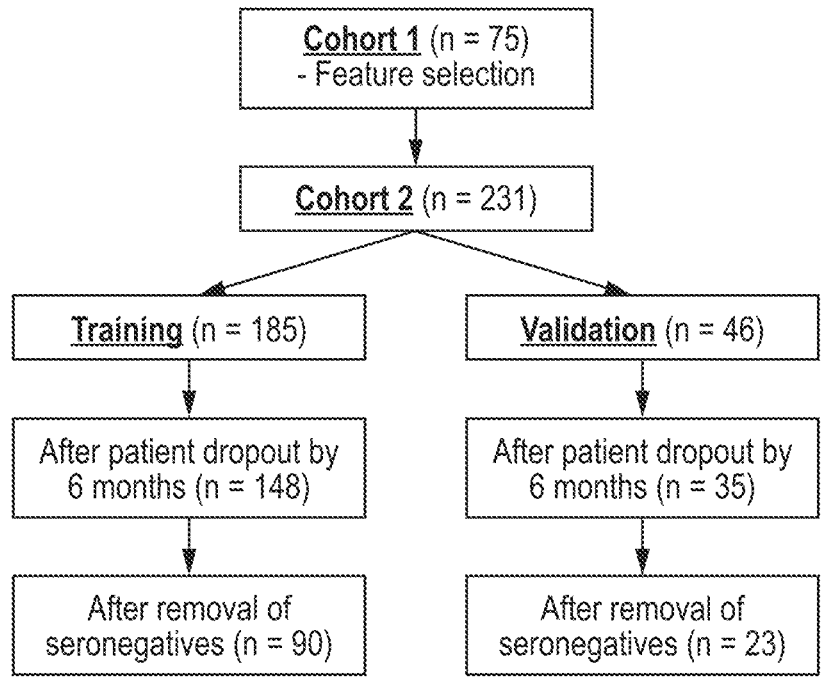
FIG. 6A is a flow chart of cohorts used for feature selection (n=75), model training (n=185), and model validation (n=46).
Figure 6B:
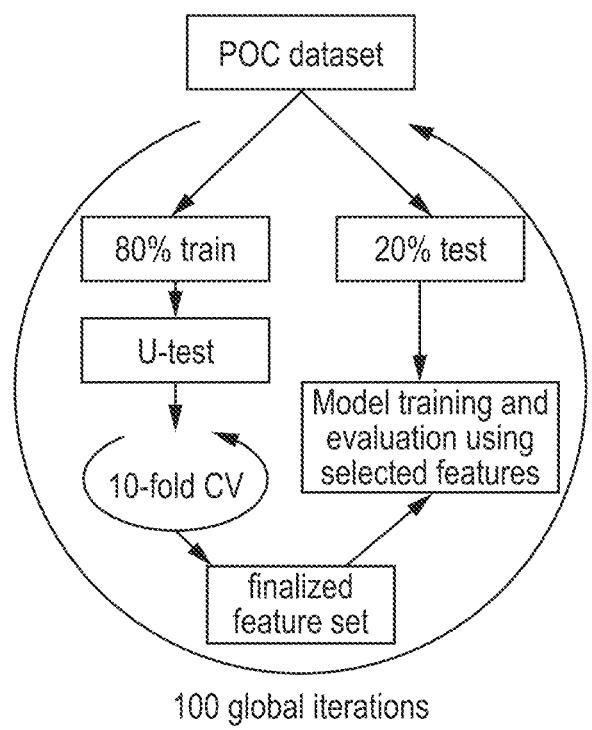
FIG. 6B is a process describing the feature selection process in Cohort 1 of FIG. 6A. POC dataset refers to the Cohort 1 data set of FIG. 6A. 80% of the data is used to train the classifier using the U-test to identify the most discriminative genes, and the 80% data is broken into 10 groups using 10-fold cross-validation to provide the finalized feature set; the finalized feature set is used to for model training and evaluation on the remaining 20% of data. This process is repeated at least 100 times.
Figure 6C:
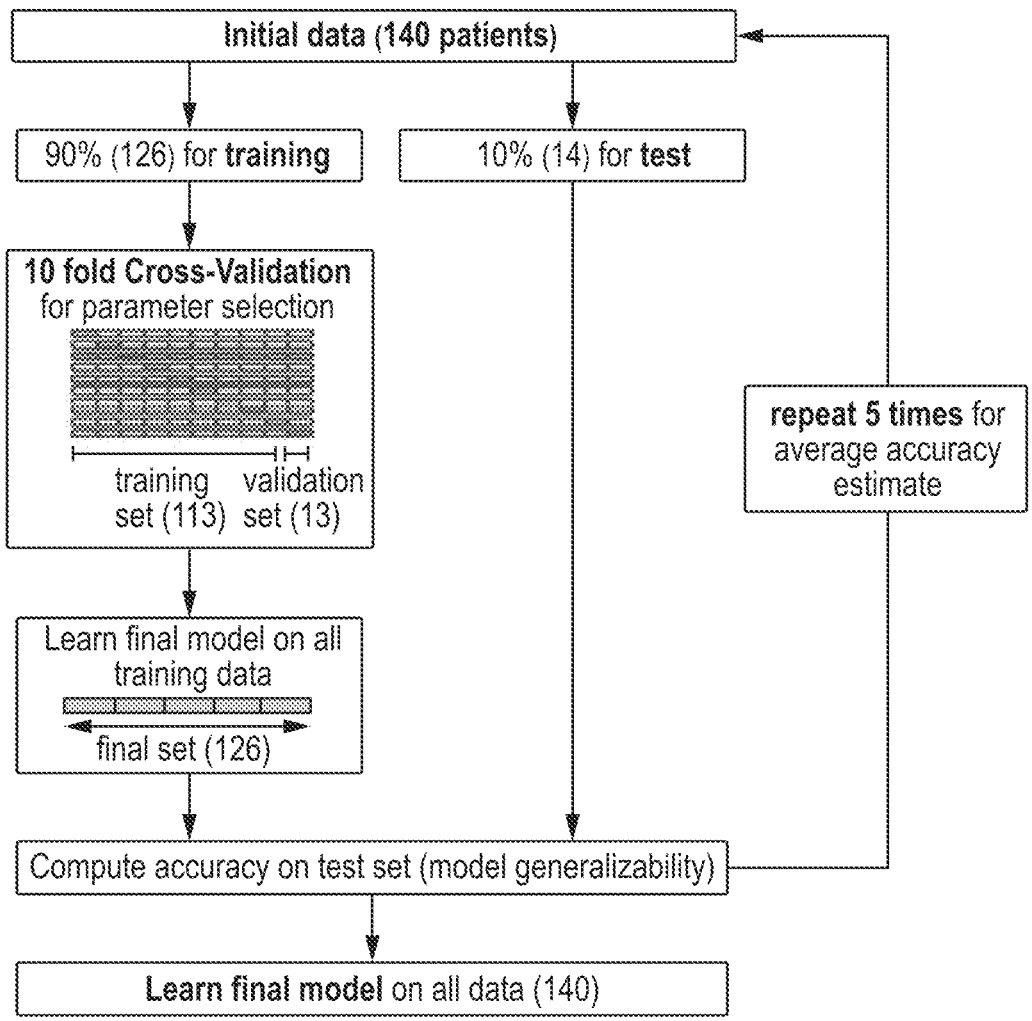
FIG. 6C is a flow chart of feature selection methodology applied to cohort 1.

FIG. 6A is a flow chart of cohorts used for feature selected (n=75), model training (n=185), and model validation (n=46). FIG. 6B is a process describing the feature selection process in Cohort 1 of FIG. 6A. POC dataset refers to the Cohort 1 data set of FIG. 6A. 80% of the data is used to train the classifier using the U-test to identify the most discriminative genes, and the 80% data is broken into 10 groups using 10-fold cross-validation to provide the finalized feature set; the finalized feature set is used to for model training and evaluation on the remaining 20% of data. This process is repeated at least 100 times. FIG. 6C is a flow chart of feature selection methodology applied to cohort 1

Results

Identification of biomarkers that predict response to anti-TNF therapy. In the present study, predictive biomarkers that discriminate between responders and non-responders to anti-TNF therapy were selected from a publicly available dataset published by Bienkowska et al. (cohort 1) and further evaluated among a cohort of 231 Rheumatoid Arthritis patients purchased from CORRONA (cohort 2), among which 185 samples were used for model training (80%), and 46 (20%) used for validation. See materials and methods for cohort descriptions and FIG. 6A for flow chart of samples used for feature selection, model training, and model validation.

Figure 7A:
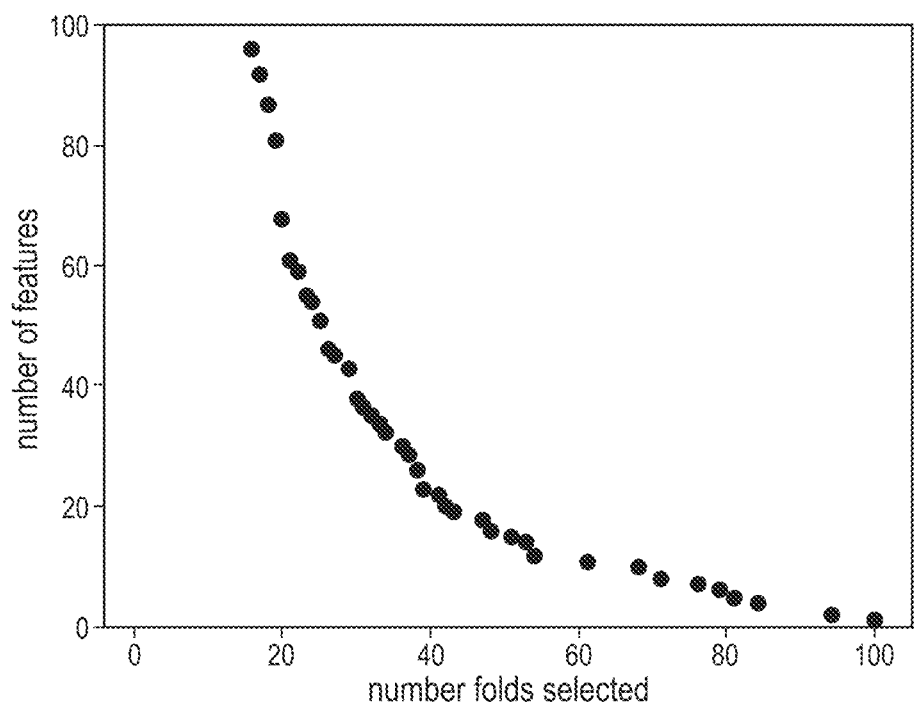
FIGS. 7A-7D related to selection of genes in Abcon Cohort (Affymetrix®) that discriminate between responders and non-responders to anti-TNF therapy.
Figure 7B:
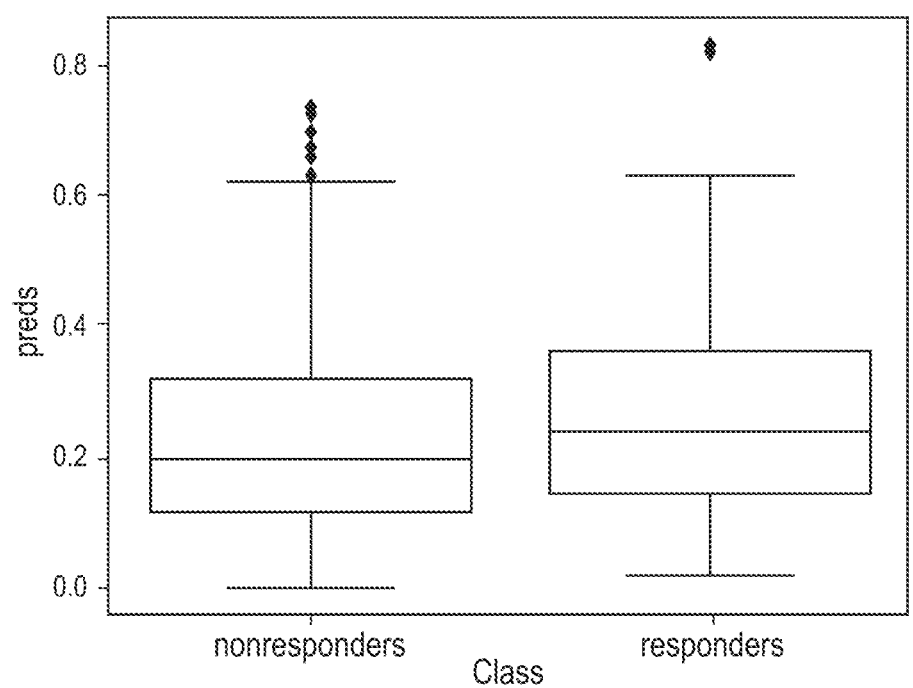
Figure 7C:
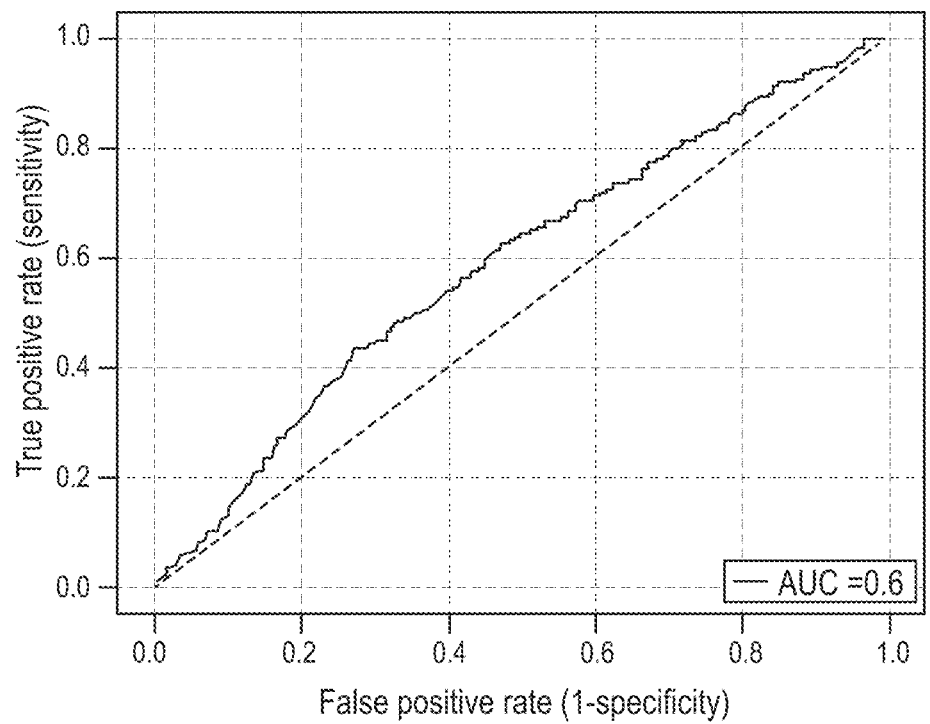

The methodology used for feature selection among cohort 1 samples is depicted in FIG. 6C. Out of the 21,818 total gene transcripts in the dataset, 38 were selected as discriminatory in 30 out of 100 rounds of 20% withheld cross validation using Random Forest. (FIG. 7A). The models from which the predictive genes were selected were evaluated by aggregating the scores from all withheld validation set samples throughout the 100 rounds of cross validation. Here, responders were found to have significantly higher scores (p<0.0001) as compared to the non-responder scores output by the aggregated Random Forest models (FIG. 7B). The aggregated scores resulted in an area under the curve (AUC) of 60% (FIG. 7C), suggesting that the models from which the predictive genes were selected can significantly discriminate between responders and non-responders.

Figure 7D:
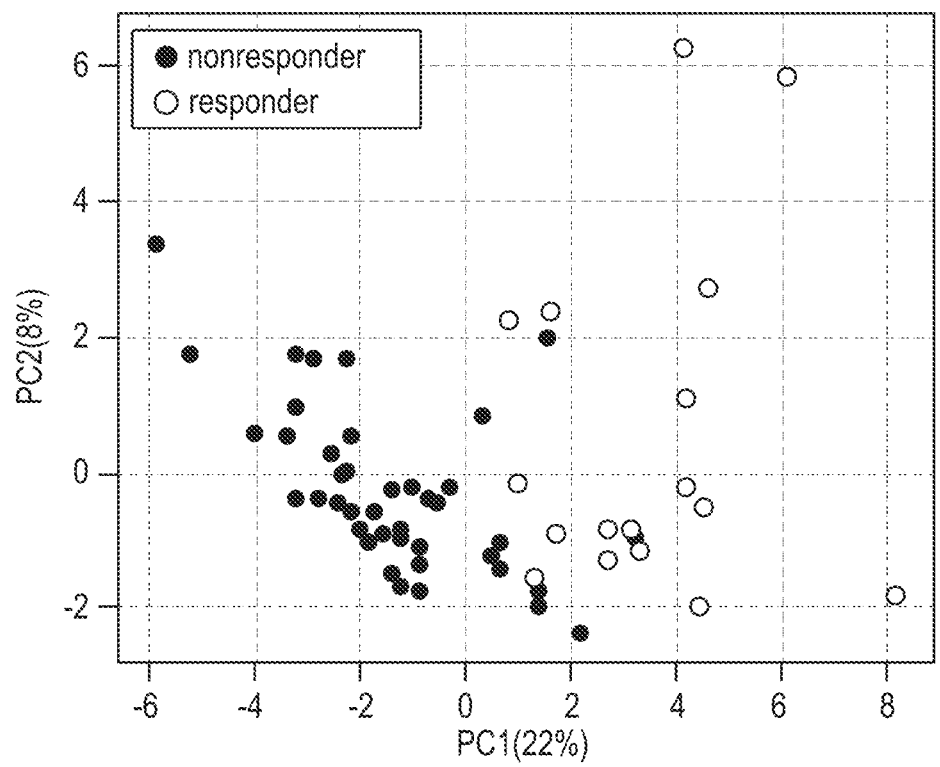

The variance between samples when considering the 38 selected genes is shown in FIG. 7D via principal component analysis (PCA). Here, the majority of variance explained in the data (22%) is along the first principal component (PC1) and is largely associated with response status (responder vs. non-responder), indicating that gene expression profile of these 38 selected genes is distinct between responders and non-responders.

Cross platform model optimization and training. The 38 predictive genes selected from cohort 1 were further evaluated among 231 Rheumatoid Arthritis patients collected from CORRONA (cohort 2). Importantly, data from these two cohorts was generated via two different platforms: microarray (cohort 1) and RNASeq (cohort 2), necessitating retraining of the model using the selected features on the new RNASeq platform. Out of the 38 predictive genes identified in cohort 1, 28 were detectable within cohort 2 training and were evaluated for finalized model development. Out of the 231 patients in cohort 2, 80% (n=185) were used for the optimization of endpoint, inclusion criteria, finalized feature set, and model training, while the remaining 20% (n=46) were set aside for withheld validation.

Figure 8A:
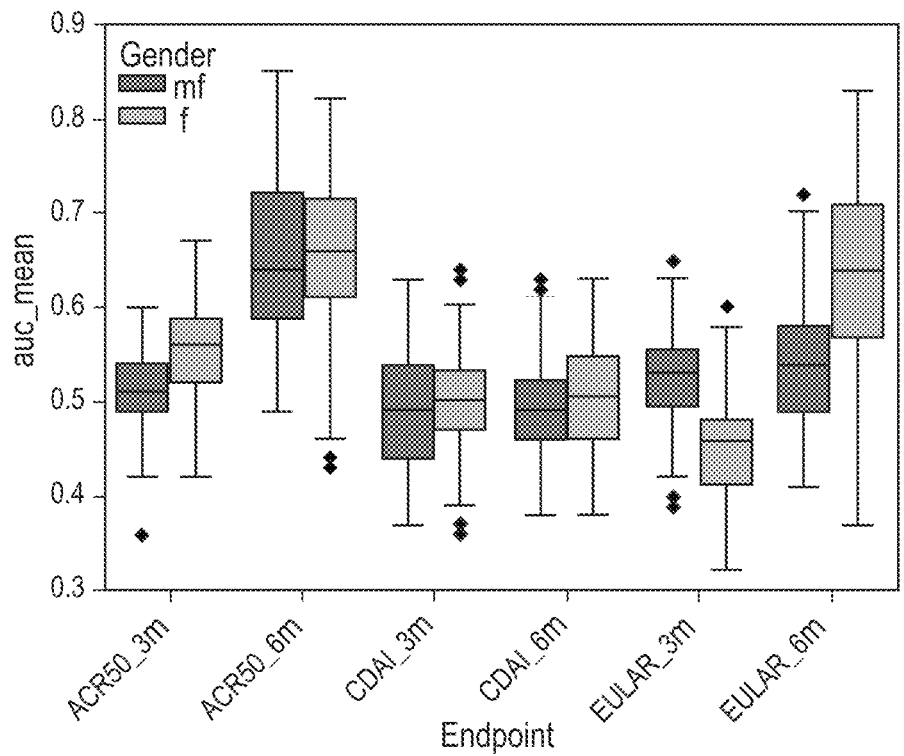
FIGS. 8A-8B relate to optimization of endpoint and inclusion criteria.
Figure 8B:
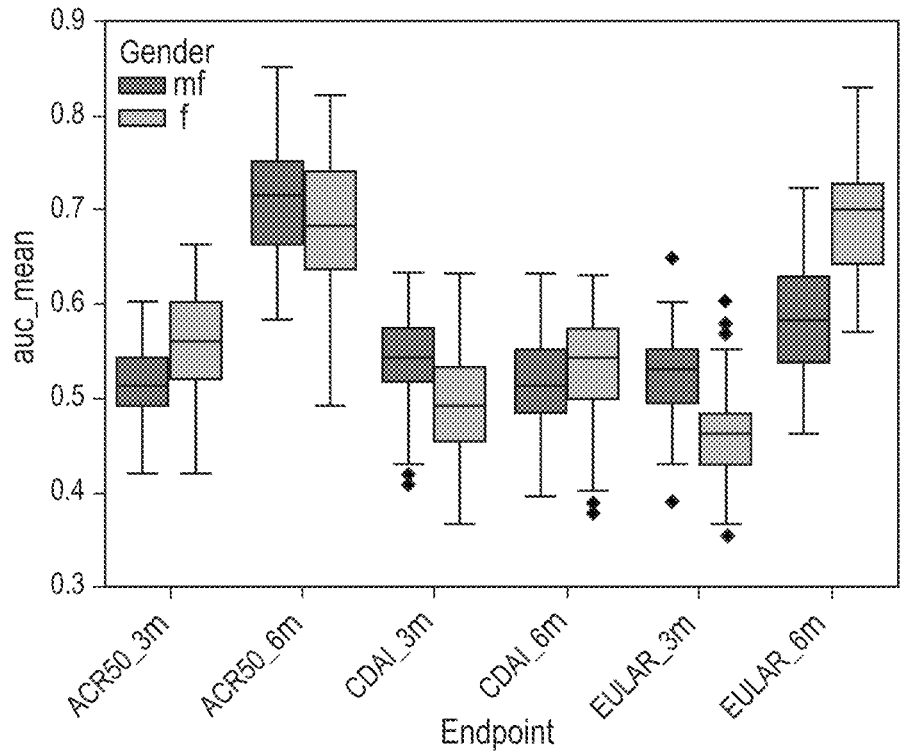

For inclusion criteria optimization, models were built among all training set patients (FIG. 8A) as well as among only the training set patients who tested seropositive for both RF and CCP (FIG. 8B). Seropositivity was investigated as inclusion criteria for model training due to the observation that seronegativity is strongly associated with fibromyalgia and can lead to less accurate response evaluation which could potentially lead to training with mislabeled samples. Within these two populations, models were assessed when using different clinical endpoints (ACR50 3m, ACR50 6m, CDAI 3m, CDAI 6m, EULAR 3m, and EULAR 6m). See materials and methods for information regarding how responders and non-responders were defined by each endpoint.

Highest model performance was achieved with models built among male and female seropositive patients (n=90, see FIG. 6A) using ACR50 6m as the clinical endpoint. Here, a median AUC of 72% was achieved among the 50 iterations of 10% withheld cross validation repeated 10 times. Performance of this model was significantly higher (p<0.0001) than models built with any other endpoint or inclusion criteria. Due to its high performance, this model was selected for further evaluation and withheld validation.

Figure 9A:
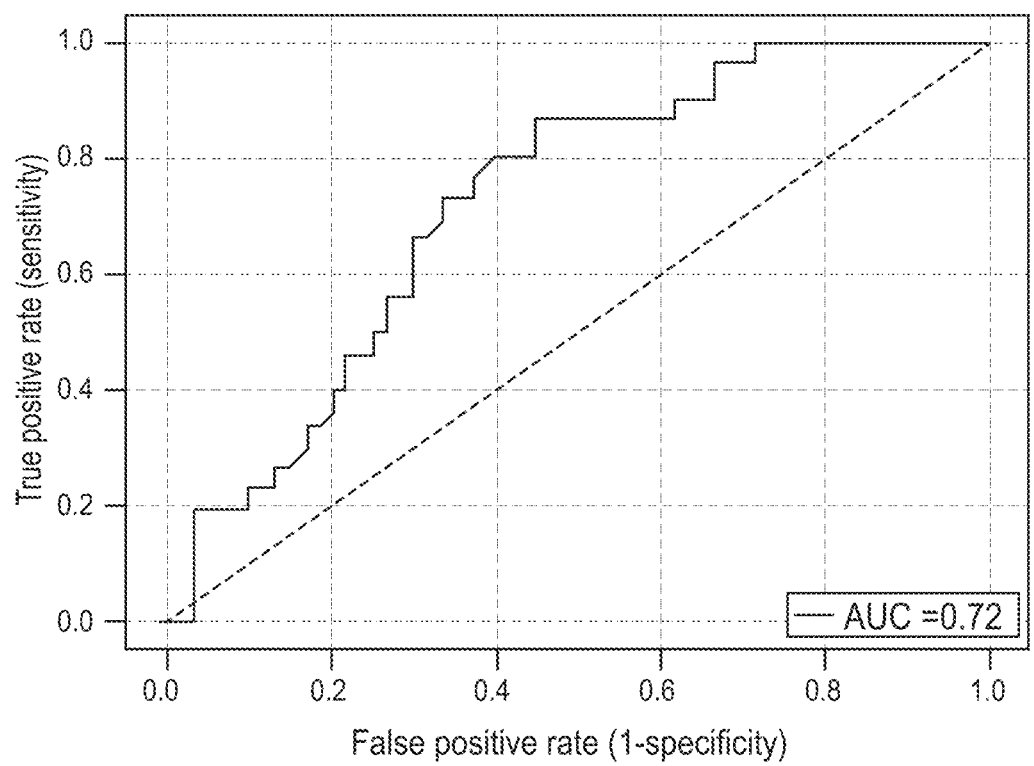
FIGS. 9A-9D relate to representative model performance. Median AUC model produced when considering male and female seropositive patients and using ACR50 at 6 month post treatment as the clinical endpoint.

The median model built among male and female seropositive patients using ACR50 6m as the clinical endpoint is detailed in FIGS. 9A-9D. Aggregating the scores of the validation set samples after 10 rounds of 10% withheld cross validation results in significantly higher scores among responders as compared to non-responders (p<0.00001) (FIG. 9C), and is associated with an AUC of 72% (FIG. 9A).

Figure 9B:
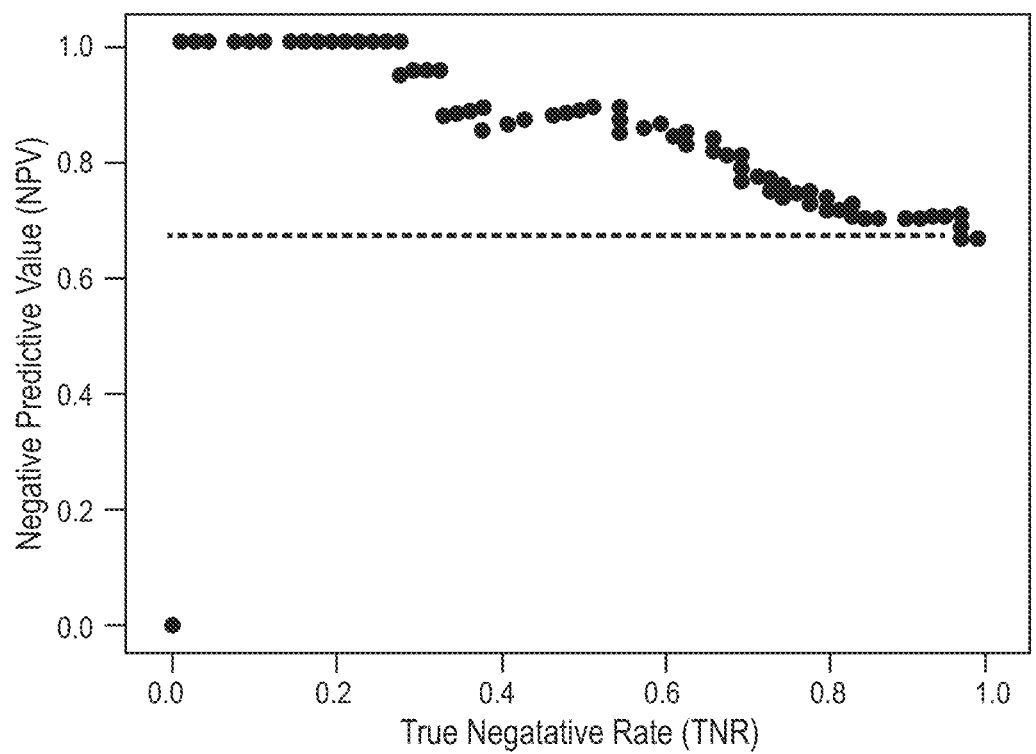
Figures 9C, 9D:
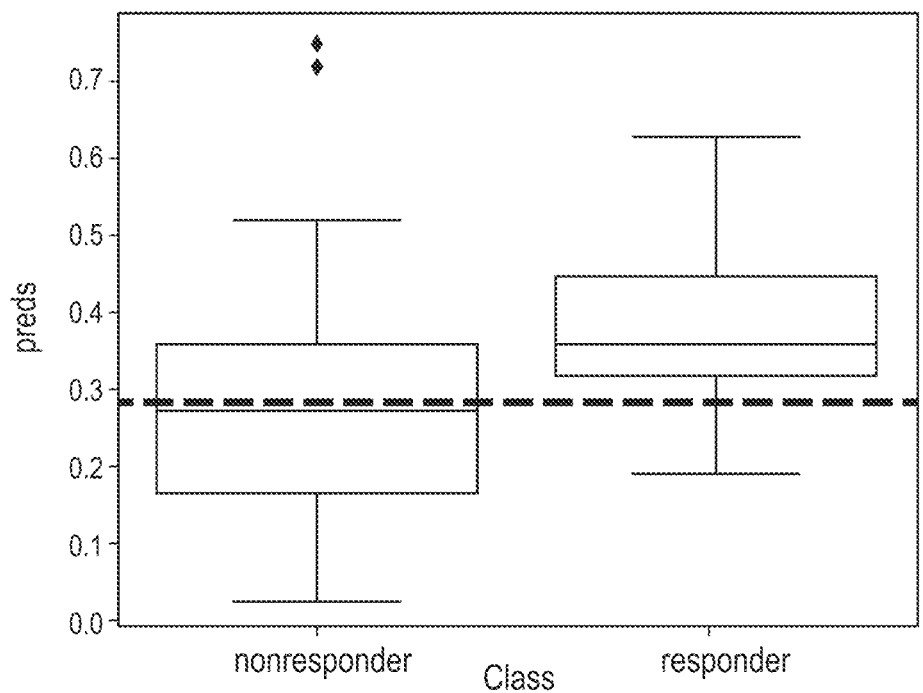

FIG. 9B shows the negative predictive value (NPV) vs. true negative rate (TNR) calculated based on the aggregated validation set samples. Here, an NPV of 0.89 can be achieved at a TNR of 0.55. A confusion matrix showing the agreement between predicted and true classifications at this selected optimal score cutoff (0.29) is shown in FIG. 9D.

Figure 10A:
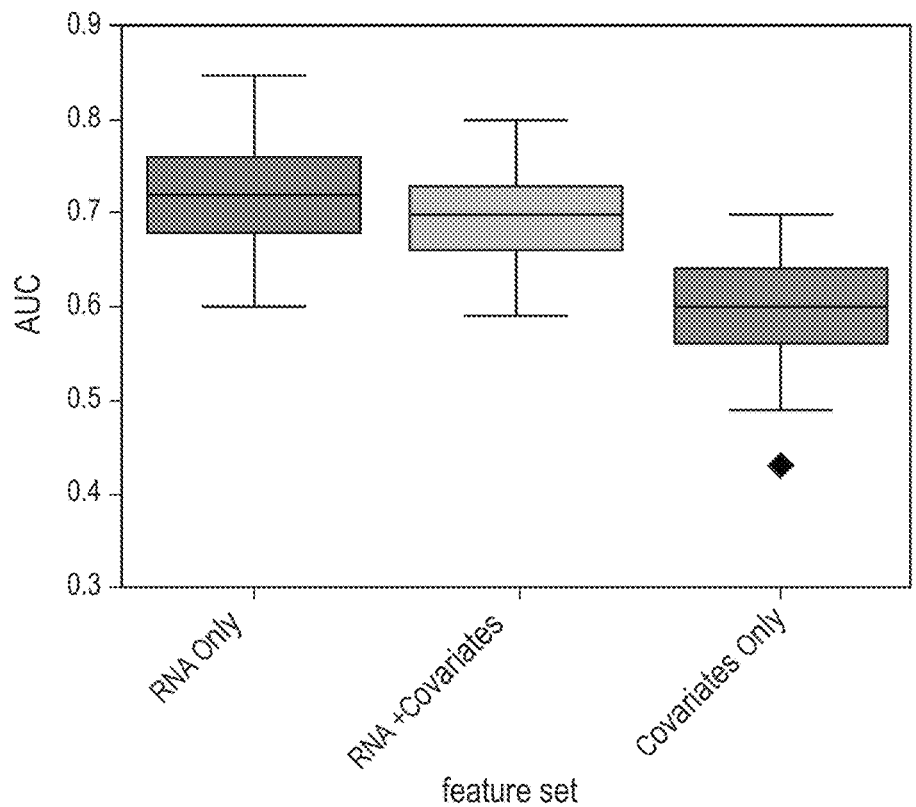
FIG. 10A illustrates model performance with using covariates only, RNA only, and covariates with RNA.
Figure 10B:
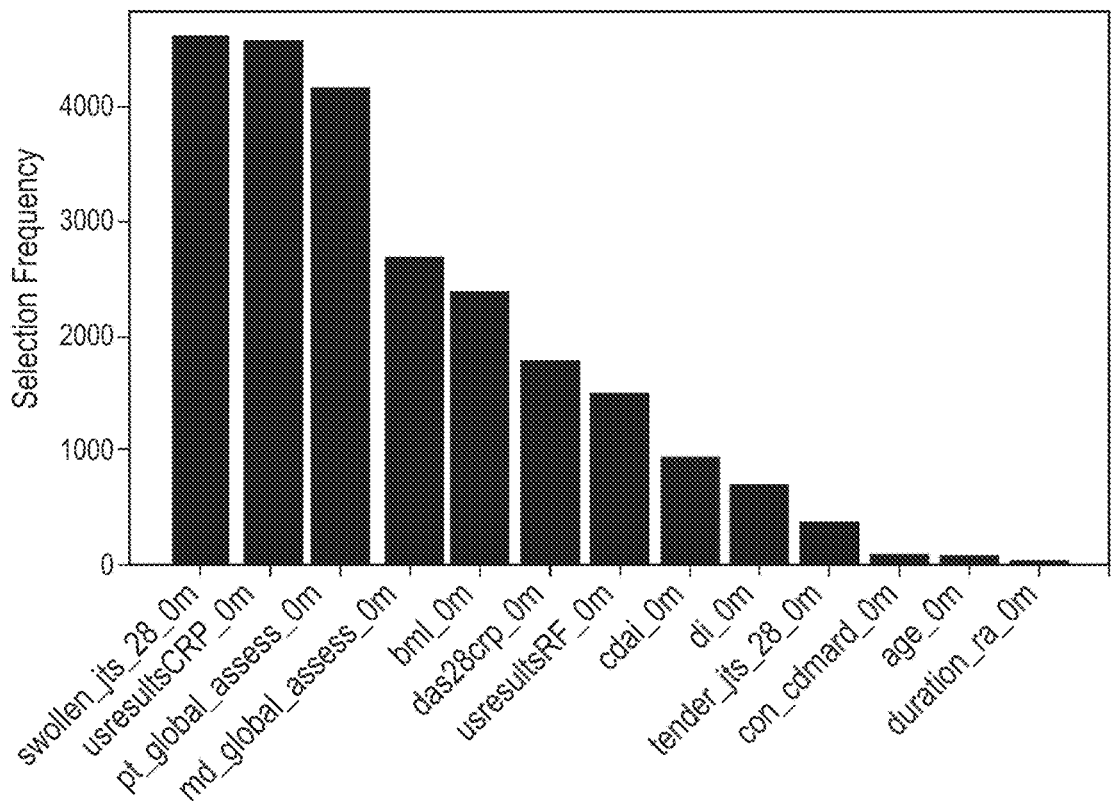
FIG. 10B illustrates selection frequency of covariates.

Selected model performance was further evaluated by comparing classification accuracy against models built using clinical baseline covariates such as age, BMI, patient pain, and the number of tender and swollen joints. A boxplot of models built using RNA only, RNA with covariates, as well as covariates alone among seropositive patients and using ACR50 6m as the clinical endpoint is shown in FIGS. 10A-10B. The highest model AUC was achieved with models built with RNA only (median AUC of 0.72), which was found to be significantly higher (p<0.00001) than models built with covariates only (median AUC of 0.59) as well as models built with RNA combined with covariates (median AUC of 0.70, p<0.005).

Figure 11:
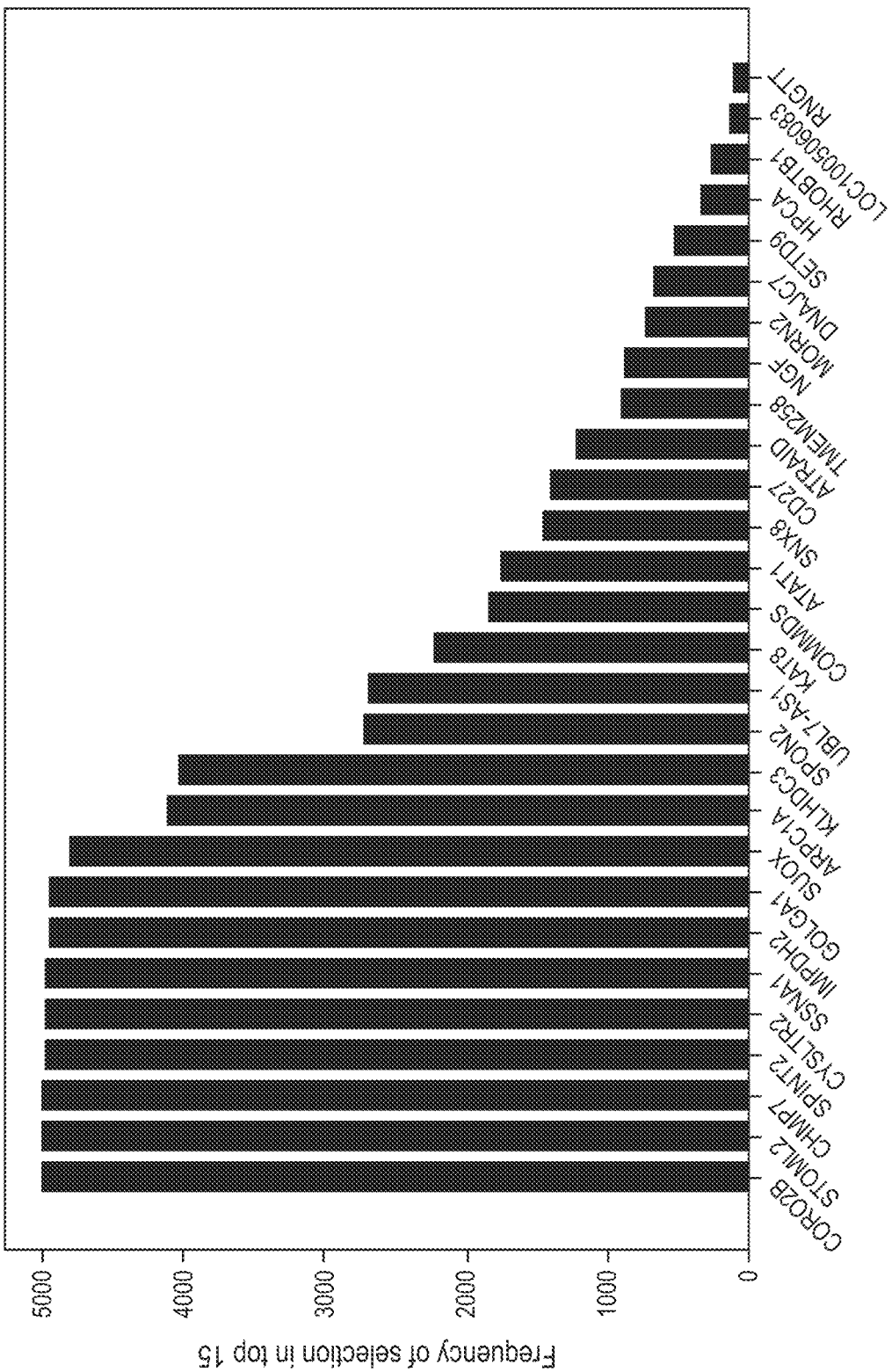
FIG. 11 is a graph of frequency of gene selection in top 15 throughout 50 repeats of 10% cross validation.
Figure 12A:
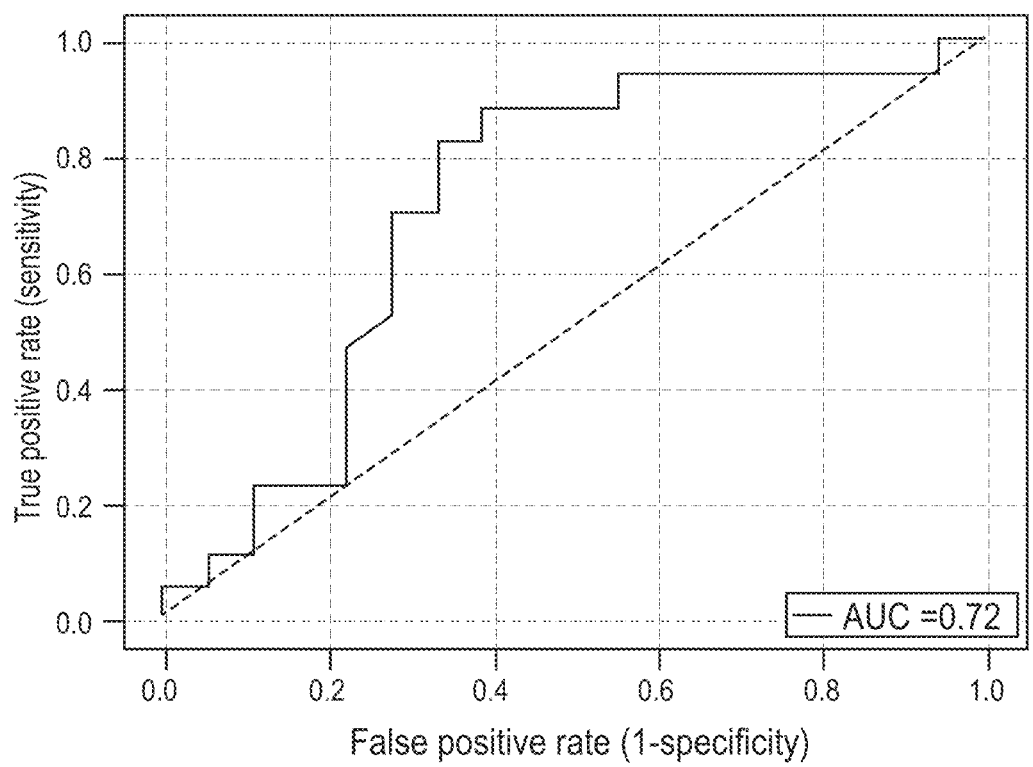
FIGS. 12A-12D relate to a validation of model for the prediction of response to anti-TNF therapy.
Figure 12B:
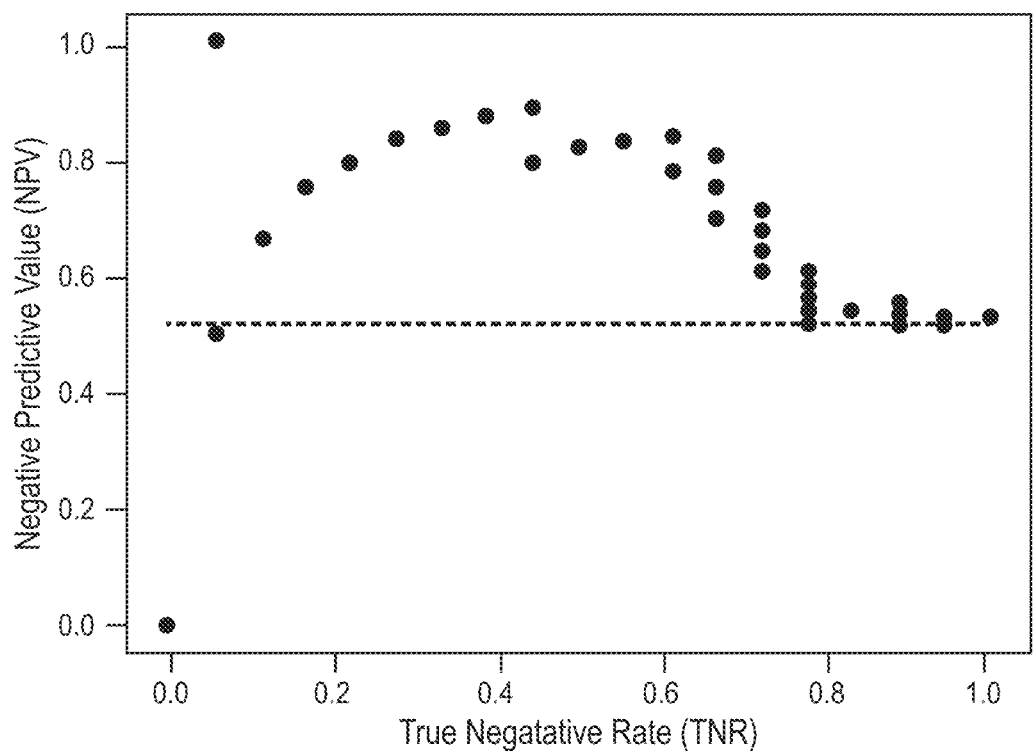
Figures 12C, 12D:
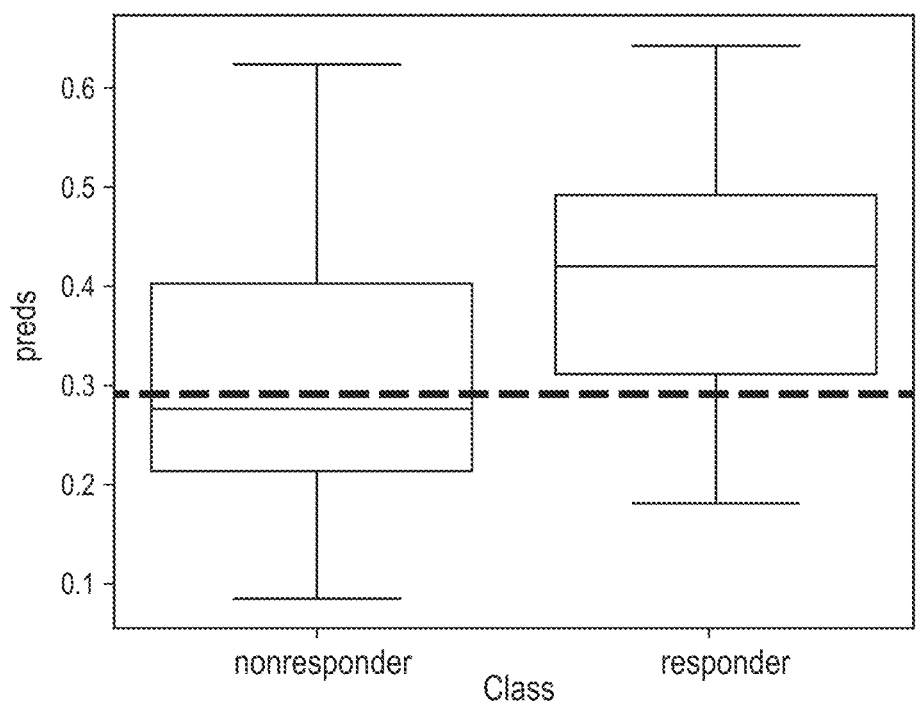
Figure 13A:
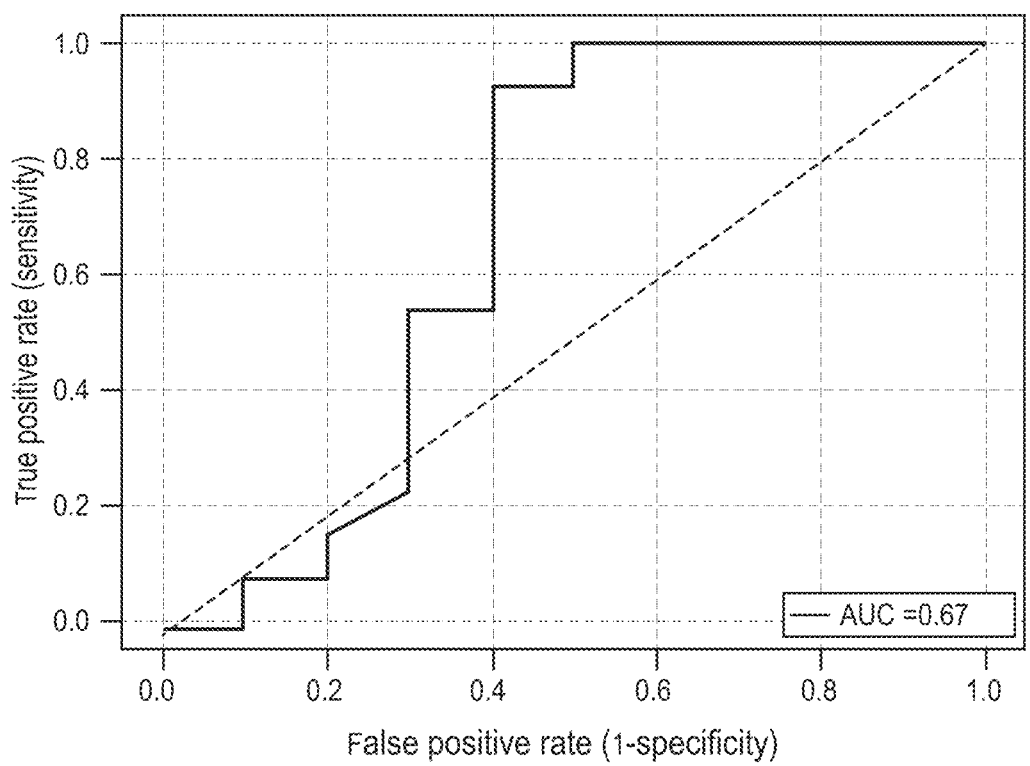
FIGS. 13A-13D relate to validation of model among seropositive patients only (n=23) for the prediction of response to anti-TNF therapy.
Figure 13B:
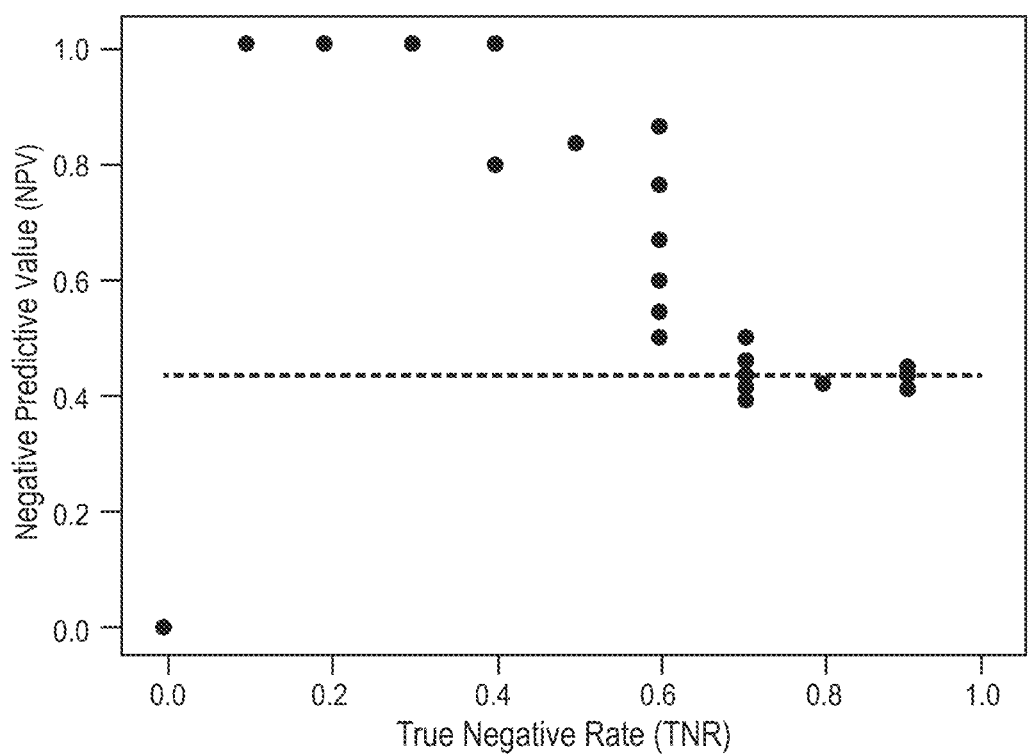
Figures 13C, 13D:
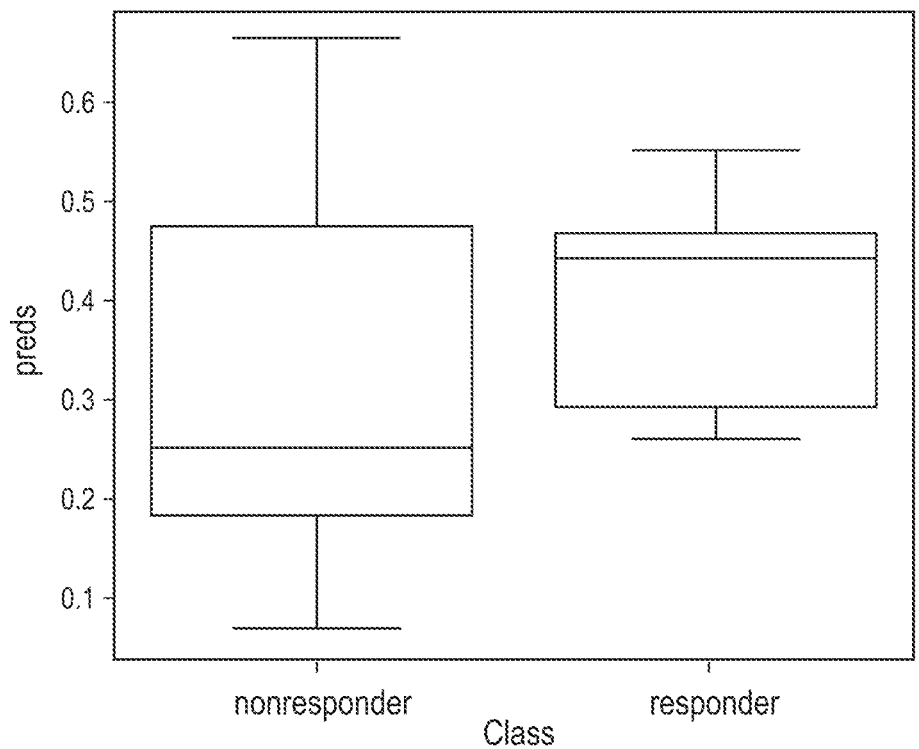
Figure 14:
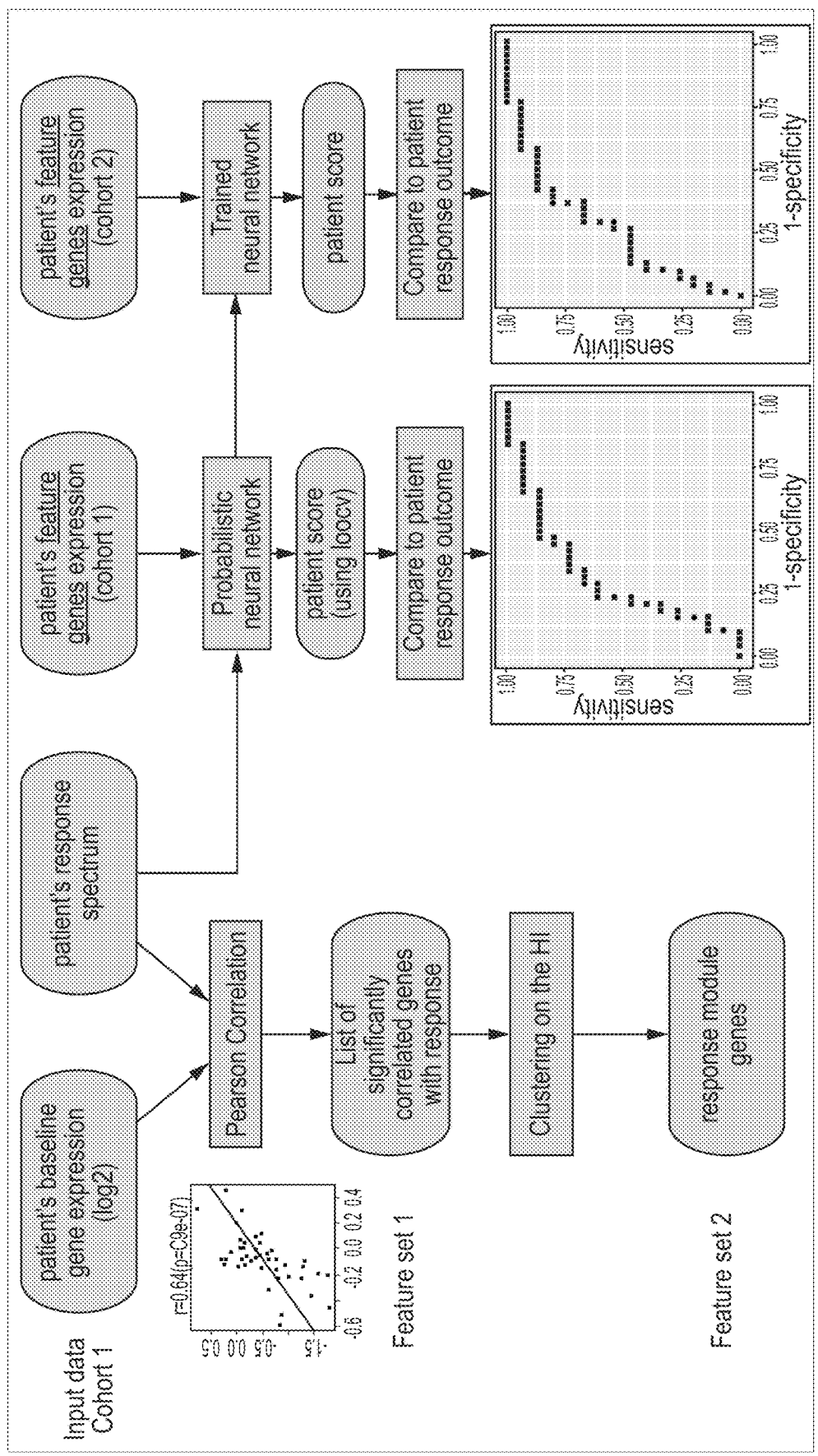
FIG. 14 is an exemplary workflow for developing a classifier.
Figure 15:
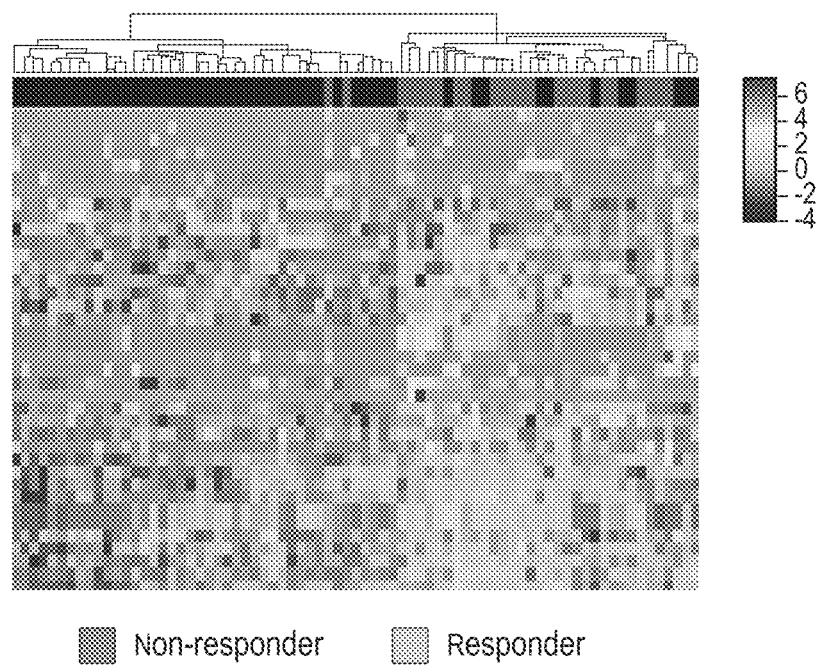
FIG. 15 is A hierarchical cluster analysis of RNA expression data for 38 genes illustrating two main groupings, one predominantly non-responders and the other responders, thereby substantiating the discriminatory nature of these genes for anti-TNF response prediction. The heatmap represents the relative RNA expression level in arbitrary units.
Figure 16A:
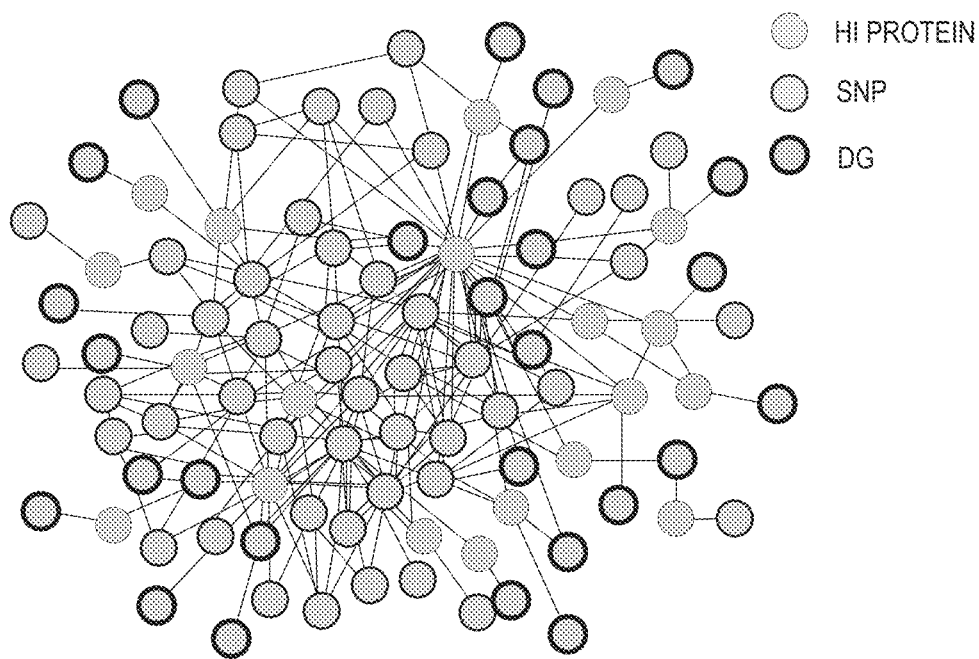
FIG. 16A is a visualization of a subset of the Human Interactome protein-protein network. Proteins included on the network are indicated as grey circles. Those outlined in red represent proteins encoded by SNP-containing RNAs and those outlined in blue represent proteins encoded by response discriminatory genes
Figure 16B:
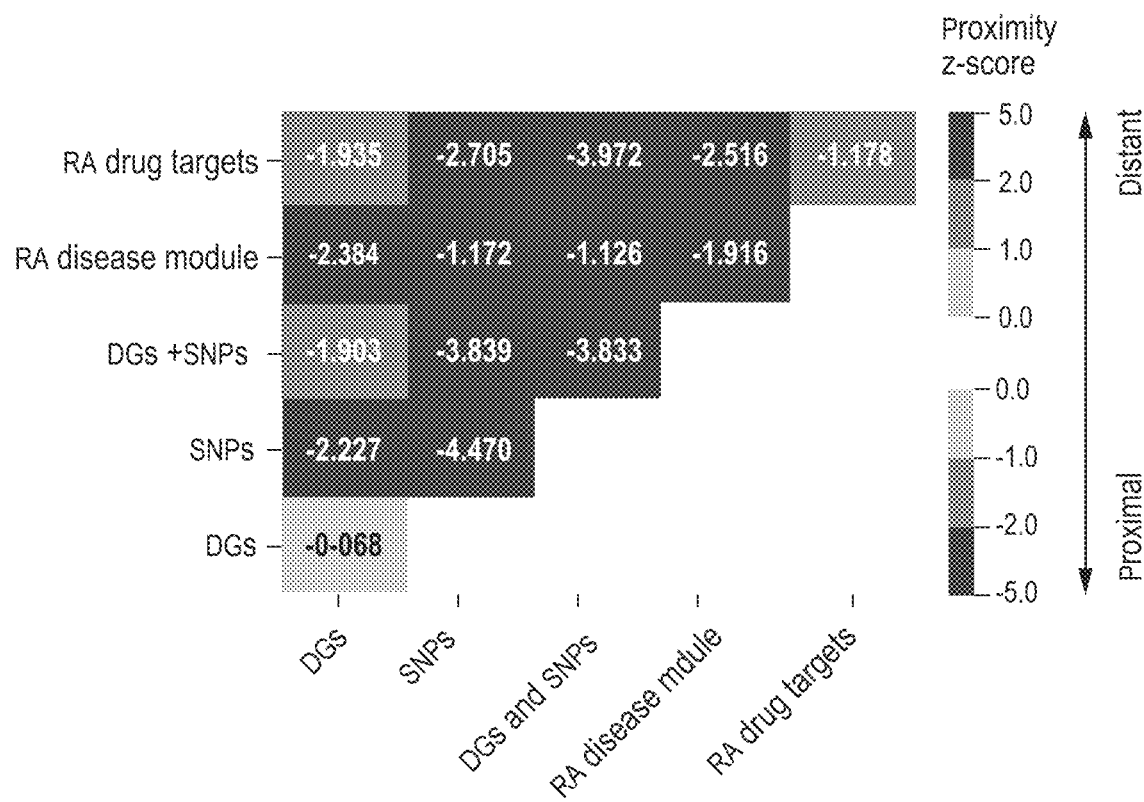
FIG. 16B is a quantitative analysis of the proximity of molecular drug targets, proteins associated with RA (disease module proteins), all molecular features included in development of the PrismRA® predictive classification algorithm, proteins encoded by SNP-containing RNAs (SNPs) and proteins encoded by discriminatory genes (DGs). Molecular features included in the final predictive classification algorithm are yellow.
Figure 17:
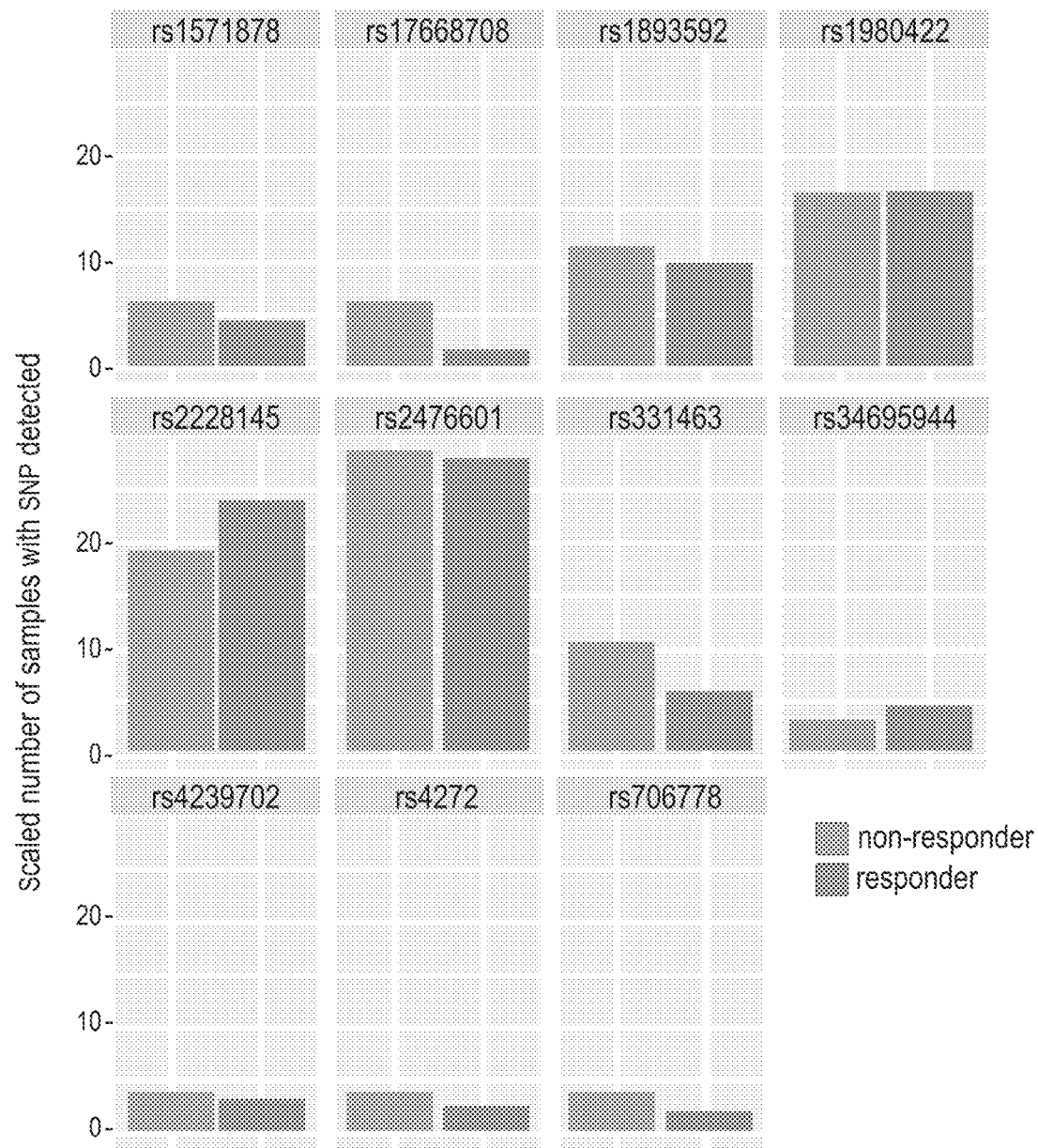
FIG. 17 is a series of bar graphs depicting a percentage of responder and non-responder RA patients in the training cohort for which the selected SNP was detected in at least ten patients.
Figure 18:
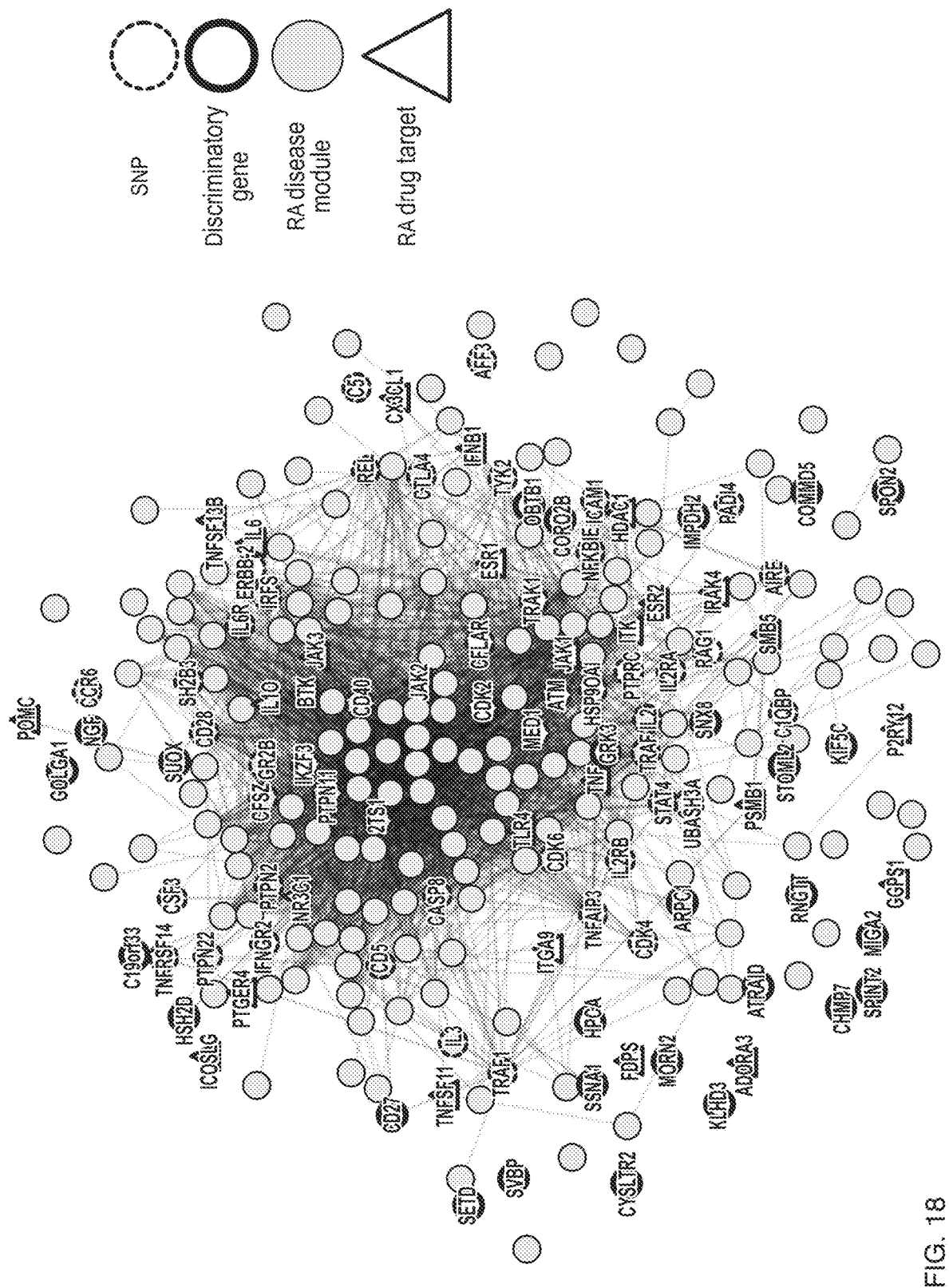
FIG. 18 is a Human Interactome subnetwork containing RA disease module, RA drug targets, and classifier features (SNPs and DGs).
Figure 19:
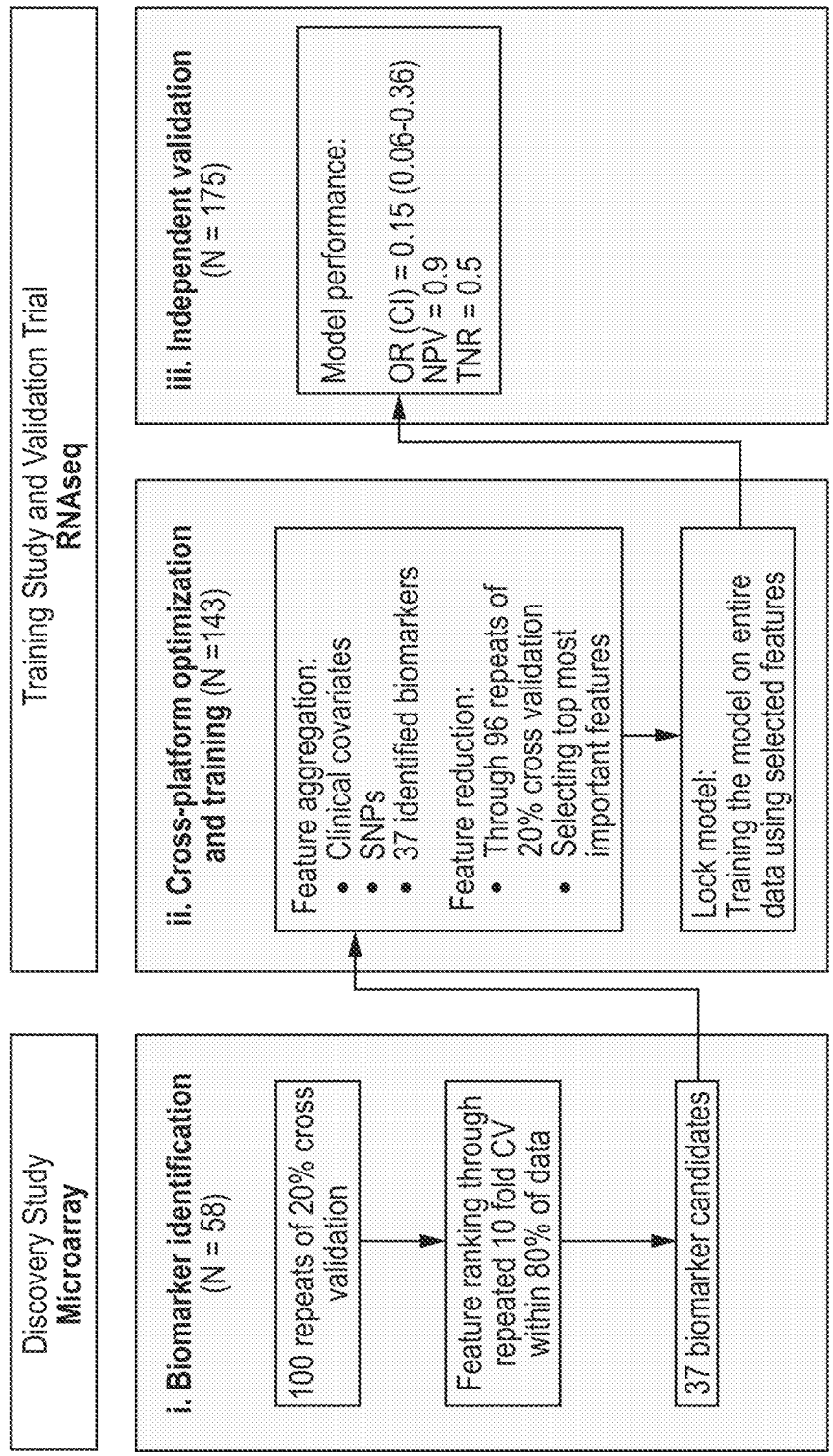
FIG. 19 is a flow chart describing development of anti-TNF drug response algorithm in RA. Gene expression that discriminates between responders and non-responders to anti-TNF therapies were selected from a publicly available microarray dataset. In a cross-platform analysis, these features were combined with network disease module-associated SNPs and clinical factors, then used to train a machine learning algorithm using RNAseq data. Performance of the predictive drug response algorithm was validated in an independent validation trial.

Feature robustness was evaluated by measuring their frequency of selection in the top 15 (out of 28) features throughout the 50 rounds of 10% cross validation (FIG. 11). At random, the expected number of selections was determined to be 2,679 (54%) via simulation. Eleven genes (CORO2B, STOML2, CHMP7, SPINT2, CYSLTR2, SSNA1, IMPDH2, GOLGA1, SUOX, ARPC1A, and KLHDC3) were selected in greater than 4,000 out of a possible 5,000 selections (80%) and are considered the most robust subset of the 28 gene candidates evaluated as they were selected at greater frequency than random expectation. A substantial drop in selection frequency is observed after the top 11, with the next most frequently selected gene being selected in only 54% of the 5,000 possible selections. These remaining 17 genes were not considered for finalized model development and validation because they were not selected at a greater frequency than random expectation.

Validation of optimized model for the prediction of response to anti-TNF therapy. Classifier performance was further evaluated by an additional 46 patients who were part of the same CORRONA study cohort, but whose RNA was sequenced at a later time for the purpose of final model validation. Out of the 46 samples withheld for model validation, 35 were followed-up with at the 6 months post therapy initiation and were used for model validation. The full set of 90 training samples were used to train a finalized random forest model with the eleven selected genes as input (CORO2B, STOML2, CHMP7, SPINT2, CYSLTR2, SSNA1, IMPDH2, GOLGA1, SUOX, ARPC1A, and KLHDC3). The results of model validation are shown in FIG. 11 which achieved an AUC of 0.72, an NPV of 0.85, and TNR of 0.61. The optimal model cutoff (0.29) determined from training data (see FIG. 9C) was used to for confusion matrix generation (FIG. 9D). The results of model validation among the seropositive only patients (n=23) is shown in FIGS. 13A-13D.

Discussion

To the best of our knowledge, this is the first time biomarkers predictive of response to anti-TNF therapy in the context of Rheumatoid Arthritis have been selected, optimized and validated in a cross cohort, cross platform analysis. Here, 28 predictive genes were selected from a publicly available dataset where gene expression was quantified via microarray (Affymatrix). After model optimization on an RNASeq platform, a subset (11) of the 28 genes were used to build a model which was shown to have a validated AUC of 72%, an NPV of 0.85 and a TNR of 0.61. These results suggest that gene expression profiles can be used to reproducibly predict nonresponse to anti-TNF therapy, and this profile could potentially be used to screen away non-responders to explore alternative therapies and subsequently increase the response rate for those prescribed anti-TNF therapy for the treatment of RA.

The current lack of a clinically useful classifier to predict anti-TNF response is not due to a lack of effort on the part of the research community. Rheumatoid factor (RF) and anti-cyclic citrullinated peptide (CCP) are biomarkers used to diagnose RA and are found in about 80% of patients. The levels of these circulating biomarkers have been correlated with response to Rituximab, however the trends were modest and not of sufficient utility to be clinically useful. Many genetic association studies have been undertaken to evaluate the predictive value of genetic risk loci for response to treatment with anti-TNFs and alternative therapies. Associations were found but effect sizes were modest. One study estimated that only 2% of the change in DAS28 score could be accounted for per risk allele in tocilizumab treated patients. In an independent study that tested eight different gene expression signatures predicting response to anti-TNF, most signatures failed to demonstrate sufficient predictive value to be of clinical utility. And several studies have discussed the inability for various classifiers to meet required performance criteria in independent cohort of patients. Classifiers for predicting response to alternative approved therapies for RA tocilizumab and rituximab have also been published but these also failed to be validated in an independent cohort of patients. What many of these studies have in common is that the analytical framework used only looks for mathematical correlations between genetic and clinical outcome data sets. As a result, biological context is not captured which explains why many of these classifiers underperform or why results can't be replicated in independent cohort of patients.

RNA counts from blood or tissue contain the information needed to describe an individual patient's disease biology. However, given the large number of features (RNAs) generated by the whole transcriptome analysis (see Methods) and relatively small number of samples, the challenge has always been to identify the smaller set of causal genes responsible for a patient's disease biology. One approach to increase sample size is to leverage information collected from publicly available datasets, however differences in study design, specifically the platforms used for RNA quantification, present problems for direct translation between cohorts. Cross platform analysis of gene expression datasets is a subject that has been widely studied for diagnostic development in areas including Tuberculosis. In the present study, biomarkers were identified from a dataset generated by microarrays and further evaluated within an RNASeq dataset. Although data generated on these two platforms has been shown to highly correlate, differences in dynamic range pose challenges for diagnostic model development on one platform and validation on another. In the present study, a microarray dataset was used to reduce the high dimensions of gene expression data down to a smaller number of genes associated with response, so that a more targeted approach could be taken within our RNASeq dataset. Cross validated models built on either platform were shown to have consistent performance.

As there are many accepted clinical definitions of response to anti-TNF therapy, and no gold standard, we elected to evaluate all endpoints for which data was available and determine which endpoint was best reflected by patient's baseline gene expression profile among training set samples. The largest impact on model performance was found to be the clinical endpoint used for class labels. Certain clinical endpoints such as CDAI 3m, CDAI 6m and EULAR 6m were not able to perform significantly above random (AUC 50%), while others such as ACR50 6m and EULAR 6m achieved median AUCs as high as 72%. As these endpoints highly correlate with each other, this finding suggests that small percentages of mislabeled samples can have a large impact on overall model performance, and in turn, some endpoints are better reflected by patient transcriptional profile. Future studies should further investigate the relationship between clinical endpoints and patient transcriptome to gain insight on what endpoints may be most biologically relevant.

Seropositivity as an inclusion criteria was investigated due to the fact that seropositive patients have been shown share similar disease progression and are more likely to have more severe RA, while seronegative RA patients have been hypothesized to have a different form of inflammatory arthritis such as psoriasis related arthritis or a spondyloarthropathy. Therefore, selection of seropositive patients for diagnostic model development may be considered a less heterogeneous RA population than combining both seropositive and seronegative patients. Removal of seronegative patients from our model training resulted in both higher median and standard deviation of model AUC.

Covariate Analysis. In order to further demonstrate the robustness of our RNA based gene expression test, comparisons were made against models built using clinical covariates at baseline. The fact that models built with RNA only performed significantly better than models using clinical covariates demonstrates the value of information obtained from the transcriptome over other simple measurements that may be taken at baseline during visits to the clinic.

TNF-$\alpha$ is a potent and central mediator of inflammation and microbial immunity, as well as of many homeostatic physiological functions. It is the key target of anti-TNF-$\alpha$ drugs for the treatment of autoimmune diseases, including RA. TNF-$\alpha$ is expressed as a transmembrane protein and its gene expression is regulated by three transcription factors: nuclear factor kB (NF-$\kappa$B), c-Jun activator protein-1 (AP1) and nuclear factor associated with activated T cells (NFAT). Binding of TNF-$\alpha$ to its cognate receptor initiates a complex and diverse array of signaling pathway activities that can culminate in cell death or cell activation. TNF-$\alpha$ receptor activation leads to the synthesis of proinflammatory cytokines, chemokines and prostaglandins. Additionally, TNF-$\alpha$ regulates cytoskeletal re-organization essential for leukocyte migration. This pleiotropic role of TNF-$\alpha$ activation is reflected in the functions of nine of the eleven proteins encoded by genes included in the classifier. Two are involved in pro-inflammatory mechanisms, five in cytoskeleton remodeling and function, one in NF-$\kappa$B regulation and two in T cell activation. For example, Cysteinyl leukotriene receptor 2 (CYSLTR2) is a G-protein coupled receptor (GPCR) that is activated by leukotrienes—proinflammatory lipid mediators rapidly generated by activated innate immune cells, such as granulocytes, macrophages and mast cells (PMID: 25572555). This class of GPCRs trigger a variety of leukocyte functions including chemotaxis, degranulation and production of superoxide anion.

The role of the cytoskeleton remodeling is prominently visible in this classifier. The cytoskeleton is a three-dimensional intracellular proteinaceous network that is responsible for cell shape, motility, internal organization, and movement of organelles and vesicles. The interplay of cytoskeletal components and RA disease biology is likely multifaceted. Dynamic actin remodeling is critical for efficient homing and extravasation of immune cells to sites of inflammation. The temporal and polarized release of cytokines depends on cytoskeleton remodeling. The prevalence of cytoskeletal components in our classifier suggests that the cytoskeleton may play a more central role in RA disease biology than has been previously appreciated and may be pivotal to predicting non-response to anti-TNF-$\alpha$ therapy.

Autoantigens are critical components in establishing the inappropriate immune responses central to autoimmune diseases such as RA, therefore it is no surprise that autoantigens are highlighted in our classifier. An immunologic hallmark of RA is the presence of autoantibodies in the blood, including rheumatoid factor (RF)—a family of autoantibodies directed against the Fc portion of immunoglobulin (Ig) G. Our analysis identified two additional autoantigen genes associated with RA: GOLGA1 and NA14. GOLGA1 encodes Golgin-97, which is a molecular tether that localizes transport vesicles to the Golgi (5). Furthermore, elimination of Golgin-97 activates NF-κB. NA14 is a hallmark autoantigen of another autoimmune disease known as Sjogren's syndrome, which attacks the glands that make tears and saliva. Furthermore, autoantibodies against cytoskeletal components actin and myosin are enriched in some RA patient sera (PMID: 12447636).

Genetic and environmental elements involved in immune mediated diseases such as RA. The risk of having RA increases in first-degree relatives of patients and there is a relatively high concordance (40%) of autoimmunity in identical twins, indicating a genetic component in the aetiology of immune-mediated diseases. In the past decade with the availability of singlenucleotide polymorphisms (SNP) and haplotype maps of the human and mouse genomes, coupled with the analysis of DNA from very large well characterised patient cohorts, we have seen an explosion in the number of genes found associated with human autoimmune diseases. However, the concordance of immune-mediated diseases, whilst significant, is less than 40% in monozygotic twins suggesting that environmental factors and epigenetic elements also play a role in the development of such diseases. Moreover, current studies reveal that the allelic variations associated with risk in immune genes did not evolve to increase predisposition to autoimmunity but, rather, were selected for as a result of environmental elements such as, diet, microbiota, vitamins, smoking, etc. In conclusion, the complexity of autoimmune diseases, in particular RA, is confirmed by many different groups using diverse tools and mechanisms. These studies demonstrate the heterogeneity of RA at the molecular level and explain why no single targeted treatment can work for all patients, further amplifying the significance of our classifier. In this study we have been able to predict non-response to anti-TNF therapy in RA patients using a gene-based classifier. The genes in the classifier are relevant to some of these already well-known genetic risk factors, in addition to other genes that are novel and not well studied, including those that can be impacted by environmental factors and epigenetic elements.

Methodology

Study Populations: Cohort 1—Predictive genes were identified from the publicly available dataset GSE15258 published in Bienkowska et al., *Genomics*, 94: 423-432 (2009), the entirety of which is incorporated herein by reference.

Cohort 2:

Biologically naive patients.

The Consortium of Rheumatology Researchers of North America (CORRONA) has been collecting "real world" longitudinal data from over 38,000 RA patients and their physicians in the US since 200165. Data are collected with Institutional Review Board/Ethics Committee approvals at each Registry visit and includes disease severity and activity, medications, adverse events, quality of life, laboratory and imaging results, and socio-demographic information 65.

The CERTAIN trial was initiated by the CORRONA Registry to collect and compare data from RA patients with moderate to severe disease activity starting (biologic naive) or switching biologic agents to compare the effectiveness and safety of biologic medications such as anti-TNF therapies (e.g., adalimumab (Humira®), etanercept (Enbrel®), infliximab) (Remicade®, certolizumab pegol (Cimzia®), and golimumab (Simponi®)), and alternative mechanism of action drugs (e.g., abatacept, rituximab, and tocilizumab). The primary comparative effectiveness endpoint was attainment of low disease activity at one year among patients exposed to at least one anti-TNF agent prior to enrollment. Patient visits and blood work were mandated every three months.

The CERTAIN trial was open to all patients with a moderate level of disease activity defined as a clinical disease activity score (CDAI) of >10 who were starting or switching biological agents. Additionally, PAXgene™ Blood RNA tubes were collected from CERTAIN patients at baseline, and stored at −80° C., prior to this study.

For this retrospective validation study, PAXgene™ whole blood RNA samples were selected from patients who were all treated with concomitant MTX prior to initiation of biological (b) DMARD and still on MTX at the three-month follow-up visit with no change in dose >5 mg. After the three-month visit, patients could discontinue the biologic. Patients were allowed to be on concomitant hydroxychloroquine (Plaquenil) but no other csDMARD at baseline, or at the three-month follow-up visit. Patients were allowed to be on prednisone (<10 mg/day) at the three-month visit. A higher dose (>10 mg/day) of prednisone was allowed at the six-month visit. The clinical assessments included tender and swollen joint count, physician and patient global diseases activity scores, patient pain and fatigue, and quality of life surveys. Laboratory studies included complete blood count, C-reactive protein, RF, and anti-CCP titer. Patients were excluded from the study if they required a dose change of MTX or hydroxychloroquine or were treated with other csDMARD therapies at baseline or the three-month visit. Patients on doses of prednisone >10 mg/day were also excluded from the study.

Evaluation of response to anti-TNF therapy. Applicant defined response as achieving low disease activity defined by CDAI <10, DAS28CRP<2.9 or response equivalent to ACR50 or EULAR good response. Patient response to anti-TNF therapy was assessed at 3 and 6 months post initiation of anti-TNF therapy.

RNA isolation and QC. Total RNA, including miRNA, was isolated from blood collected in PAXgene™ Blood RNA Tubes using the PAXgene™ Blood miRNA Kit (PreAnalytix) according to manufacturer's instructions. The purified RNA was stored at −80° C. RNA quality was assessed using the Agilent™ Bioanalyzer and samples were quantitated by spectrophotometry using NanoDrop™ ND-8000 spectrophotometer. Samples with a RIN greater than 5 and at least 1 µg of RNA proceeded to GlobinClear™ processing.

Globin depletion and cDNA library preparation. Globin mRNA was depleted from blood derived total RNA samples using the GlobinClear™-Human kit (Thermo Fisher) according to the manufacturer's instructions. The final globin mRNA-depleted RNA samples were quantitated by spectrophotometry using a NanoDrop™ ND-8000 spectrophotometer.

Sequencing libraries were created using the Illumina® TruSeq Stranded Total RNA assay method. Ribosomal RNA was preferentially removed prior to library generation using the RiboZero® Magnetic Gold kit according to the manufacturer's instruction. The final libraries were amplified via PCR and quantified, normalized and pooled for sequencing. Libraries were run on a Nextseq® 500 sequencer for 75 cycles targeting a minimum of 30 M reads per sample.

RNA-seq analysis and gene expression preprocessing. An average of ~40.2 M reads were captured per patient, with a range of 33.7 to 47.5M. The initial per gene and per transcript values were derived by: (i) mapping the short 50-mere reads to the GRCh37 version Human Genome Assembly with the Spliced Transcripts Alignment to a Reference (STAR) aligner [Dobin et al., 2013] followed by the quantification of transcript abundance with the RNA-Seq by Expectation-Maximization (RSEM) software package (Li and Wewey, 2011). Raw counts were used in the analysis.

Statistical analysis. All statistical analyses were performed using Python 2.7.15. FIG. 6A details a flow chart of cohorts used for feature selection, model training, and model validation, as well as the inclusion criteria used for final model development. FIG. 6B details a flow chart of the methodology used for predictive gene identification among cohort 1. Throughout 100 rounds of cross validation, 80% of samples were randomly selected for feature selection and model training. Among the 80% training samples, Mann-Whitney U-test was used to eliminate any features not significantly different in expression between responders and non-responders (p>0.05). The remaining features were subsequently further evaluated throughout 10 folds of cross validation in which Random Forest was used to rank each feature based on its mean decrease impurity. Features ranked in the top 100 in 5/10 cross validation folds were used to build a Random Forest model which was tested with the 20% withheld testing samples. This process was repeated 100 times and features that were selected in 30 out of the 100 iterations were considered predictive biomarkers for further evaluation.

Predictive biomarkers for response to anti-TNF therapy were further evaluated in an independent cohort of 231 patients collected from Consortium of Rheumatology Researchers of North America (CORRONA) (see section 3.1, Study populations). One hundred eighty five samples (80% of cohort) were used for finalized feature selection, clinical endpoint evaluation, and model training. Optimal model parameters and clinical endpoints were assessed through 10 repeats of 10% withheld cross validation which was repeated 50 times. Within each round of cross validation, the top 15 features ranked by Random Forest mean decrease in impurity were used to build a model which was tested on the withheld 10% of samples. For finalized feature selection, features were selected if they were ranked in the top 15 in greater than 4,000 out of the possible 5,000 selections. A finalized Random Forest model was subsequently trained using these selected features and validated among the remaining 46 samples in the cohort (20%).

Example 2

The present Example describes a cross-cohort, cross-platform development and validation of a classification algorithm that predicts at baseline, before the start of treatment, non-response to anti-TNF therapy in Rheumatoid Arthritis (RA) patients. Moreover, the present Example describes certain technologies that can be applied to development of other classifiers—e.g., that predict other features (such as, for example, likelihood of achieving or suffering a particular outcome or side effect, etc.) and/or that relate to other therapies.

(i) Methods
(1) Study Populations
a) Discovery Cohort

Patient microarray data (accession GSE15258) were obtained from the Gene Expression Omnibus (GEO). Details of sample collection and cohort information were previously reported. Briefly, RA patients naive to anti-TNF therapy were enrolled and blood samples collected in PAXgene tubes. Therapeutic response was evaluated 14 weeks after initiation of treatment according to the DAS28-CRP EULAR response definition. 58 female patient samples were used.

b) Training Cohort and Validation Cohort

RA patient whole blood samples and clinical measurements were prospectively collected in the CERTAIN trial by the Consortium of Rheumatology Researchers of North America (CORRONA). The CERTAIN study was designed as a prospective comparative effectiveness study involving 43 sites and 117 rheumatologists. Institutional Review Board and Ethics Committee approvals were obtained prior to sample collection and study participation. Samples selected for the present study were biologic-naïve at the time of sample collection (i.e., the patients had no experience with the following therapies: adalimumab, etanercept, infliximab, certolizumab pegol, golimumab, tocilizumab, rituximab, and abatacept). Patients were treated with adalimumab, etanercept, certolizumab pegol, golimumab or infliximab at the discretion of the treating physician and followed longitudinally for at least six months. In addition to a medical history, clinical assessments collected at zero and six months post therapy initiation included tender and swollen joint counts, physician and patient global disease activity scores, csDMARD dose, patient pain evaluation, and quality of life surveys. Laboratory studies performed at a central laboratory included a complete blood count, C-reactive protein (CRP) levels, rheumatoid factor titer, and anti-cyclic citrullinated protein (anti-CCP) titer. Characteristics of patient demographics and clinical variables are detailed in Table 3. Training (n=143) and validation trial (n=175) patient cohorts were balanced for response rate, age, and gender. Patients were included in the independent validation trial if they had a visual analogue scale pain score of at least 15 out of a maximum score of 100. Consistent with the inclusion criteria of the CERTAIN study, all patients in the validation trial had a CDAI greater than ten.

TABLE 3

| Characteristic | Training cohort (n = 143) | Validation trial cohort (n = 175) |
|---|---|---|
| Age, y (mean ± SD) | 55.0 ± 12.9 | 53.8 ± 11.9 |
| Female, % | 72.7 | 73.1 |
| Duration of disease, y (mean ± SD) | 4.7 ± 6.7 | 5.0 ± 7.5 |
| Positive for anti-cyclic citrullinated peptide, % | 66.9 | 60.9 |
| Positive for rheumatoid factor, % | 73.9 | 70.9 |
| Race | | |
| White | 88.1 | 84.6 |
| Black | 6.3 | 6.3 |
| Other | 5.6 | 9.1 |

TABLE 3-continued

| Characteristic | Training cohort (n = 143) | Validation trial cohort (n = 175) |
|---|---|---|
| csDMARD use, % | | |
| Methotrexate | 65.0 | 60.0 |
| Hydroxychloroquine | 3.5 | 4.0 |
| >=2 csDMARDS | 13.3 | 13.7 |
| None | 15.4 | 16.0 |
| Concomitant prednisone, % | 34.3 | 22.9 |
| Anti-TNF use, % | | |
| Adalimumab | 38.5 | 38.9 |
| Etanercept | 33.6 | 30.9 |
| Infliximab | 16.8 | 20.0 |
| Certolizumab pegol | 8.4 | 7.4 |
| Golimumab | 2.8 | 2.9 |
| CDAI (mean ± SD) | 28.5 ± 13.5 | 31.0 ± 12.6 |
| DAS28-CRP (mean ± SD) | 4.9 ± 1.1 | 5.0 ± 1.0 |
| Swollen joint count (mean ± SD) | 7.2 ± 6.0 | 8.1 ± 5.5 |
| Tender joint count (mean ± SD) | 10.8 ± 7.3 | 12.0 ± 7.3 |
| ACR50 Responders, % | 30.8 | 30.3 |

(2) Evaluation of Clinical Response to Anti-TNF Therapy

Among the CORRONA study samples, response at 6 months post anti-TNF therapy initiation was defined by ACR50 (ACR50 refers to a patient treatment target defined by the American College of Rheumatology, as patients who achieve either remission or low disease activity, and wherein the number (e.g., 50) refers to the percent improvement in a standard set of measures including number of swollen and tender joints, patient and physician report assessments and pain and global health, as well as serum biomarkers). A responder is an individual exhibiting >50% improvement in 28 tender joint count, >50% improvement in 28 swollen joint count and >50% improvement in at least 3 out of 5 clinical variables (disease index, patient pain, patient global assessment, physician global assessment and CRP level).

(3) RNA Isolation and QC

Total RNA was isolated from blood collected in PAXgene™ Blood RNA Tubes using the PAXgene™ Blood miRNA Kit (PreAnalytix) according to manufacturer's instructions. RNA quality was assessed using the Agilent Bioanalyzer and samples were quantitated using a NanoDrop™ ND-8000 spectrophotometer.

(4) RNA-Sequencing (RNAseq) Analysis and Gene Expression Preprocessing

RNA was processed using the GLOBINclear (Thermo Fisher®), Ribo-Zero Magnetic

Gold (Epidemiology), and TruSeq Stranded Total RNA (Illumina®) assay kits according to the manufacturer's instructions. Libraries were processed on a NextSeq® 550 DX or a NovaSeq® 6000 sequencer for 75 cycles. An average of 42.4 M reads were captured per patient, with a range of 33.7-58.6 M. 50-nt reads were mapped to the GRCh37 human genome with STAR. Per gene abundance in fragments per kilobase of transcript per million mapped reads (FPKM) was calculated with the RSEM software package. Samples with an RNA integrity score (RIN) of >4 or >7 million protein-coding reads were analyzed. No detectable batch effect was observed between the NextSeq® and NovaSeq® processed libraries based on a principal component analysis.

(5) Single-Nucleotide Polymorphism (SNP) Analysis

Among other things, the present disclosure provides an insight that SNP analysis provides particularly useful information to include in a classifier as described herein—e.g., developed with RNAseq data and/or with consideration of small but significant differences in gene expression levels, as described herein. To obtain SNP data, samples were aligned to the GRCh38 human genome with STAR. SNPs were called using a modified version of the Genome Analysis ToolKit Best Practices workflow for SNP and indel calling on RNAseq data. 39 RA-associated SNPs were evaluated.

(6) Machine Learning and Drug Response Algorithm Development 21,818 transcript features in the 58-patient discovery cohort were assessed. Among a randomly selected 80% of samples, the Mann-Whitney U test was used to eliminate any gene expression not significantly discriminatory between responders and non-responders (p>0.05). The Random Forest machine learning algorithm was used to rank each remaining feature based on its mean decrease impurity. The top 100 features were used to build a Random Forest model which was tested with the 20% subset of withheld data. This process was repeated 100 times and features that were selected in >30% of iterations were considered further. Gene expression for 26 of the 37 selected genes were detectable by RNAseq in the training cohort. Two additional features were eliminated due to low expression. During final model development, 70 discriminatory molecular and clinical characteristics (Tables 4-6) were evaluated by Random Forest as above using the training cohort data. The importance of each feature was assessed by removing it from the feature list and evaluating the model performance on the 20% subset of withheld data. The top 50% most important features were used to build a Random Forest predictive classification model using the entire training set. Model performance was evaluated using area under the receiver operating curve, negative predictive value and true negative rate. All statistical analyses were performed using Python 2.7.15.

Table 4 provides discriminatory gene set assessed during development of classification algorithm predictive of non-response to anti-TNFs in rheumatoid arthritis patients.

TABLE 4

| Gene name |
|---|
| ARPC1A |
| ATAT1 |
| ATRAID |
| CD27 |
| CHMP7 |
| COMMD5 |
| CORO2B |
| CYSLTR2 |
| DNAJC7 |
| GOLGA1 |
| HPCA |
| IMPDH2 |
| KAT8 |
| KLHDC3 |
| LOC100506083 |
| MORN2 |
| NGF |
| RHOBTB1 |
| RNGTT |
| SETD9 |
| SNX8 |
| SPINT2 |
| SPON2 |
| SSNA1 |
| STOML2 |
| SUOX |
| TMEM258 |
| UBL7-AS1 |

Table 5 provides SNPs assessed during development of classification algorithm predictive of non-response to anti-TNFs in rheumatoid arthritis patients

TABLE 5

| SNP |
| --- |
| chr1.161644258 |
| chr1.2523811 |
| chr11.107967350 |
| chr17.38031857 |
| chr7.128580042 |
| rs10774624 |
| rs10985070 |
| rs11889341 |
| rs1571878 |
| rs1633360 |
| rs17668708 |
| rs1877030 |
| rs1893592 |
| rs1980422 |
| rs2228145 |
| rs2233424 |
| rs2236668 |
| rs2301888 |
| rs2476601 |
| rs3087243 |
| rs3218251 |
| rs331463 |
| rs34536443 |
| rs34695944 |
| rs4239702 |
| rs4272 |
| rs45475795 |
| rs508970 |
| rs5987194 |
| rs657075 |
| rs6715284 |
| rs706778 |
| rs72634030 |
| rs73013527 |
| rs73194058 |
| rs773125 |
| rs7752903 |
| rs8083786 |
| rs9653442 |

Table 6 provides clinical factors available in this study from the CERTAIN cohort.

TABLE 6

| Clinical Characteristics |
| --- |
| Age |
| Gender at birth |
| Duration of disease (in years) |
| Race (included white, asian, black, mixed race, Native American, Pacific Islander, and other) |
| History of fibromyalgia |
| History of chronic vascular disease (includes acute coronary syndrome, coronary artery disease, congestive heart failure, hypertension, myocardial infarction, peripheral arterial disease, stroke, unstable angina, cardiac arrest, revascularization procedure, and ventricular arrhythmia) |
| History of serious infection that led to hospitalization (includes infections of bursa or joint, cellulitis, sinusitis, diverticulitis, sepsis, pneumonia bronchitis gastro meningitis, urinary tract infection, upper respiratory infection, and tuberculosis) |
| History of cancer (includes breast, lung, skin, lymphoma but excludes non-melanoma skin) |
| BMI |
| Smoking status (includes never, previous or current) |
| Prednisone dose |
| DMARD dose |
| C-reactive protein level at baseline |
| DAS28-CRP at baseline |
| Swollen 28-joint count at baseline |
| Tender 28-joint count at baseline |
| Patient global assessment at baseline |
| Physician global assessment at baseline |
| CDAI at baseline |
| Modified health assessment questionnaire score at baseline |
| Patient pain assessment at baseline |
| EULAR response at baseline using DAS28-CRP (includes poor, moderate or good) |
| Anti-CCP status (positive or negative) |
| Anti-CCP titer at baseline |
| Rheumatoid factor status (positive or negative) |
| Rheumatoid factor titer at baseline |

(7) Building the Human Interactome and RA Disease Module, and Performing Network Medicine Analyses of Molecular Features The human interactome was assembled as previously described from 21 public databases (Table 5) containing different types of experimentally-derived protein-protein interactions (PPI) data: 1) binary PPIs, derived from high-throughput yeast-two hybrid (Y2H) experiments (HI-Union), three-dimensional (3D) protein structures (Interactome3D, Instruct, Insider) or literature curation (PINA, MINT, LitBM17, Interactome3D, Instruct, Insider, BioGrid, HINT, HIPPIE, APID, InWeb); 2) PPIs identified by affinity purification followed by mass spectrometry present in BioPlex2, QUBIC, CoFrac, HINT, HIPPIE, APID, LitBM17, and InWeb; 3) kinase-substrate interactions from KinomeNetworkX and PhosphoSitePlus; 4) signaling interactions from SignaLink and InnateDB; and 5) regulatory interactions derived by the ENCODE consortium. A curated list of PSI-MI IDs provided by Alonso-Lopez et al. was used for differentiating binary interactions among the several experimental methods present in the literature-curation databases. Specifically for InWeb, interactions with curation score <0.175 ($75^{th}$ percentile) were not considered. All proteins were mapped in their corresponding Entrez ID (NCBI) and the proteins that could not be mapped were removed. The resulting Human Interactome includes 18,505 proteins and 327,924 interactions.

The DIAMOnD approach was used to generate an RA disease module. Proteins used to seed the disease module were linked to RA by at least two of five databases: (GWAS Catalog, HuGE Navigator Phenopedia, ClinVar, OMIM, and MalaCards). DIAMOnD identified proteins that were significantly enriched in the same Gene Ontology biological process terms as the disease-associated proteins.

Proximity of the molecular features to each other on the Human Interactome map was calculated as previously described. Briefly, the closest distance was defined as the average shortest path length between each protein and the next nearest protein in the set. Significance of the observed closest distance was evaluated in comparison to the expected closest distance determined from 10,000 random protein sets of the same size. Randomizations were performed as previously described.

(8) Pathway Enrichment Analysis

KEGG, Biocarta, Reactome, and Signal Transduction (ST) pathway annotations were obtained from the Molecular Signatures Database (MSigDB), Version 6.2. Fisher's exact test was used to identify biological pathways. Pathways with a Bonferroni corrected p-value of <0.05 were considered enriched. IL10, POMC, JAK1, ICOSLG, TNF, TNFSF11, NR3C1, P2RY12 (NCT02874092), PTGER4, GGPS1, FDPS, TNFRSF13B (NCT03016013), IL6, ESR1, ESR2, ITK (NCT02919475), BTK, TLR4 (NCT03241108), IRAK4, JAK2, JAK3, HDAC1 (NCT02965599), PSMB5, ADORA3, ITGA9 (NCT02698657, NCT03257852), IFNB1 (NCT02727764; NCT03445715), CX3CL1 were the approved drug targets in RA.

(ii) Results

Building the Human Interactome and a Map of RA Disease Biology

To begin developing the network medicine tools necessary to evaluate human disease biology, a map of cellular components and their physical interactions was created. By amalgamating publicly available data (Table 7) of 327,924 protein-protein interactions between a total of 18,505 proteins, a comprehensive map of biology called the Human Interactome was created (see Methods).

TABLE 7

| Databases | Interaction type | Evidence type |
| --- | --- | --- |
| APID | Binary/Co-complex | Literature curation |
| BioGrid | Binary | Literature curation |
| BioPlex2 | Co-complex | High-throughput |
| CoFrac | Co-complex | High-throughput |
| ENCODE | Regulatory | High-throughput |
| HI-Union | Binary | High-throughput |
| HINT | Binary/Co-complex | Literature curation |
| HIPPIE | Binary/Co-complex | Literature curation |
| InnateDB | Signaling | Literature curation |
| Insider | 3D/Binary | Literature curation |
| Instruct | 3D/Binary | Literature curation |
| IntAct | Binary | Literature curation |
| Interactome3d | 3D/Binary | Literature curation |
| InWeb (Score > 0.175 only) | Binary/Co-complex | Literature curation |
| KinomeNetworkX | Kinase-substrate | Literature curation |
| LitBM17 | Binary/Co-complex | Literature curation |
| MINT | Binary | Literature curation |
| PhosphoSitePlus | Kinase-substrate | Literature curation |
| PINA | Binary | Literature curation |
| QUBIC | Co-complex | High-throughput |
| SignaLink | Signaling | Literature curation |

Disease-associated proteins tend to interact with each other in a sub-network on the Human Interactome called a disease module. Using the DIAMOnD approach that aggregates potential disease-associated proteins based on their proximity to known disease-associated proteins, an RA disease module was generated that contains approximately 200 proteins. Of these, 66% were linked to RA in genome-wide association study databases and DIAMOnD identified the remaining proteins that are significantly enriched in the same Gene Ontology biological process terms as the disease-associated proteins.

Using the Human Interactome and the RA disease module, the present application sought to create a blood-based classification algorithm that integrates clinical variables and molecular features to predict which RA patients will not respond to anti-TNF therapy (FIG. 11). Briefly, molecular features that discriminate between responders and non-responders to anti-TNF therapies were selected from a publicly available microarray dataset. In a cross-platform analysis, these features were combined with RA disease module-associated SNPs and clinical factors. A machine learning algorithm was trained using RNAseq data. Finally, performance of the predictive drug response algorithm was validated in an independent validation trial.

(1) Cross-Platform Identification of Discriminatory Gene Expression in Whole Blood Predictive of Inadequate Response to Anti-TNF Therapy in RA Patients To maximize the clinical utility of a test that predicts non-response to therapy, a routine non-invasive or minimally invasive sample source that does not require specialized specimen collection procedures is ideal. For this reason, gene expression data derived from whole blood was analyzed. Gene expression that is discriminatory between patients considered responders and non-responders to anti-TNF therapies were selected from a publicly available microarray discovery cohort dataset of 58 biologic-naïve RA patients using the Random Forest machine learning algorithm. Of the 21,818 genes in the discovery dataset for which gene expression was assessed, 37 were discriminatory between responders (n=24) and non-responders (n=51) to anti-TNF therapies (FIG. 9; Table 3). Transcriptional profiling by microarray and RNAseq varies in dynamic range and exhibits some discordance in the number and extent of differential gene expression observed. Nonetheless, a large fraction of the transcripts identified as discriminatory of anti-TNF drug response in microarray data also differentiated between responders and non-responders in RNAseq data.

(2) Evaluation of Disease-Associated SNPs from RNAseq Data

RNAseq provides information on nucleotide sequence that is lacking from microarray analyses. In addition to gene expression, variations in RNA sequence may be predictive of non-response to anti-TNF therapy in RA patients. To this end, a training dataset was generated from clinical data and whole blood RNAseq data obtained from 143 RA patients in the CORRONA CERTAIN study. Characteristics and demographics of the patient populations are summarized in Table 3. Although SNP analysis is traditionally performed on whole genome sequencing data, the majority of the genome is transcribed. Therefore, most SNP variants can be detected in ribosomal RNA-depleted RNAseq data. Several SNPs that are associated with rheumatoid arthritis have been functionally linked to gene expression changes in peripheral blood mononuclear cells through expression quantitative trait loci (eQTL) analysis (Table 4). The genetic loci associated with the selected SNPs have a significant overlap with the RA disease module (FIG. 8B). Twenty-two such SNPs were above the limit of detection in the patient RNAseq data and were included in further analyses (FIG. 9).

(3) Integration of SNPs, Gene Expression Data, and Clinical Variables to Develop a Multi-Factorial Predictive Drug Response Algorithm Gene expression indicative of drug response (Table 4), RA-associated SNPs (Table 5) and clinical factors (Table 6) were used to train and develop a drug response algorithm that is predictive of non-response to anti-TNF therapies. Using ACR50 at six months as a benchmark, the training cohort population had a response rate to anti-TNF therapies of 30.8%. This is representative of the general population and reflects the real-world prospective collection approach of the CORRONA CERTAIN study. Random Forest was used to generate predictive models with 80% of the RNAseq training dataset using features from the discriminatory gene expression set, the SNPs as well as clinical factors, or combinations thereof. Cross-validation on the remaining 20% of the training dataset evaluated model performance using area under the receiver operating characteristic curve. This analysis evaluates the relationship between false positives and true positives to measure how well a model can distinguish between responders and non-responders. The model most predictive of non-response to anti-TNF therapy was generated using a combination of all three feature types. The area under receiver operating curve (AUC) of the model cross-validation performance was 0.66. With the clinical factors alone, the AUC was 0.56 and with the molecular features alone, the AUC was 0.64 (Table 8). The cross-validation performance data confirms the critical importance of the transcript and SNP features in the classifier. Table 8 provides cross-validation results from models using the full feature set and its subsets.

TABLE 8

| Features used to build Random Forest model | Area under the curve |
|---|---|
| Discriminatory genes, SNPs, and clinical factors | 0.66 |
| Discriminatory genes and SNPs | 0.64 |
| Clinical factors only | 0.56 |

(4) Blinded Independent Validation Trial of PrismRA®, a Biomarker Panel Predictive of Non-Response to Anti-TNF Therapy in RA Patients Many studies have hypothesized that the biology of non-response to anti-TNF therapy is reflected in the transcriptome of whole blood. However, none have been translated into the clinic, which is likely a reflection of both the complexity of RA disease biology and the varying methodologies used for algorithm development. Furthermore, limited sample sizes and the complexity of gene expression data analyses have thus far prevented development of an algorithm that is generalizable across patient cohorts and to the wider patient population. To confirm that the PrismRA® biomarker panel consisting of 12 SNPs, 8 transcripts, 2 laboratory tests and 3 basic demographic factors (sex, BMI, patient disease assessment) is generalizable, an independent group of prospectively collected samples (n=175) was used to conduct a blinded validation trial. The samples included in the validation cohort were not used for any stage of algorithm development and the algorithm has no information derived from the gene expression data or clinical outcomes from these patients.

Blinded, independent validation of the PrismRA® biomarker panel stratified the validation cohort into predicted non-responders and responders with a highly statistically significant odds ratio of 0.152 (CI 0.064, 0.364) of being a responder in the respective subgroup. PrismRA® biomarker panel identified 50.0% (specificity) of non-responder patients with 89.7% (negative predictive value) accuracy (Table 9). Patients predicted to be non-responders have an observed ACR50 response rate of 10.3% with anti-TNFs, significantly lower than the overall response rate of 30.3%. Redirecting these individuals to alternative therapies would greatly increase their likelihood of achieving meaningful clinical change. Conversely, the predicted responders have an observed ACR50 response rate of 43.0%, which is a 41.8% improvement from that of the unstratified patient population. Table 9 provides PrismRA® predictive biomarker panel validation performance.

TABLE 9

|  | ACR50 (R) | ACR50 (NR) | Sum |
|---|---|---|---|
| PrismRA ® (R) | 46 | 61 | 107 |
| PrismRA ® (NR) | 7 | 61 | 68 |
| Sum | 53 | 122 |  |

(5) Biological Interpretation of Gene Products that Discriminate Between Responders and Non-Responders to Anti-TNF Therapy The Human Interactome map of all known protein-protein interactions provides a unique vantage point to evaluate the underlying biology of non-response to anti-TNF therapy. To characterize the applicability of the PrismRA® predictive biomarker panel to RA disease biology, the protein products of the discriminatory genes and SNP eQTLs were analyzed using the Human Interactome and pathway enrichment analyses. The proteins encoded by the discriminatory genes and SNP eQTLs included in the PrismRA® biomarker panel were overlaid on the Human Interactome map (FIG. 8A). In total, 42 proteins mapped onto the Human Interactome: 24 are contributed by the discriminatory genes and 18 by the SNP eQTLs. These molecular features are interwoven on the map highlighting a small, yet cohesive biological network that unifies the subpopulation of RA patients that will not respond to anti-TNF therapy. Quantification of this proximity (see Methods) indicates that these different molecular features are significantly close to each other (z-score=−2.18). Furthermore, RA disease module (z-score=−4.09) and RA drug targets such as JAK and TNF (z-score=−3.98) are proximal to SNPs and DGs collectively (FIG. 8B).

Pathway enrichment analysis was performed to gain insight into the molecular pathways involved in anti-TNF therapy response. T cell signaling was identified as the most enriched pathway in the pathway analysis databases queried. The relevance and importance of T cell signaling to both anti-TNF therapy response and the disease biology of RA is well established.

(iii) Discussion

By incorporating microarray gene expression data, RNA next generation sequencing, biological network analyses, and machine learning to large patient cohorts, this study demonstrates that a drug response algorithm that uses whole blood gene expression data to predict non-response to anti-TNF therapy can perform across different RA patient cohorts. A prospectively collected RNAseq dataset used for a blinded, independent validation trial of PrismRA® biomarker panel demonstrated that the drug response algorithm could predict non-response to anti-TNF therapy in an independent population of RA patients with 90% accuracy. Anti-TNF therapy fails to help nearly 70% of the unstratified patient population reach treatment targets. Incorporation of PrismRAx predictive algorithm into clinical care would reduce this number by more than half The predictive drug response algorithm was derived from discriminatory molecular features identified in a microarray dataset and further evaluated in conjunction with clinical factors from a second dataset derived from RNAseq data. These two gene expression analysis platforms differ in RNA detection methodologies and statistical tools to determine normalized gene expression values. Despite these differences in technology, the cross-platform and cross-cohort universality of the molecular features identified in this study highlights the presence of a robust and generalizable molecular process underlying the biology of anti-TNF drug response.

A single large-scale high-throughput analysis approach has yet to capture the complete molecular architecture of RA disease biology. SNPs can affect many aspects of cellular biology including the propensity for regulatory elements to interact with their cognate protein partners, the ratio or identity of alternative splice variants produced from a gene locus, transcript levels, and protein sequence. Therefore, the functional readout of disease-associated SNPs contributes to the propensity of an individual to develop disease as well as the inclination for environmental factors to influence pathobiology. Many regulatory elements and genomic regions that do not encode protein are transcribed, such as in the form of enhancer RNAs and promoter-associated transcripts. Thus, many SNPs that influence spatial- and temporal-specific changes in transcription can be evaluated from RNAseq data. Together, SNP and gene expression analyses can capture phenotypic variation and pathway associations that may otherwise be obscured. Integrating nucleotide variants and discriminatory gene expression into a single predictive algorithm generated actionable insight into disease pathogenesis and drug response.

Customization of treatment regimens to match the individualized disease biology of each patient is the goal of modern medicine. This personalized approach to medicine is used in oncology, where particular therapies are prescribed to patients with specific genomic markers. The complexity and heterogeneity of autoimmune diseases such as RA necessitate novel and multifaceted approaches to develop clinically useful tools. Examination of the molecular pathways that identify patients that will not respond to anti-TNF therapy demonstrated a connection between T cell signaling and RA disease biology. Synovial inflammation results from leukocyte infiltration into and retention in the synovial compartment, as well as from insufficient apoptosis of chronic inflammatory cells. This synovial infiltrate includes natural killer (NK) cells, CD4+, and CD8+ T cells. Furthermore, large numbers of activated T regulatory cells can be detected in the joints of RA patients. The remaining discriminatory genes that are not associated with T cell signaling likely represent different aspects of RA disease that differ between those patients that will or will not respond to anti-TNF therapy. The connection to RA disease biology speaks to the reliability and applicability of PrismRA® predictive algorithm to be a powerful clinical tool for identification of anti-TNF non-responders.

For patients predicted to inadequately respond to anti-TNF therapies, alternative biologics and targeted synthetic therapies provide improved safety and efficacy through rapid and sustained improvements in disease activity with ACR50 response rates of 30-40% at six months following alternative treatment initiation. Several such alternative therapies are endorsed as first-line therapies by the FDA and by RA patient treatment guidelines. Incorporating this stratifying predictive classification algorithm as a blood test into the clinical care of RA will result in faster achievement of low disease activity for more patients. This would save months or even years of a patient's time, prevent potential disease progression, avoid exposure to the potentially serious side effects associated with cycling of anti-TNF therapies, and reduce health care expenditures on ineffective treatments and management of adverse events.

Development and validation of a drug response algorithm that predicts non-response to a targeted therapy using this machine learning and network medicine approach shows great promise for advancing precision medicine not only for RA but for other complex autoimmune diseases.

The foregoing has been a description of certain non-limiting embodiments of the subject matter described within. Accordingly, it is to be understood that the embodiments described in this specification are merely illustrative of the subject matter reported within. Reference to details of the illustrated embodiments is not intended to limit the scope of the claims, which themselves recite those features regarded as essential.

It is contemplated that systems and methods of the claimed subject matter encompass variations and adaptations developed using information from the embodiments described within. Adaptation, modification, or both, of the systems and methods described within may be performed by those of ordinary skill in the relevant art.

Throughout the description, where systems are described as having, including, or comprising specific components, or where methods are described as having, including, or comprising specific steps, it is contemplated that, additionally, there are systems encompassed by the present subject matter that consist essentially of, or consist of, the recited components, and that there are methods encompassed by the present subject matter that consist essentially of, or consist of, the recited processing steps.

It should be understood that the order of steps or order for performing certain action is immaterial so long as any embodiment of the subject matter described within remains operable. Moreover, two or more steps or actions may be conducted simultaneously.

What is claimed is:

1. A method of treating a subject suffering from rheumatoid arthritis, the method comprising administering to the subject an alternative to anti-TNF therapy,
   wherein the subject has been predicted to be non-responsive to the anti-TNF therapy based at least in part on a trained machine learning classifier that distinguishes between responsive subjects and non-responsive subjects who have received the anti-TNF therapy,
   wherein the trained machine learning classifier distinguishes between the responsive subjects and the non-responsive subjects, based at least in part on analyzing an expression level in the subject of a set of genes.

2. The method of claim 1, wherein the trained machine learning classifier further analyzes:
   presence of one or more single nucleotide polymorphisms (SNPs) in a sequence of one or more genes that are expressed in the subject; or
   presence of one or more clinical characteristics of the subject.

3. The method of claim 2, wherein the one or more clinical characteristics of the subject comprise a member selected from the group consisting of body-mass index (BMI), gender, age, race, previous anti-TNF therapy treatment, disease duration of rheumatoid arthritis, C-reactive protein level, presence of anti-cyclic citrullinated peptide, presence of rheumatoid factor, patient global assessment, and treatment response rate to anti-TNF therapy.

4. The method of claim 1, wherein the alternative to anti-TNF therapy comprises rituximab, sarilumab, tofacitinib citrate, leflunomide, vedolizumab, tocilizumab, anakinra, or abatacept.

5. The method of claim 1, wherein the alternative to anti-TNF therapy comprises anti-CD20, JAK, or anti-IL6 therapy.

6. The method of claim 1, wherein the trained machine learning classifier predicts the subject to be non-responsive to the anti-TNF therapy using a non-linear relationship between (i) an expression level of one or more genes identified in the subject and (ii) responsiveness or non-responsiveness to the anti-TNF therapy.

7. The method of claim 1, wherein the trained machine learning classifier is trained using expression levels of a set of genes in (i) a first set of subjects with rheumatoid arthritis who were responsive to the anti-TNF therapy and (ii) a second set of subjects with rheumatoid arthritis who were non-responsive to the anti-TNF therapy.

8. The method of claim 1, wherein the trained machine learning classifier comprises a neural network or a random forest.

9. The method of claim 1, wherein the trained machine learning classifier predicts that subjects within a population are non-responsive to the anti-TNF therapy with a true negative rate (TNR) of at least about 60%.

10. The method of claim 1, wherein the set of genes comprises ARPC1A, ATAT1, CD27, MORN2, SNX8, SSNA1, UBL7-AS1, ATRAID, CHMP7, COMMD5, CORO2B, CYSLTR2, DNAJC7, GOLGA1, HPCA, IMPDH2, KAT8, KLHDC3, LOC100506083, NGF, RHOBTB1, RNGTT, SETD9, SPINT2, SPON2, STOML2, SUOX, or TMEM258.

11. The method of claim 1, wherein the trained machine learning classifier predicts that subjects within a population are non-responsive to the anti-TNF therapy with a negative predictive value (NPV) of at least about 85%.

12. The method of claim 1, wherein the trained machine learning classifier predicts that subjects within a population are non-responsive to the anti-TNF therapy with an area under the curve (AUC) of at least about 70%.

13. The method of claim 1, wherein the trained machine learning classifier predicts that subjects within a population are non-responsive to the anti-TNF therapy with an accuracy of at least about 90%.

14. The method of claim 2, wherein the one or more SNPs comprise a member selected from the group consisting of chr1.161644258, chr1.2523811, chr11.107967350, chr17.38031857, chr7.128580042, rs10774624, rs10985070, rs11889341, rs1571878, rs1633360, rs17668708, rs1877030, rs1893592, rs1980422, rs2228145, rs2233424, rs2236668, rs2301888, rs2476601, rs3087243, rs3218251, rs331463, rs34536443, rs34695944, rs4239702, rs4272, rs45475795, rs508970, rs5987194, rs657075, rs6715284, rs706778, rs72634030, rs73013527, rs73194058, rs773125, rs7752903, rs8083786, and rs9653442.

* * * * *